(12) United States Patent
Warren

(10) Patent No.: US 6,610,841 B1
(45) Date of Patent: Aug. 26, 2003

(54) NUCLEOTIDE-BASED PRODRUGS

(75) Inventor: Stephen Warren, Boulder, CO (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 08/993,765

(22) Filed: Dec. 18, 1997

(51) Int. Cl.$^7$ .......................... C07H 19/00; C07H 1/06
(52) U.S. Cl. ................ 536/25.3; 536/25.33; 536/25.34; 536/25.5; 536/25.6; 536/26.26; 536/26.6; 536/26.7; 536/26.71; 536/26.8; 514/45; 514/46; 514/47; 514/48; 514/49; 514/50; 514/51; 435/6; 435/91.1
(58) Field of Search .............................. 514/45, 46, 47, 514/48, 49, 50, 51; 536/25.3, 25.33, 25.34, 25.5, 25.6, 26.26, 26.6, 26.7, 26.71, 26.8; 435/6, 91.1

(56) References Cited

U.S. PATENT DOCUMENTS

| | | | |
|---|---|---|---|
| 5,411,947 A | | 5/1995 | Hostetler et al. |
| 5,457,187 A | | 10/1995 | Gmeiner et al. |
| 5,484,809 A | | 1/1996 | Hostetler et al. |
| 5,554,728 A | | 9/1996 | Basava et al. |
| 5,591,851 A | | 1/1997 | Alexander |
| 5,607,691 A | * | 3/1997 | Hale et al. ..................... 514/1 |
| 5,614,503 A | | 3/1997 | Chaudhary et al. |
| 5,614,505 A | | 3/1997 | Gmeiner et al. |
| 5,663,321 A | | 9/1997 | Gmeiner et al. |
| 5,798,340 A | | 8/1998 | Bischofberger et al. |

FOREIGN PATENT DOCUMENTS

| | | |
|---|---|---|
| GB | 2 183 661 A | 6/1987 |
| WO | WO89/06694 | 7/1989 |
| WO | WO90/10448 | 9/1990 |
| WO | WO92/14843 | 9/1992 |
| WO | WO93/25197 | 12/1993 |

OTHER PUBLICATIONS

Joyce (1989) Gene 82:83.
Joyce & Inoue (1989) Nucleic Acids Research 17:711.
Ellington & Szostak (1990) Abstracts of papers presented at the 1990 meeting on RNA Processing, Cold Spring Habor Laboratory, Cold Spring Harbor. NY. p. 84.
Kinzler & Vogelstein (1989) Nucleic Acids Research 17:3645.
Kramer et al. (1974) J. Mol. Biol. 89:719.
Levisohn & Spiegelman (1969) PNAS USA 63:803.
Levisohn & Spiegelman (1968) PNAS USA 60:866.
Oliphant et al. (1989) Mol. Cell. Biol. 9:2944.
Oliphant & Struhl (1988) Nucleic Acids Research 16:7673.
Oliphant & Struhl (1987) Methods in Enzymology 155:568.
Oliphant et al. (1986) Gene 44:177.
Robertson & Joyce (1990) Nature 344:467.
Thiesen & Bach (1990) Nucleic Acids Research 18:3203.
Szostak, "Structure and Activity of Ribozymes," in *Redesigning the Molecules of Life*, (S.A. Benner ed.) Springer–Verlag Berlin Heidelberg, pp. 87–113, (1988).

* cited by examiner

Primary Examiner—James O. Wilson
(74) Attorney, Agent, or Firm—Swanson & Bratschun, L.L.C.

(57) ABSTRACT

This invention relates to nucleotide-based prodrugs and their drug-delivery applications. The nucleotide-based prodrugs of the present invention comprise a drug component covalently attached via junctional ester bond(s) to one or more nucleotide components. Release and activation of the drug component of a nucleotide-based prodrug arises from hydrolysis of the junctional ester bond joining the nucleotide component to the drug component. The active drug component may be a nucleoside analog, a nucleic acid ligand, or a non-nucleoside drug. The nucleotide component provides a means of targeting and/or anchoring the nucleotide-based prodrug to the desired tissue compartment and/or a mechanism of sustained release of the active drug, thereby providing for a more effective drug delivery system with reduced toxicity. The targeting and/or anchoring of the nucleotide-based prodrugs to the desired tissue can be achieved through several methods, including employing a nucleic acid ligand as the nucleotide component, and/or by incorporating photocrosslinkable bases into the nucleotide component, and/or by covalently bonding the nucleotide component to a macromolecular support. The invention further includes lipid constructs comprising a nucleotide-based prodrug.

38 Claims, 25 Drawing Sheets

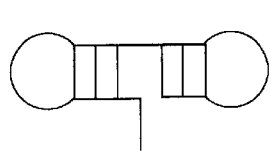
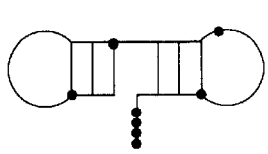
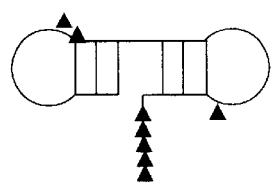
Fig. 1A     Fig. 1B     Fig. 1C
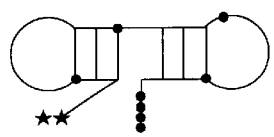
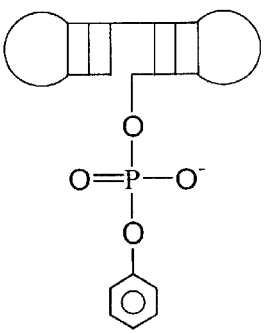
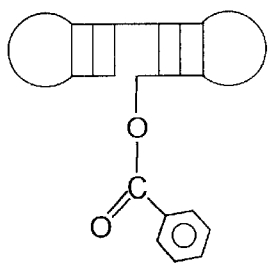
Fig. 1D     Fig. 1E     Fig. 1F
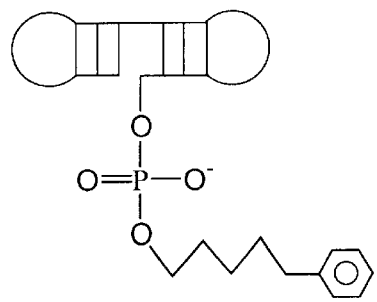
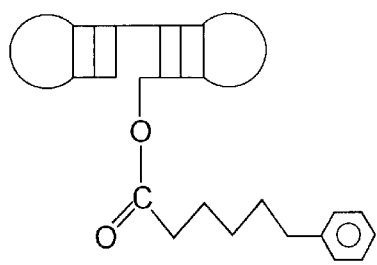
Fig. 1G     Fig. 1H
| | | | |
|---|---|---|---|
| ▥▥▥ | Nucleotide Polymer, Base-Paired | ★ | Photocrosslinkable Nucleotide |
| ⌒ | Nucleotide Polymer, Non-Base-Paired | ▲ | Radioactive Nucleotide |
| ⌒▥▥⌒ | Aptamer, Nucleic Acid Ligand | —⬡ | Pharmacologically Active Non-Nucleoside Drug |
| • | Pharmacologically Active Nucleoside Analog | ∿∿ | Adaptor Molocule |

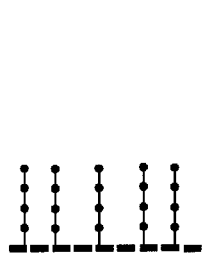
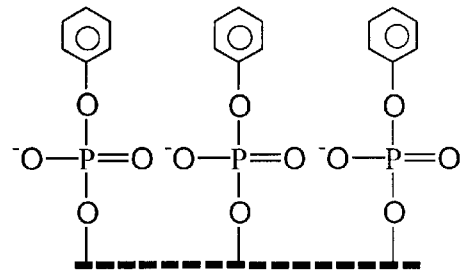
Fig. 2A      Fig. 2B
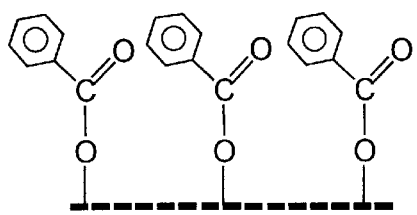
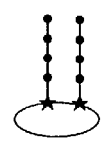
Fig. 2C      Fig. 2D
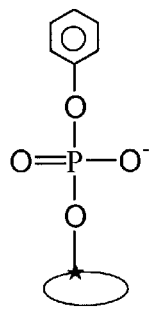
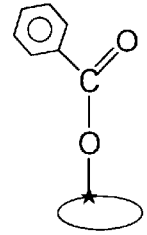
Fig. 2E      Fig. 2F
---
— Nucleotide Polymer
• Pharmacologically Active Nucleoside Analog
★ Photocrosslinkable Nucleotide
—⌬ Pharmacologically Active Non-Nucleoside Analog
----- Macromolecular Support
◯ Tissue Macromolecule R = H, OH, F, OCH₃
or other modification

• $^{32}P$ containing Nucleotide

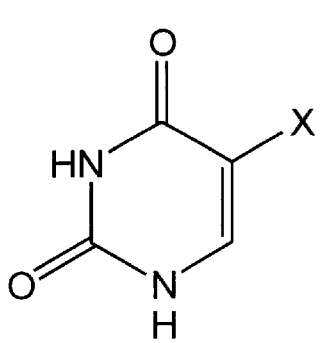
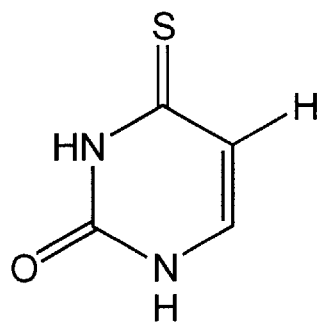
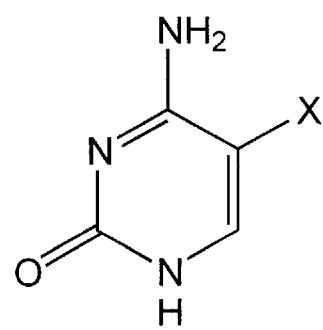
Fig. 7A      Fig. 7B      Fig. 7C
$X = Br, I, CH_2=CHBr, CH_2=CHI, N_3$
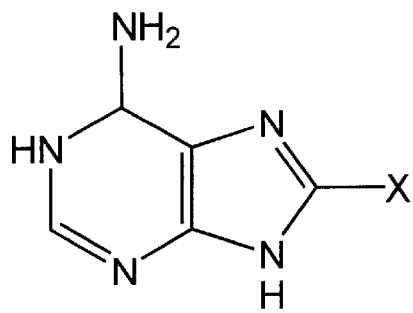
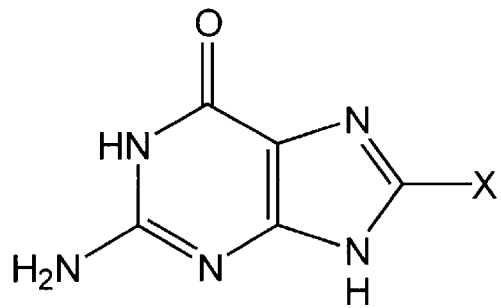
Fig. 7D      Fig. 7E
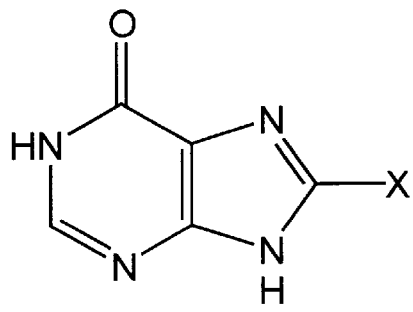
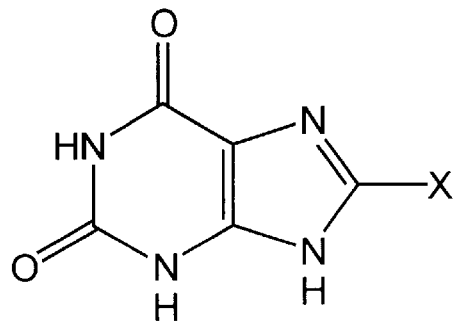
Fig. 7F      Fig. 7G
$X = N_3, Br$ or $I$

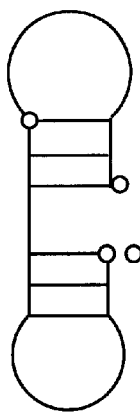
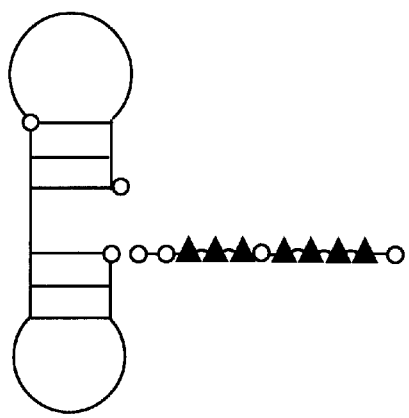
● = 2' Deoxycoformycin
○ = 4-thiouridine
▲ = 2-chlorodeoxyadenosine (cladribine)
Fig. 8A                Fig. 8B
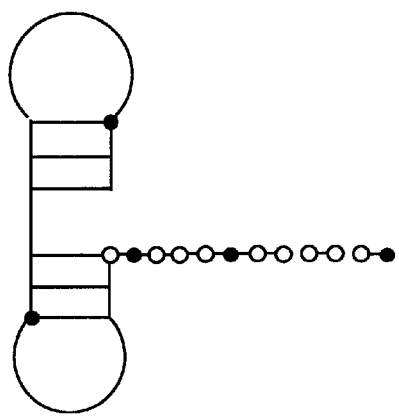
○ = 4-thiouridine
● = Cytosine Arabinoside (AraC)
Fig. 9

○ = 2' Deoxycoformycin
● = 6-mercaptopurine (6-MP)

| | |
|---|---|
| —— | Nucleotide Polymer |
| ◐ | Pharmacologically Active Nucleoside Analog #1 |
| ○ | Pharmacologically Active Nucleoside Analog #2 |
| ----- | Macromolecular Support |

- Nucleotide Polymer
- ο Pharmacologically Active Nucleoside Analog #1
- o Pharmacologically Active Nucleoside Analog #2
- ▬▬▬ Macromolecular Support
- ↓ Site of Endonucleolytic Cleavage R = H, OH, F, NH$_2$, etc.
N = Any Base
$n$ = 1-100
~~~ Any covalent bond - preferably more resistant to cleavage than internucleotide bonds

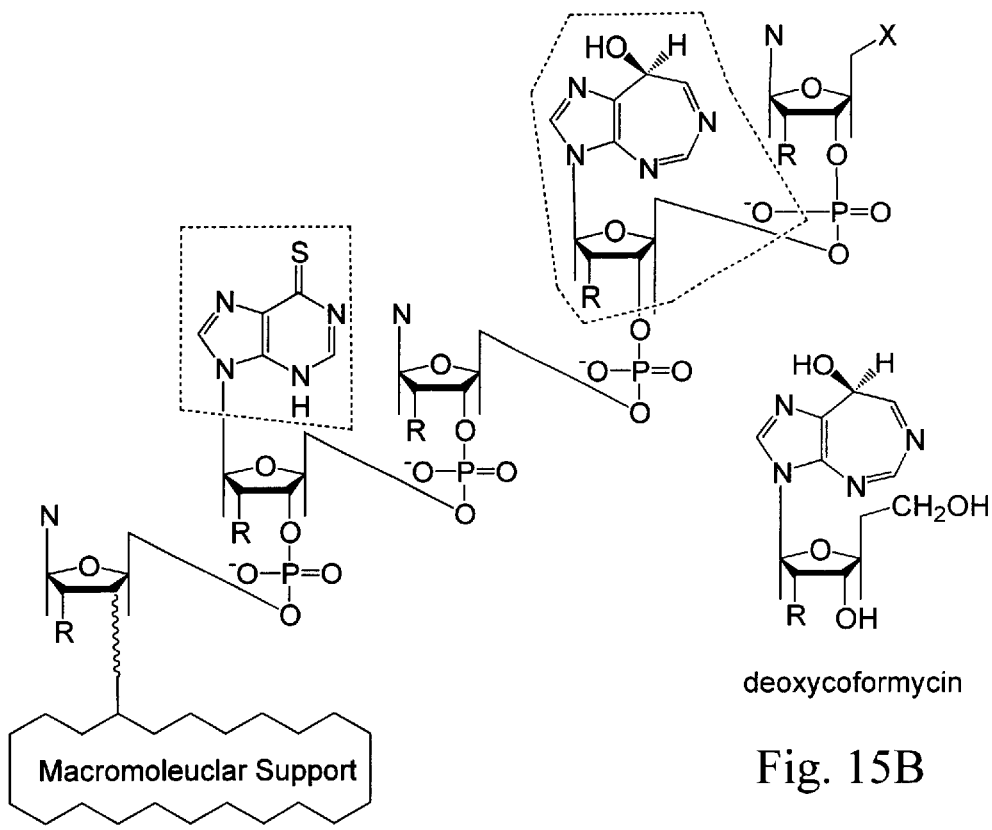
deoxycoformycin
Fig. 15B
Fig. 15A
R = H, OH, F, NH$_2$, OCH$_3$, etc.
N = Any Base
X = Any nucleotide or nucleotide Polymer
∿ Any covalent bond - preferably more resistant to cleavage than internucleotide bonds
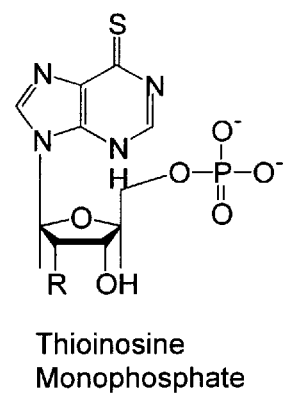
Thioinosine
Monophosphate
Fig. 15C

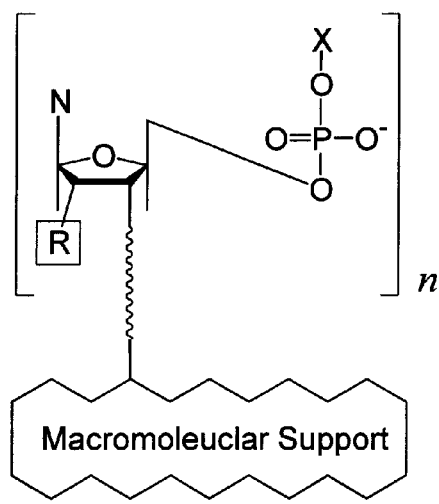
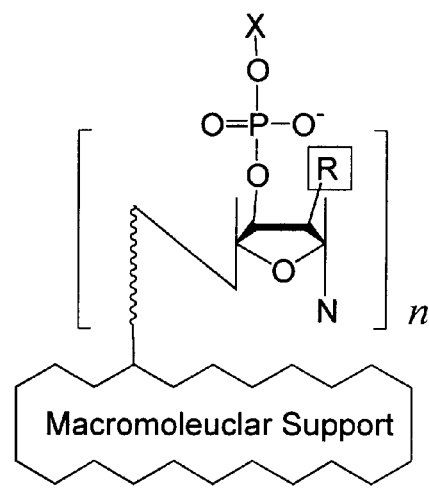
Fig. 18A
Fig. 18B
R = H, OH, F, $NH_2$, $OCH_3$, etc.
N = Any Base
X = Drug with hydroxyl group
n = 1-25
∼∼∼ Any covalent bond - preferably more resistant to cleavage than bond between X and nucleotide or nucleotide polymer R = H, OH, F, NH₂, OCH₃, etc.
N = Any Base
X = Drug with carboxyl group
n = 1-25
∿∿∿ Any covalent bond - preferably more resistant to cleavage than bond between X and nucleotide or nucleotide polymer R = H, OH, F, NH$_2$, OCH$_3$, etc.
N = Any Base
n = 1-25
∿∿ Any covalent bond - preferably more resistant to cleavage than bond between X and nucleotide or nucleotide polymer R = H, OH, F, NH$_2$, OCH$_3$, etc.
N = Any Base
n = 1-25
〜〜  Any covalent bond - preferably more resistant to cleavage than bond between X and nucleotide or nucleotide polymer R = H, OH, F, NH$_2$, OCH$_3$, etc.
N = Any Base
$n$ = 1-25
〰〰  Any covalent bond - preferably more resistant to cleavage than bond between X and nucleotide or nucleotide polymer R = H, OH, F, NH$_2$, OCH$_3$, etc.
N = Any Base
$n$ = 1-25
〰〰 Any covalent bond - preferably resistant to enzymatic cleavage

SEQUENCE LISTING

<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(17)
<223> OTHER INFORMATION: U's at postions 2, 4, 6, 8, 10, 12, 14, and 16
      are 5-bromo-deoxyuridine; A's at positions 1, 9 and 17 are
      deoxyadenosine; C's at positions 3 and 11 are deoxycytosine;
<221> NAME/KEY: modified_base
<222> LOCATION: (1)..(17)
<223> OTHER INFORMATION: G's at positions 5 and 13 are deoxyguanosine;
      T's at positions 7 and 15 are deoxythymidine.

<400> SEQUENCE: 1
aucugutuau cugutua                                                  17

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(18)
<223> OTHER INFORMATION: U's at positions 2,4, 6, 8, 10, 12, 14 and 16
      are 5-bromo-deoxyuridine; A's at positions 1, 9, and
      17 are deoxyadenosine; C's at positions 3 and 11 are
      deoxycytosine;
<221> NAME/KEY: modified_base
<222> LOCATION: (1)..(18)
<223> OTHER INFORMATION: G's at positions 5 and 13 are deoxyguanosine;
      T's at positions 7 and 15 are deoxythymidine; T at position 18 is
      a 3'-3' dT cap.

<400> SEQUENCE: 2
aucugutuau cugutuat                                                 18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence
<221> NAME/KEY: modified_base
<222> LOCATION: (1)..(18)
<223> OTHER INFORMATION: A's at positions 1, 9 and 17 are 2'-OMe
      adenosine; C's at positons 3 and 11 are 2'OMe cytosine; G's at
      positions 5 and 13 are 2' OMe guanosine;
<221> NAME/KEY: modified_base
<222> LOCATION: (1)..(18)
<223> OTHER INFORMATION: U's at positions 2, 4, 6, 8, 10, 12 14 and 16
      are 5-bromodeoxyuridine; T's at positions 7 and 15 are 2'- OMe
      thymidine; T at position 18 is a 3' - 3'dT cap.

<400> SEQUENCE: 3
aucugutuau cugutuat                                                 18

NUCLEOTIDE-BASED PRODRUGS

FIELD OF THE INVENTION

This invention relates generally to the treatment of diseases using nucleotide-based prodrugs. More particularly, the present invention relates to nucleotide-based prodrugs and their drug-delivery applications. The nucleotide-based prodrugs of the present invention comprise a drug component covalently attached via junctional ester bond(s) to one or more nucleotide components. Release and activation of the drug component of a nucleotide-based prodrug arises from hydrolysis of the junctional ester bond joining the nucleotide component to the drug component. The active drug component may be a nucleoside analog, a nucleic acid ligand, or a non-nucleoside drug. The nucleotide component provides a means of targeting and/or anchoring the nucleotide-based prodrug to the desired tissue compartment and/or a mechanism of sustained release of the active drug, thereby providing for a more effective drug delivery system with reduced toxicity. The targeting and/or anchoring of the nucleotide-based prodrugs to the desired tissue can be achieved through several methods, including employing a nucleic acid ligand as the nucleotide component, and/or by incorporating photocrosslinkable bases into the nucleotide component, and/or by covalently bonding the nucleotide component to a macromolecular support. The invention further includes lipid constructs comprising a nucleotide-based prodrug.

BACKGROUND OF THE INVENTION

Current Methods of Sustained Release Drug Delivery

Many controlled release, tissue-targeted drug delivery systems have been developed and investigated in the laboratory, but few have reached the pharmaceutical marketplace. For reviews of this area of drug delivery research. (See Tomlinson, E. (1987) *Adv. Drug Delivery Rev.* 1:87–198 and Chein Y. W. 1992. Novel Drug Delivery Systems, New York, N.Y. Marcel Dekker, Inc. Many of the obstacles confronting scientists in this area of drug delivery research are illustrated by the examples provided below.

Insoluble Drug Depots

The most widely used slow release drug depots are contraceptive progestins implanted subcutaneously (e.g., Depo-Provera®). Some progestin formulations are encapsulated in permeable silicone chambers (e.g., Norplant®). Corticosteroid depots are also available (e.g., Depo-Medrol®). The deposition and sustained release of these drugs relies upon their relatively low solubilities in aqueous fluids. The steroids slowly dissolve at the surface of the implant, and diffuse into surrounding interstitium and capillaries. This sustained release technology is based entirely upon the drugs' physicochemical properties, the geometry of the implant and its location in the tissue. The contraceptive's target tissues (hypothalamus and adenohypophysis) are far removed from the depot, but low systemic drug levels are effective. The situation is different in the case of corticosteroid suspensions, which are used to treat locally inflamed tissues. A suspension of insoluble corticosteroid (DepoMedrol®) is injected directly into the tissue, so the targeting of the drug is crude. The drug's absorption into local capillaries can lead to relatively high systemic levels and toxicity. Thus, only a few DepoMedrol® injections can be given to a patient each year.

Polymers Impregnated with Drugs

Drugs generally diffuse relatively rapidly from hydrated polymers. More avid drug sequestration is required to prolong drug release, but solving this engineering problem is very difficult. Each drug must be empirically matched to a polymer with a specific set of physicochemical properties. The polymer must not induce a macrophage-mediated foreign body reaction, and it must be non-immunogenic and chemically inert. Despite these constraints, a few products have been created (Dang, et al. (1996) *Pharm. Res.* 13:683–691). Gliadel® wafers (Guilford Pharmaceuticals) are used to deliver the alkylating agent bichloronitrosourea (BCNU) to brain tumors. After surgical resection of aggressive glioblastoma multiforme tumors, wafers are inserted into the cavity as a local adjuvant chemotherapy. Gliadel® wafers are comprised of a proprietary polymer impregnated with BCNU, which is released locally into peritumoral cerebral tissues for months after surgery. This method of dosing is crude, and unfortunately, Gliadel® doesn't prolong survival more than a few months.

Hydrogels and other Polymers that Retard Drug Diffusion

Another strategy to localize drugs is to inject tissues with a polymer, such as a gel, soaked in a solution of the drug (Samuelov Y. et al. (1979) *J. Pharm. Sci.* 68:325–329; Graham, N. B. (1984) *Biomaterials* 5:27–36; Roorda, W. E. et al. (1986) *Pharm Week [Sci]* 8:165–189; Kaleta-Michaels, S. J. et al. (1994) *Proc. Ann. Meet. Am. Assoc. Cancer Res.* 35:A2473; Hnatyszyn, H. J. (1994) *PDA J Pharm Sci Technol.* 48:247–254; Nunes, G. L. et al. (1994) *J. Am. Coll. Cardiol.* 23:1578–83). Release of the drug into the surrounding tissue is limited by the viscosity of the gel, which isolates the drug from the interstitial fluid and local capillaries and thus retards diffusion. The rate of drug diffusion out of the gel is largely determined by the physical and biological properties of the gel, for example its hydrophobicity, tensile strength and biodegradability (Park, K. et al. (1993) *Biodegradable Hydrogels for Drug Deliver.* Technomic Publishing Co., Inc. Lancaster, Pa.). Several biological and non-biological gels are in various stages of development, including chimeric recombinant elastin-silk protein (Protein Polymers, Inc), collagen (Matrix Pharmaceuticals, Inc), poly-lactic acid (PLA), poly-glycolic acid, poly($\epsilon$-caprolactone), poly($\beta$-hydroxybutyrate), poly($\beta$-hydroxyvalerate), polydioxanone, poly(ethylene terephthalate), poly(malic acid), poly(tartronic acid), poly (ortho esters), polyanhydrides, polycyanoacrylates, poly (phosphoesters), polyphosphazenes, hyaluronidate, polysulfones, polyacrylamides, polymethacrylate, CarboPol and hydroxyapaptite (Park, K. et al. (1993) In most cases, the rate of drug release can be controlled by altering the gel's water swelling capacity, tensile strength and rate of biodegradation—properties that can be adjusted by various chemical manipulations.

Biodegradable Hydrogels with Pendant Chains Covalently Coupled to Drugs

Controlled release from the above mentioned drug delivery systems is achieved by manipulating the physicochemical and biological properties of a polymer that is separate from the pharmacologically active drug molecule. Small drug molecules diffuse relatively rapidly through such hydrated polymers, thereby markedly limiting the duration of drug release. To address this shortcoming, investigators have sought to produce controlled release bioactive polymer systems comprised of biodegradable polymers covalently coupled to pharmacologically active drug molecules (reviewed in Bioactive Polymeric Systems (1985) Gebelein, G. C. and Carraher, C. E. Editors. Plenum Press, New York, N.Y.). Bioactive polymers have been synthesized by coupling pharmacologically active drugs to pendant chains via amide bonds or via more labile carbonyl ester linkages. Activation and release of the drugs requires hydrolysis of the amide or carbonyl ester bonds, and such hydrolytic reactions must occur at a rate that is slower than the rate of degradation of the biocompatible macromolecular support (i.e., the "backbone"). Drugs have been attached to a variety of polymeric "backbones", including starch microparticles (Laakso, T. et al. (1987) *J. Pharm. Sci.* 76: 134–140; Stjarnkvist, P. et al. (1991) *J. Pharm. Sci.* 80:436–440); poly(2-hydroxypropyl) methacrylamide copolymers (Duncan, R. et al. (1990) *Biochem. Biophys. Res. Comm.* 94: 284–290); poly-D-lysine (Shen, W-C et al. (1985) *J. Biol. Chem.* 260:10905–10908); and poly-N-(3-hydroxypropyl)-L-glutamine/leucine copolymers (Negishi, N. et al. (1987) *Pharmaceutical Res.* 4:305–310). Bioactive polymers wherein amide bonds link the drug to the pendant chain hydrolyze very slowly and they are relatively stable in serum and tissue fluids (Kopecik, J. (1984) *Biomaterials*, 5:19–25; Rejmanova et al. (1985) *Biomaterials* 6: 45–48). Typically, amide linked drugs are not efficiently released from the pendant chains or backbone unless the polymer is first engulfed by phagocytic cells, wherein the amide bonds are degraded in lysosomes. Drugs such as the narcotic naltrexone linked to poly-N-(3-hydroxypropyl)-L-glutamine/leucine copolymers via relatively labile carbonyl ester bonds are released at a nearly constant rate in vitro. The above mentioned examples are prodrugs whose activation requires hydrolysis of covalent bonds. While the amide and carbonyl ester bonds have succeeded in prolonging the duration of drug release, they have not provided a great deal of control over the rate of drug release, either because their rates of hydrolysis have been too stable (amide bonds) or too unpredictable (ester bonds).

Topical Drug Delivery

Topical drug therapy is used extensively for dermatological and ophthalmological applications (Wepierre, J. and Mary, J-P (1979) *Trends in Pharm. Sci.* 1:23–26; Guzzo, C. et al. (1996) *Dermatological Pharmacology*, In: Goodman and Gilman's The Pharmacological Basis of Therapeutics, 9$^{th}$ Edition. Hardman, Limbird, Molinoff, Ruddon and Gilman, Eds., McGraw-Hill, USA pp.1593–1616.). Scores of topical drugs are available, including corticosteroids, retinoids, vitamin $D_3$ analogs, anti-virals, anti-fungals, anti-bacterials, cytotoxic agents, antihistamines, analgesics and anesthetics. Most of the drugs are inexpensive and the applications are usually frequent. Topical delivery easily provides a constant rate of drug release for at least 24 hours (Transdermal Delivery of Drugs: Proceedings of the Workshop on Current Strategies and Future Directions. Washington D.C. U.S. Department of Health and Human Services. The National Institutes of Health. Higuchi, W. I. and Sharma D. editors).

Nevertheless, topical therapy has significant problems. Excessive application of topically administered retinoids, cholecalciferols and corticosteroids can lead to serious systemic side effects, because they diffuse rapidly into dermal capillaries. Drugs are absorbed more rapidly into the dermal capillaries of diseased skin, which may have reduced barrier function (Wepierre, J. supra). For example, psoriatic and eczematous skin lesions are much more permeable to topically applied drugs than normal skin.

Therapeutic levels of topically applied drugs may be difficult to achieve, because there is no mechanism to retain drugs in the skin after they have penetrated the stratum corneum, the principle barrier function of the skin. Drugs are absorbed into the dermal capillaries at a rate that far exceeds the rate of penetration through the stratum corneum. Consequently, it is exceedingly difficult to create a drug reservoir within the dermis and lower layers of the epidermis. Topical therapy on mucosal surfaces is ineffective, because some drugs are immediately absorbed into the submucosal capillaries. In addition, mucosal surfaces are easily desquamated and they are continuously cleansed with secretions. The lack of a sustained release mechanism limits the dose of many topical drugs, especially potent nonpolar agents. In addition, many drugs—especially macromolecular drugs—do not penetrate cornified layers of the epidermis, thereby precluding their use as topical agents. The topical route of administration cannot guarantee efficacious local drug concentrations.

Lipid-Based Drug Delivery

Lipid bilayer vesicles are closed, fluid-filled microscopic spheres which are formed principally from individual molecules having polar (hydrophilic) and non-polar (lipophilic) portions. (New, R. R. C. (1989) *Preparation of Liposomes*. In: Liposomes-a Practical Approach., IRL Press at Oxford University pp.33–104; Fielding, R. M. (1991) *Clin Pharmacokinetics* 21155–64; Gregoriadis, G. (1973) *FEBS Lett.* 36:292–296). The hydrophilic portions may comprise phosphato, glycerylphosphato, carboxy, sulfato, amino, hydroxy, choline or other polar groups. Examples of lipophilic groups are saturated or unsaturated hydrocarbons such as alkyl, alkenyl or other lipid groups. Sterols (e.g., cholesterol) and other pharmaceutically acceptable adjuvants (including anti-oxidants such as alpha-tocopherol) may also be included to improve vesicle stability or confer other desirable characteristics.

Liposomes are a subset of these bilayer vesicles and are comprised principally of phospholipid molecules that contain two hydrophobic tails consisting of fatty acid chains. Upon exposure to water, these molecules spontaneously align to form spherical, bilayer membranes with the lipophilic ends of the molecules in each layer associated in the center of the membrane and the opposing polar ends forming the respective inner and outer surface of the bilayer membrane(s). Thus, each side of the membrane presents a hydrophilic surface while the interior of the membrane comprises a lipophilic medium. These membranes may be arranged in a series of concentric, spherical membranes separated by thin strata of water, in a manner not dissimilar to the layers of an onion, around an internal aqueous space. These multilamellar vesicles (MLV) can be converted into Unilamellar Vesicles (UV) with the application of a shearing force.

The therapeutic use of liposomes includes the delivery of drugs which are normally toxic in the free form. In the liposomal form, the toxic drug is occluded, and may be directed away from the tissues sensitive to the drug and targeted to selected areas. Liposomes can also be used therapeutically to release drugs over a prolonged period of time, reducing the frequency of administration. In addition, liposomes can provide a method for forming aqueous dispersions of hydrophobic or amphiphilic drugs, which are normally unsuitable for intravenous delivery.

Amphiphilic and hydrophilic drug molecules are generally more efficiently encapsulated into liposomes than non-polar lipophilic drugs. Furthermore, certain non-polar lipophilic drugs and hydrophilic drugs tend to diffuse more rapidly out of liposomes in vivo compared to certain amphiphilic drugs, which may be firmly inserted into the lipid bilayer of the liposome.

In order for many drugs and imaging agents to have therapeutic or diagnostic potential, it is necessary for them to be delivered to the proper location in the body, and the liposome can thus be readily injected and form the basis for sustained release and drug delivery to specific cell types, or parts of the body. Several techniques can be employed to use liposomes to target encapsulated drugs to selected host tissues, and away from sensitive tissues. These techniques include manipulating the size of the liposomes, their net surface charge, and their route of administration. MLVs, primarily because they are relatively large, are usually rapidly taken up by the reticuloendothelial system (principally the liver and spleen). UVs, on the other hand, have been found to exhibit increased circulation times, decreased clearance rates and greater biodistribution relative to MLVs.

Passive delivery of liposomes involves the use of various routes of administration, e.g., intravenous, subcutaneous, intramuscular and topical. Each route produces differences in localization of the liposomes. Two common methods used in attempting to direct liposomes actively to selected target areas involve attachment of either antibodies or specific receptor ligands to the surface of the liposomes. Antibodies are known to have a high specificity for their corresponding antigen and have been attached to the surface of liposomes, but the results have been less than successful in many instances. Some efforts, however, have been successful in targeting liposomes to tumors without the use of antibodies (see, for example, U.S. Pat. No. 5,019,369). U.S. patent application Ser. No. 08/434,465, filed May 4, 1995, entitled "Nucleic Acid Ligand Complexes" (specifically incorporated herein by reference), describes nucleic acid ligands attached to the surface of liposomes which may be used as an alternative to antibodies for targeting purposes.

An area of development aggressively pursued by researchers is the delivery of agents not only to a specific cell type but into the cell's cytoplasm and, further yet, into the nucleus (Ledley F. D. (1995) *Human Gene Therapy* 6:1129–44). This is particularly important for the delivery of biological agents such as DNA, RNA, ribozymes and certain proteins. A promising therapeutic pursuit in this area involves the use of antisense DNA and RNA oligonucleotides for the treatment of disease. However, one major problem encountered in the effective application of antisense technology is that oligonucleotides in their phosphodiester form can be quickly degraded in body fluids and by intracellular and extracellular enzymes, such as endonucleases and exonucleases, before the target cell is reached. Intravenous administration can also result in rapid clearance from the bloodstream by the kidney, and uptake is generally insufficient to produce an effective intracellular drug concentration. Liposome encapsulation protects the oligonucleotides from the degradative enzymes, increases the circulation half-life and increases uptake efficiency as a result of phagocytosis of the liposomes. In this way, oligonucleotides are able to reach their desired target and to be delivered to cells in vivo.

Antisense Oligonucleotides Conjugated to Lipids

Lipids have been used in other ways to improve the delivery of antisense nucleic acid oligomers. PCT Publication No. WO 90/10448 (Bischofberger) describes a conjugate comprising a lipid component covalently coupled to an antisense oligonucleotide. The lipid component provides a means for allowing the antisense oligonucleotide to cross cell membranes. Release of the antisense oligonucleotide from the lipid requires hydrolysis by cellular enzymes of the phosphodiester bonds (s) joining the lipid to the therapeutic oligonucleotide. Liposomes are also mentioned as a method for delivering the lipid-antisense oligonucleotides.

Lipid-Based Prodrugs Activated by Hydrolysis of Phosphodiester Bonds

A method of improving the intestinal absorption of drugs that are not orally bioavailable in a non-derivatized state is described in U.S. Pat. Nos. 5,411,947 and 5,484,809 (Hostetler). The oral delivery of these drugs is facilitated by converting drugs having suitable functional groups to 1-O-alkyl-, 1-O-acyl-, 1-S-acyl-and 1-S-alkyl-sn-glycero-3-phosphate derivatives. The active drug is released from the lipid prodrug by phospholipases that cleave the phosphoester bond linking the drug to the lipid.

U.S. Pat. No. 5,554,728 (Basava) describes peptide-lipid conjugates having increased plasma half-lives comprising therapeutic peptides covalently linked to lipids through linkers such as amino acids having hydroxyl functional groups.

U.S. Pat. No. 5,223,263 (Hostetler) describes lipid derivatives of nucleoside analogs which can be incorporated into liposomes. The lipid component allows the nucleoside analogs to be efficiently loaded and retained in liposomes and influences the biodistribution and pharmacokinetics of the nucleoside analogs. These derivatives are converted into active nucleoside analogs by constituent cellular metabolic processes.

U.S. Pat. No. 5,463,092 (Hostetler) describes phosphonoacids—such as phosphonoformate (foscarnet)—having antiviral activity which are linked, either through a phosphate group or a carboxyl group of the phosphonic acid, to a lipid.

U.S. Pat. No. 5,614,503 (Chaudhary) describes an amphipathic nucleic acid transporter to deliver nucleic acids into cells, comprising a cationic compound having a cationic head group for binding the nucleic acid and a lipid tail for association with the cell membrane.

Simple Phosphoester-Based Prodrugs Activated by Phosphatases

The aqueous solubility of drugs may be increased by esterifying hydroxyl groups with negatively charged phosphates, which are removed by serum phosphatase(s), thereby activating the drug. These agents are herein referred to as simple phosphoester-based prodrugs, because favorable properties of such prodrugs are contributed by a phosphate. For example, the monophosphate derivative of the nucleoside fludarabine (9-β-D-arabinofuranosyl-3-fluoroadenine) (Chun H. G. et al. (1991) *J. Clin. Oncol.* 9:175–188) is more soluble in aqueous solutions than the non-phosphorylated fludarabine nucleoside. Intravenously administered fludarabine monophospate nucleotide is rapidly dephosphorylated in vivo by membrane 5'-ectonucleotidases; the resulting nucleoside is transported into the cell where it is rephosphorylated into the triphosphate derivative, which disrupts cellular nucleic acid metabolism.

Simple phosphoester prodrugs have also been created to improve the solubility properties and pharmacological properties of systemically administered non-nucleoside drugs. The oncolytic drug Etoposide® is a poorly soluble topoisomerase II inhibitor that must be formulated in polysorbate, polyethylene glycol and ethanol excipients (Doyle. T. W. and Vyas, D. M. (1990) *Cancer Treat. Rev.* 17:127–131; Schacter, L. P. et al. (1994) *Cancer Chemother. Pharmacol.* 34 (Suppl-S58–S63). To administer Etoposide® intravenously, the stock drug must be diluted to 0.2–0.4 mg/mL and infused over 30–60 minutes. This restriction is more than an inconvenience, because effective bolus IV doses cannot be used to treat cancer patients. To improve the aqueous solubility of Etoposide®, the hydroxyl group on the phenyl ring is phosphorylated to create etoposide phosphate (Etopophos®). Five minutes after Etopophos® is intravenously administered, the phosphate is quantitatively removed by serum alkaline phosphatase, thereby activating the drug and allowing IV bolus dosing.

In other cases of phosphoester prodrugs, however, phosphoester hydrolysis is not nearly as efficient as in the above mentioned examples. For example, water soluble 2'- and 7'-taxol phosphates are poor substrates for alkaline phosphatase activity (Vyas et al., (1993) *Bioorganic and Med. Chem. Lett.* 3:1357–1360; Ueda, Y. et al. (1995) *Bioorganic and Med. Chem. Lett.* 5:247–252).

Covalent Cleavage (Release) of Drugs from Chemical Modifiers as a Method of Enhancing Iontophoretic Drug Delivery Prodrugs with improved properties for iontophoretic delivery have been described in U.S. Pat. No. 5,607,691 (Hale) which describes methods of delivering pharmaceutical agents across the skin layer or mucosal membranes of a patient. In this method, a pharmaceutical agent is covalently bonded to a chemical modifier, via a covalent physiologically cleavable bond. The chemical modifier comprises either permanently charged organic compounds or organic compounds which carry an ionic charge by virtue of the conditions of pH which exist transmembrane during transdermal delivery. The chemical modifiers function to alter the charge characteristics of a pharmaceutical agent in order to enhance membrane transport. The chemical modifier is cleaved from the pharmaceutical agent by a physiological process, thereby releasing the activated drug into the tissues.

The SELEX Process

A method for the in vitro evolution of nucleic acid molecules with highly specific binding to target molecules has been developed. This method, Systematic Evolution of Ligands by EXponential enrichment, termed the SELEX process, is described in U.S. patent application Ser. No. 07/536,428, filed Jun. 11, 1990, entitled "Systematic Evolution of Ligands by Exponential Enrichment", now abandoned; U.S. patent application Ser. No. 07/714,131, filed Jun. 10, 1991, entitled "Nucleic Acid Ligands", now U.S. Pat. No. 5,475,096; U.S. patent application Ser. No. 07/931,473, filed Aug. 17, 1992, entitled "Methods for Identifying Nucleic Acid Ligands", now U.S. Pat. No. 5,270,163 (see also WO 91/19813), each of which is specifically incorporated by reference herein. Each of these applications, collectively referred to herein as the SELEX Patent Applications, describes a fundamentally novel method for identifying nucleic acid ligands to virtually any desired target molecule. The SELEX process provides a class of products which are referred to as nucleic acid ligands (also referred to in the art as "aptamers"), each ligand having a unique sequence, and which has the property of binding specifically to a desired target compound or molecule. Each SELEX-identified nucleic acid ligand is a specific ligand of a given target compound or molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure", abandoned in favor of U.S. patent application Ser. No. 08/198,670, now U.S. Pat. No. 5,707,796, describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands", describes a SELEX based method, termed PhotoSELEX, for selecting nucleic acid ligands containing photoreactive groups capable of binding and/or photocrosslinking and/or photoinactivating a target molecule. In one embodiment of the PhotoSELEX method, the photocrosslinkable ligand may be introduced into a patient in a number of ways known in the art. For example, the photocrosslinkable nucleic acid ligand may be delivered to the patient by intravenous injection of a solution or a lipid-based formulation (e.g., liposomes), by intralesional injection, by passive topical application, by iontophoresis or by other routes of administration. The ligand is then covalently crosslinked to the target molecules using irradiation, including visible, 325 nm, X-ray, ultraviolet and infrared light. Irradiation may be applied in vivo or ex vivo. High yield photocrosslinking occurs between the photoreactive bases juxtaposed to tyrosine, tryptophan, histidine and cystine residues within protein target molecules as demonstrated previously in many systems (Weintraub, H. (1973) *Cold Spring Harbor Symp. Quant. Biol.* 38:247; Lin and Riggs (1974) *Proc. Natl. Acad. Sci. USA* 71:947; Ogata and Gilbert (1977) *Proc. Natl. Acad. Sci. USA* 74:4973; Barbier et al. (1984) *Biochemistry* 23:2933; Wick and Matthews (1991) *J. Biol. Chem.* 266:6106; Khalili et al. (1988) *EMBO J.* 7:1205; Gott et al. (1991) *Biochemistry* 30:6290; Favre (1990) *Bioorganic Photochemistry,* Volume 1: Photochemistry and the Nucleic Acids. (H. Morrison, ed.) John Wiley and Sons., New York, pp.379–425; Evans et al. (1989) *Biochemistry* 28:713; Farrar et al. (1991) *Biochemistry* 30:3075; Wower et al. (1989) *Biochemistry* 28:1563; Liu and Verdine (1992) *Tetrahedron Letters* 33:4265; Chen and Prusoff.(1977) *Biochemistry* 16:3310).

U.S. patent application Ser. No. 08/134,028, filed Oct. 7, 1993, entitled "High-Affinity Nucleic Acid Ligands That Discriminate Between Theophylline and Caffeine," abandoned in favor of U.S. patent application Ser. No. 08/443,957 filed May 18, 1995, now U.S. Pat. No. 5,580,737, describes a method for identifying highly specific nucleic acid ligands able to discriminate between closely related molecules, which can be non-peptidic, termed Counter-SELEX. U.S. patent application Ser. No. 08/143,564, filed Oct. 25, 1993, entitled "Systematic Evolution of Ligands by Exponential Enrichment: Solution SELEX," abandoned in favor of U.S. Pat. No. 5,567,588, describes a SELEX-based method which achieves highly efficient partitioning between oligonucleotides having high and low affinity for a target molecule. U.S. patent application Ser. No. 07/964,624, filed Oct. 21, 1992, entitled "Nucleic Acid Ligands to HIV-RT and HIV-1 Rev", now U.S. Pat. No. 5,496,938, describes methods for obtaining improved nucleic acid ligands after the SELEX process has been performed. U.S. patent application Ser. No. 08/400,440, filed Mar. 8, 1995, entitled "Systematic Evolution of Ligands by EXponential Enrichment: Chemi-SELEX", now U.S. Pat. No. 5,705,337, describes methods for covalently linking a ligand to its target. U.S. patent application Ser. No. 08/434,425, filed May 3, 1995, entitled "Systematic Evolution of Ligands by EXponential Enrichment: Tissue SELEX", now U.S. Pat. No. 5,789,157 describes a method for identifying nucleic acid ligands to tissues.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides", abandoned in favor of U.S. patent application Ser. No. 08/430,709 filed Apr. 27, 1995, now U.S. Pat. No. 5,660,985, that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2'-Modified Nucleosides by Intramolecular Nucleophilic Displacement", describes oligonucleotides containing various 2'-modified pyrimidines. U.S. application Ser. No. 08/442,062, filed May 16, 1995, entitled "Methods of Producing Nucleic Acid Ligands", now U.S. Pat. No. 5,595,877, describes methods for identifying and designing improved nucleic acid ligands identified by the SELEX process.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX", now U.S. Pat. No. 5,637,459, and U.S. patent application Ser. No. 08/234,997, filed Apr. 28, 1994, entitled "Systematic Evolution of Ligands by Exponential Enrichment: Blended SELEX,", now U.S. Pat. No. 5,683,867, respectively. These applications allow the combination of the broad array of shapes and other properties, and the efficient amplification and replication properties, of oligonucleotides with the desirable properties of other molecules.

The SELEX method further encompasses combining selected nucleic acid ligands with lipophilic compounds of non-immunogenic, high molecular weight compounds in a diagnostic or therapeutic complex as described in U.S. patent application Ser. No. 08/434,465, filed May 4, 1995, entitled "Nucleic Acid Ligand Complexes". Each of the above described patent applications, which describe the basic SELEX method and modifications of the basic SELEX method, are specifically incorporated by reference herein in their entirety.

Photochemotherapy to Trap Drugs in the Tissues

The most widely used form of photochemotherapy is psoralin-ultraviolet A (PUVA;) (Guzzo, C. et al., supra; Gonzalez, E. (1995) (1996) *Dermatol Clin.* 13:851–866). This method covalently fixes photoreactive psoralins to macromolecules within cells of the superficial dermis and epidermis. Psoralins easily penetrate all cells, and when activated by ultraviolet light ($\lambda$=320 to 400 nm) they bind covalently to DNA and other molecules inside of cells. Psoralins eventually escape from cells that are not exposed to UVA, so this method has been used to 'trap' the drug specifically in the skin. Psoralins intercalate into DNA, and the majority of crosslinked products are psoralin-DNA adducts. Not surprisingly, psoralin adducts eventually overwhelm the nucleotide excision repair system that normally removes such lesions. Current evidence indicates that DNA crosslinking causes cell cycle arrest and/or apoptosis in proliferating cells, such as basal keratinocytes and lymphocytes, but more complex (cytokine mediated) effects are undoubtedly involved. DNA adducts have been found in keratinocytes, lymphocytes, dermal fibroblasts and Langerhans cells.

PUVA is approved for the treatment of cutaneous T-cell lymphoma (CTCL), psoriasis, lichen planus, atopic dermatitis, vitiligo, alopecia areata and cutaneous photosensitivity syndromes. In every case, the skin is characterized by abnormal lymphocytic infiltrates. CTCL is a neoplastic disease, whereas the others are immunoregulatory disorders. It remains unclear why these diseases respond to such a nonspecific therapy.

Many serious toxicities are associated with PUVA therapy (Wolff. K. (1990) *Br. J. Dermatol.* 122 Suppl 36:117–25; Young, A. R. (1990) *J. Photochem. Photobiol. B.* 6:237–47; Gonzalez, E. supra; Stern et al., (1997) *New Eng. J. Med.* 336:1041–1045). First, there is a ten-fold increase in squamous cell carcinoma and there is a significant increase in melanoma. Second, some patients suffer from burns, blisters, photoallergies and painful eythematous patches. Chronic treatment leads to mottled pigmentation and actinic skin damage. Finally, patients taking oral methoxsalen are at risk for developing cataracts, because methoxsalen penetrates the lens, where it may be crosslinked to crystalin proteins.

Photodynamic therapies (PDTs) have been developed to treat cancers of the bladder wall and a variety of malignant and benign skin conditions (Lui, H. et al. (1993) *Dermatologic Clinics* 11:1–13). PDTs utilize photoreactive porphyrin derivatives and dipyrroles, photoactivators that transfer their light energy to singlet oxygen, which damages cellular membranes and activates stress response pathways, some of which induce apoptosis. Unlike PUVA, the photoreactive drugs are not covalently crosslinked to cellular macromolecules.

Extracorporeal Photopheresis to Crosslink Drugs to Cells

An extracorporeal version of PUVA has been developed for the treatment of cutaneous T-Cell lymphoma (Edelson, R. et al. (1987) *N. Engl. J. Med.* 316:297–303). The therapeutic index of PUVA can be increased if the malignant T-cells are treated with UVA outside of the body. First, the patient is administered oral methoxsalen. Next, a semipure population of malignant cells is removed under sterile conditions by leukapheresis and are exposed to UVA. The cells are returned to the body, where many succumb to PUVA's toxic DNA crosslinking effects, but it has been postulated that an active immunization phenomenon may also contribute to the therapeutic effects. However, the underlying mechanism of photopheresis remains poorly understood. Photopheresis is most effective in CTCL patients who have a significant leukemic component (e.g., Sezary Cells).

Clearly, it would be useful to have more effective methods of concentrating drugs in diseased tissue compartments. Systemic toxicities of many potent drugs would be minimized or eliminated by providing sustained release of the drug from a tissue reservoir located within or immediately adjacent to the diseased tissue compartment, and by markedly reducing the volume of drug distribution. It would also be useful to have a local delivery method whereby active drugs are gradually released from tissue reservoirs and which do not displace normal tissue structures. For example, a new technology that provides for the gradual release of drugs at the dermo-epidermal junction would bypass the cornified layers at the surface of the skin, which comprises the major rate limiting barrier to diffusion of topically administered drugs. Furthermore, tissue-anchoring and sustained release of drugs into a small volume within the sub-epithelial dermis would minimize the rapid diffusion and absorption problems that limit the usefulness of current topical drug delivery methods, such as passive diffusion and iontophoresis. Finally, a powerful and versatile sustained drug release technology would utilize known chemistry for the release of the active drug and for the manipulation of the rate of the chemical reaction controlling drug release and activation.

The use of nucleic acid polymers as a component of a prodrug in which the nucleic acid polymer simultaneously provides a means of targeting and/or anchoring the prodrug to the target and provides a mechanism for sustained release of the active drug component has not been taught in the prior art. The present invention demonstrates that nucleotide-based prodrugs possess numerous advantages over current drug delivery systems.

SUMMARY OF THE INVENTION

The present invention provides novel nucleotide-based prodrugs comprising a nucleotide component covalently bonded to a drug component via a junctional ester bond. In one embodiment, the junctional ester bond is a physiological hydrolyzable ester bond. The present invention exploits the ability to control the rate of hydrolysis of this junctional ester bond as a means of providing a controlled sustained release of the active form of the drug.

The nucleotide component of the nucleotide-based prodrugs of the present invention provides the novel and versatile properties of targeting and/or anchoring the nucleotide-based prodrug in the immediate vicinity of the target (i.e., the desired site for therapy) and providing for sustained release of the pharmacologiclly active form of the drug component. Release of the active drug arises from hydrolysis of a junctional ester bond which joins the active drug component to the nucleotide component of the nucleotide-based prodrug. The present invention is based on the unique insight that the rate of release and activation of the drug can be manipulated by chemically altering the nuclease resistance of the nucleotide component of the nucleotide-based prodrug and/or chemically altering the nuclease resistance of the junctional ester bond joining the drug to a nucleotide component. Increasing the nuclease resistance of the nucleotide component will in turn decrease the rate of release of the active drug component of the nucleotide-based prodrug. In this way, versatile sustained release properties can be bestowed upon nucleotide-based prodrugs.

The ability to manipulate of the rate of hydrolysis of ester bonds in the nucleotide component is significant in that it distinguishes the nucleotide-based prodrugs of the present invention from other classes of prodrugs. Unmodified oligonucleotides are rapidly degraded in vivo by tissue nucleases and esterases. However, methods are known for modifying nucleotides to make them more resistant to degradation in vivo. The inventors have exploited these methods to develop novel nucleotide-based prodrugs, wherein the release and activation of a drug component can be prolonged by strategically modifying the nucleotide component of the nucleotide-based prodrug. A variety of chemical modifications which will increase the nuclease resistance of nucleotide components are known in the art. In one embodiment of the invention, nucleotide residues in the nucleotide component are modified at the 2'-position of the sugar moiety in order to make the nucleotide component more resistant to nucleases, phosphodiesterases and other esterase activities in vivo. In other embodiments of the present invention, the rate of hydrolysis of the nucleotide component can be markedly prolonged by modifying the phosphodiester backbone of the nucleotide component. Such modifications will confer stability upon the junctional ester bond which joins the active drug component to the nucleotide component of the nucleotide-based prodrug.

The anchoring and sustained release properties of the nucleotide-based prodrugs of the present invention have the additional benefits of allowing for a high, local concentration of the drug at or near a desired target. Thus, after administration of the nucleotide-based prodrug the nucleotide component is gradually hydrolyzed by nucleases and/or other phosphodiesterases in the tissue and the active drug component is released in the vicinity of the target. This establishes a desirable drug gradient (see, for example, FIG. 3). Furthermore, since the nucleotide-based prodrug is anchored at or near the desired target, the diffusion distance of the active drug component to the target is minimized once the drug has been liberated from its prodrug form. As a result, the active drug is delivered directly to the desired target, resulting in reduced systemic toxicity. Therefore, the nucleotide-based prodrug of the present invention allows exposure of the target to a high, local concentration of a drug over an extended period of time, thus reducing both the size and frequency of doses of the drug necessary for effective treatment, providing for a wide therapeutic index and providing for a more effective therapy. Thus, the nucleotide-based prodrugs of the present invention overcome the inherent shortcomings of current drug delivery systems—such as rapid diffusion, rapid absorption of drugs and systemic toxicity—by providing a unique method of targeting and/or anchoring the nucleotide-based prodrug at or in the vicinity of the target.

In certain embodiments of the present invention, local delivery of the nucleotide-based prodrugs and sustained release of active drug components are achieved without excipients, resins or gels, so there is virtually no tissue displacement upon administration of the nucleotide-based prodrug.

In certain embodiments, the nucleotide component of the nucleotide-based prodrugs comprises a nucleic acid ligand (aptamer) which performs a dual function of targeting and anchoring the nucleotide-based prodrug to a desired target by virtue of aptamer-specific binding to the target. Examples of this embodiment are illustrated in FIGS. 1B–H. In a preferred embodiment, the nucleic acid ligand is identified by the SELEX process, and the nucleic acid ligand binds the nucleotide-based prodrug to macromolecules such as proteins in a diseased tissue. Thus the nucleotide-based prodrugs in this embodiment are distinguished from other prodrugs in that the present nucleotide-based prodrugs precisely target the therapy.

In another embodiment, the nucleotide-based prodrug is anchored at or in the vicinity of the desired target by incorporating photoreactive nucleotides into the nucleotide component. In this embodiment, the nucleotide-based prodrug is administered locally, and the site of administration is exposed to UV light, which induces photocrosslinking between a target, for example a protein in a tissue, and the photoreactive nucleotides. Examples of this embodiment are illustrated in FIGS. 2D–F.

In other embodiments, nucleotide-based prodrugs are sequestered in discrete tissue sites by virtue of the covalent attachment of the nucleotide component to a poorly diffusible macromolecular support (FIGS. 2A–C). In the preferred embodiment, the macromolecular support is a biocompatible polymer.

In the above embodiments, it is necessary that the junctional ester bond coupling the drug component to the nucleotide component of the nucleotide-based prodrug is able to be hydrolyzed in vivo.

In another embodiment, the nucleotide-based prodrug comprises radioactive nucleotides as the drug component. In this embodiment, it may be desirable to prevent junctional ester bond hydrolysis and therefore prevent release of the radioactive nucleotides in order to avoid toxicity of certain tissues.

The invention further includes nucleotide-based prodrugs with amphiphilic properties. These nucleotide-based prodrugs comprise pharmacologically active, non-polar lipids, such as retinoids, vitamin D analogs, eicosanoids, steroids or ceramide analogs covalently bonded to one or more nucleotide components via junctional ester bonds (FIG. 24). Hydrolysis of the junctional ester bonds in vivo releases either the active lipid compound or a monophosphorylated derivative of the active lipid compound that is subsequently activated by tissue phosphatases. In one embodiment, the amphiliphilic nucleotide-based prodrug is administered in a lipid vehicle comprised of a lipid bilayer vesicle, preferably a liposome.

In embodiments wherein the pharmacologically active prodrug component of the nucleotide-based prodrug is covalently bonded to more than one nucleotide component, the release of the drug will be prolonged even further since release of the drug will require the hydrolysis of more than one junctional ester bond.

The present invention also includes methods for treating diseases in humans and animals by administering pharmaceutically effective amounts of a nucleotide-based prodrug. Nucleic acid prodrugs are administered by methods known in the art. In embodiments wherein the nucleotide-based prodrug contains a nucleic acid ligand component or wherein the nucleotide-based prodrug is in a lipid bilayer vesicle, the nucleotide-based prodrug may be administered systemically or locally. In embodiments wherein the nucleotide-based prodrug comprises a non-aptameric nucleotide component comprising one or more photoreactive bases—or where the non-aptameric nucleotide component is covalently bonded to a poorly diffusible macromolecular support—the nucleotide-based prodrug is administered, for example, at the site of the diseased tissue, and the site of application is exposed to UV light to induce covalent bond formation between the photoreactive bases with the desired target.

BRIEF DESCRIPTION OF THE FIGURES

FIG. 1 illustrates a schematic nucleic acid ligand (1A), and several examples of nucleotide-based prodrug embodiments, including: (1B) nucleotide-based prodrugs comprising a nucleic acid ligand component and pharmacologically active nucleoside analogs incorporated into the nucleotide component via junctional phosphodiester bonds; (1C) nucleotide-based prodrugs comprising a nucleic acid ligand component and radioactive nucleoside analogs incorporated into the nucleotide component via junctional phosphodiester bonds; (1D) nucleotide-based prodrugs containing pharmacologically active nucleoside analogs and photocrosslinkable nucleotides incorporated into a nucleic acid ligand; (1E) nucleotide-based prodrugs comprising pharmacologically active non-nucleoside drug compounds bonded via a junctional phosphodiester bond to nucleic acid ligands; (1F) nucleotide-based prodrugs comprising pharmacologically active non-nucleoside drug compound coupled via a junctional carbonyl ester bond to a nucleic acid ligand; (1G) nucleotide-based prodrugs comprising pharmacologically active non-nucleoside drugs bonded via a junctional phosphodiester bond through an adapter molecule to a nucleic acid ligand; and (1H) nucleotide-based prodrugs comprising pharmacologically active non-nucleoside drugs bonded via a junctional carbonyl ester bond via an adapter molecule.

FIG. 2 illustrates examples of non-aptameric nucleotide-based prodrugs. FIG. 2A shows nucleotide-based prodrugs comprising pharmacologically active nucleoside analogs bonded to nucleotide components which lack ligand binding properties. These prodrugs are attached to a macromolecule that prevents diffusion of the prodrug after it is administered into tissues. FIG. 2B shows a nucleotide-based prodrug comprising pharmacologically active non-nucleoside compounds bonded via a junctional phosphodiester bond to nucleotide components without ligand binding properties. FIG. 2C shows nucleotide-based prodrugs comprising pharmacologically active non-nucleoside compounds coupled via a junctional carbonyl ester bond to nucleotide components without ligand binding properties. These prodrugs are attached to a macromolecular support that retards diffusion of the prodrug after it is administered, for example, into tissues. FIG. 2D shows prodrug polymers comprising pharmacologically active nucleoside(s) without ligand binding properties, but with nucleotides comprised of photoreactive bases. FIG. 2E shows nucleotide-based prodrugs comprising pharmacologically active non-nucleoside compounds coupled via a junctional phosphodiester bond to nucleotide components without ligand binding properties. These prodrugs are attached to the desired target via photochemical crosslinking reactions to retard diffusion of the prodrug. FIG. 2F shows nucleotide-based prodrugs comprising pharmacologically active non-nucleoside compounds coupled via a junctional carbonyl ester bond to nucleotide components without ligand binding properties. These prodrug are attached to a desired target via photochemical crosslinking reactions to reduce or eliminate diffusion of the prodrug.

FIGS. 7A–G illustrate examples of photocrosslinkable bases that may be incorporated in nucleotide-based prodrugs.

FIGS. 8A and B illustrate two examples of nucleotide-based prodrugs comprising nucleic acid ligands containing polymeric tails comprised of photocrosslinkable nucleotide 4-thiouridine plus an oncolytic nucleoside analog, 2-deoxycoformycin (8A) or 2'-chlorodeoxyadenosine (cladribine) (8B). The nucleic acid ligand is selected for its ability to bind to macromolecules on the surface of a leukemic cell and the active drug "tail" is added to the nucleic acid ligand as a postSELEX modification.

FIG. 9 illustrates one example of a nucleotide-based prodrug comprising a nucleic acid ligand containing a copolymeric "tail" comprised of photocrosslinkable nucleotides (4-thiouridylic acid) and several copies of the oncolytic nucleoside analog, cytosine arabinoside. The nucleic acid ligand is selected for its ability to bind to macromolecules on the surface of a leukemic cell, and the active drug "tail" is added to the nucleic acid ligand as a postSELEX modification.

FIG. 12A: Rate of drug release and activation is controlled by varying the number of prodrug nucleotide components attached to the poorly diffusible macromolecular support. FIG. 12B: Duration and the rate of drug release is controlled by varying the length of the prodrug nucleotide components attached to the poorly diffusible macromolecular support. FIG. 12C: Pharmacologically active nucleoside analogs may be inserted as contiguous blocks, in this case at the end which is distal to the poorly diffusible macromolecular support. FIG. 12D: Pharmacologically active nucleoside analogs and pharmacologically inactive nucleotides interspersed throughout the nucleotide components. FIG. 12E: Multiple pharmacologically active nucleoside analogs and pharmacologically inactive nucleotides distributed throughout the nucleotide component. FIG. 12F: Blocks of nucleotide components containing one or more active nucleoside analogs interspersed between macromolecular supports.

FIGS. 15A–C illustrate one example of a nucleotide-based prodrug containing multiple pharmacologically active drug molecules, in this case immunosuppressive purine analogs 2'-deoxycoformycin and 6-mercaptopurine. In FIG. 15A, the nucleotide component is attached to a poorly diffusible macromolecular support. Hydrolysis of the nucleotide component releases pharmacologically active nucleoside analogs. FIG. 15B illustrates the pharmacologically active form of 2'-deoxycoformycin released from the prodrug in FIG. 15A. FIG. 15C illustrates thio-inosine monophosphate (TIMP), the pharmacologically active form of 6-mercaptopurine.

FIGS. 18A and B examples of nucleotide-based prodrugs comprised of non-nucleoside drugs coupled to nucleotides via 5' junctional phosphodiester bons (18A), and 3' junctional phosphodiester bonds (18B). A single nucleotide (n=1) or nucleotide components (n>1) may also be coupled to the non-nucleoside drug via the same types of bonds. X is any drug with a hydroxyl group.

FIGS. 28A and 29B illustrate examples of nuclease resistant dinucleotides.

DETAILED DESCRIPTION

Figure 3:
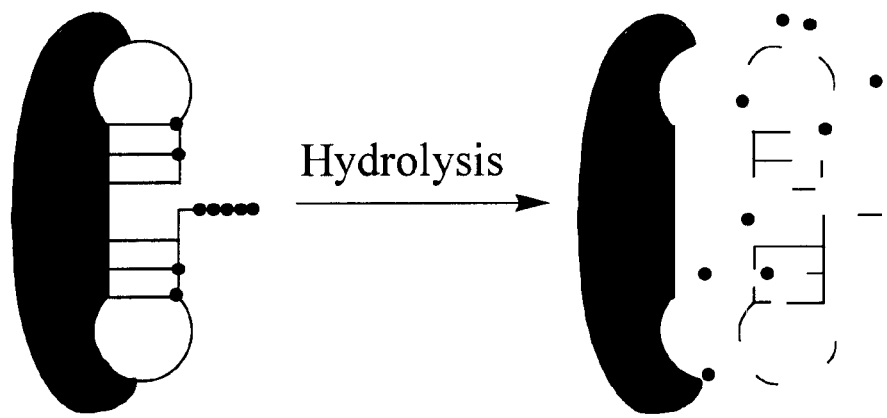
FIG. 3 illustrates sustained release of nucleoside analog drugs from a nucleotide-based prodrug comprising a nucleic acid ligand. The intact prodrug is bound to a target by aptameric binding, thereby providing a reservoir of potentially activatable drug. The pharmacologically active nucleoside analog is released and activated as the nucleic acid ligand is hydrolyzed in vivo by tissue nuclease and/or esterase activities.
Figure 3:
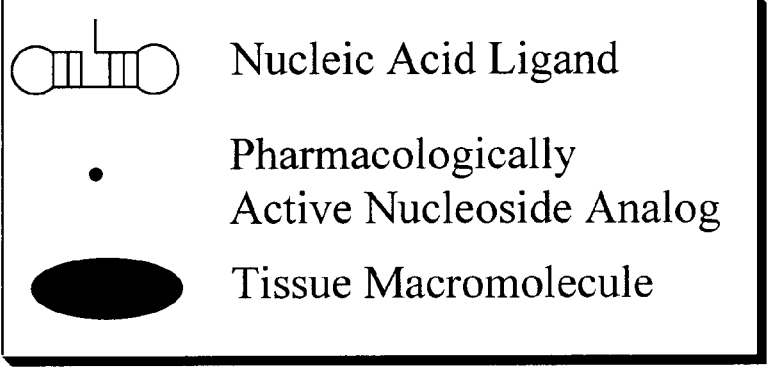

The present invention provides nucleotide-based prodrugs comprising a pharmacologically active drug covalently attached to one or more nucleotide components. The active drug component may be a nucleoside analog, a nucleic acid ligand, or a non-nucleoside drug. The nucleotide component simultaneously provides a means of targeting and/or anchoring the nucleotide-based prodrug to the desired tissue compartment and/or a mechanism of sustained release of the active drug, thereby providing for a more effective drug delivery system with reduced toxicity. The targeting and/or achoring of the nucleotide-based prodrugs to the desired tissue is achieved through using a nucleic acid ligand as the nucleotide component, and/or by incorporating photo-crosslinkable bases into the nucleotide component, and/or by covalently bonding the nucleotide component to a macromolecular support. Any drug having a hydroxyl group capable of forming a phosphodiester bond with the 3' or 5' phosphate group of a nucleotide may be converted into a nucleotide-based prodrug. Further, any drug having a carboxyl group capable of forming a junctional carbonyl ester bond with the 3' or 5' hydroxyl group of a nucleotide may be converted into a nucleotide-based prodrug. Therefore, many therapeutic classes of drugs with diverse chemical structures may be utilized in preparing nucleotide-based prodrugs of the present invention.

For purposes of clarity and a complete understanding of the invention, the following terms are defined.

"Prodrug" is defined herein is a compound that exhibits pharmacological activity after undergoing a chemical transformation in the body.

"Nucleotide-based prodrug" is defined herein as a compound comprising a drug covalently bonded through a junctional ester bond to a nucleotide component. In one embodiment, the nucleotide-based prodrug lacks inherent pharmacological activity. Following cleavage of the junctional bond, the drug is released in a pharmaceutically active form. The covalent bond includes, but is not limited to, a phosphodiester or carbonyl ester bond.

An "ester bond" includes a covalent bond joining two nucleotides. A "junctional ester bond" includes, but it not limited to, a phosphodiester bond or a carbonyl ester bond which covalently joins the pharmacologically active drug component and the nucleotide component of the nucleotide-based prodrug.

A "drug" or "drug component" is any substance used in the prevention, diagnosis, alleviation, treatment or cure of disease. Any drug having a hydroxyl group capable of forming a phosphodiester bond with the 3' or 5' phosphate group of a nucleotide may be converted into a nucleotide-based prodrug. Further, any drug having a carboxyl group capable of forming a junctional carbonyl ester bond with the 3' or 5' hydroxyl group of a nucleotide may be converted into a nucleotide-based prodrug. Drugs which can be attached to an adapter molecule having a free hydroxyl group or carboxyl group may also be converted into nucleotide-based prodrugs, provided that the pharmaceutical activity of the parent drug is not impaired by the adapter molecule or provided that the adapter molecule is removed as a step in the activation of the drug component of the nucleotide-based prodrug in vivo. In this way, polypeptides may be converted into nucleotide-based prodrugs.

Therefore, many therapeutic classes of drugs with diverse chemical structures may be utilized in preparing nucleotide-based prodrugs of the present invention, including but not limited to nucleoside analogs and related antimetabolites, folate antagonists, anthracyclines, vinca alkaloids, taxenes and related microtubule stabilizing agents, epipodophyllatoxins and other topoisomerase II inhibitors, camptothecin and related topoisomerase I inhibitors, aminoglycoside antibiotics, macrolide antibiotics and immunosuppressive agents, cyclic polypeptides, and polyene antibiotics and many other additional natural product-derived drugs. Many examples of drug molecules that may be used to create nucleotide-based prodrugs are listed in Tables 1–8.

The drug component of the nucleotide-based prodrugs also may include any pharmaceutically active nucleoside analog. A host of radioactive nucleotides, including but not limited to, $^{32}$Phosphorus-containing nucleotides and $^{125}$Iodine-containing pyrimidine nucleotides may also be linked to nucleotide components to achieve the desired in vivo therapeutic properties.

The drug component may also be a nucleic acid ligand. In the preferred embodiment, the nucleic acid ligand is identified by the SELEX method.

"Nucleic acid" or "nucleotide" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and functionality to the nucleic acid. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodouracil, backbone modifications, methylations, unusual base-pairing combinations such as the isobases isocytidine and isoguanidine and the like. Modifications can also include 3' and 5' modifications such as capping.

"Nucleoside analogs" of the invention include any nucleoside that does not occur naturally in the species being treated with a nucleotide-based prodrug. In general, the nucleoside analogs of the present invention include nucleosides having a purine or pyrimidine base, e.g., adenine, guanine, cytosine or thymine, or an analog thereof, attached to a pentose, such as ribose or a ribose residue and/or derivative of ribose. Analogs of both the purine and pyrimidine base and the ribose group can differ from a corresponding naturally occurring moiety by having new substituent groups attached thereto, for example, 2,6-diaminopurine or didehydroribose, by having naturally occurring substituent groups deleted therefrom, or by having atoms normally present replaced by others, for example, 8-azaguanine. Nucleoside analogs may also comprise a purine or pyrimidine base attached to the pentose moiety in a non-naturally occurring linkage, such as, for example, through the nitrogen at position 3 rather than the 1 position of the pyrimidines. Nucleoside analogs include structures whereby the nitrogen atom of the nucleic acid base is linked by a β-N-glycosyl linkage to carbon 1 of the pentose ring, and structures whereby the nitrogen atom of the nucleic acid base is linked by an α-N-glycosyl linkage to carbon 1 of the pentose ring. Nucleosides with α-chirality of the N-glycosyl linkage to carbon 1 of the pentose ring are referred to as "α-nucleosides", and are either unusual or not present in nature. The pentose residue may be a complete pentose, or a derivative such as a deoxy- or dideoxypentose. In addition, the pentose residue can be a fragment of a pentose, such as a hydroxylated 2-propoxymethyl residue or a hydroxylated ethoxymethyl residue. Particular nucleoside residues having these structures include acyclovir and gancyclovir. The pentose may also have an oxygen or sulfur substitution for a carbon atom at, for example, the 3' position of deoxyribose. Pentose derivatives include ribose derivatives, including all such sugars having modifications such as 2' substitutions and epimers of ribose, such as arabinose.

"Nucleotide component" includes nucleotides and oligonucleotides, i.e., linear sequences of nucleotides joined by phosphodiester bonds, typically prepared by synthetic means. Typically, position 3' of each nucleotide unit is linked via a phosphate group to position 5' of the next unit. In the terminal units, the respective 3' and 5' positions can be free (i.e., free hydroxyl groups) or phosphorylated. The nucleotide components of the present invention will vary widely in length. Suitable oligonucleotides can be prepared by the phosphoramidite method described by Beacage and Caruthers, *Tetrahedron Lett.* 22:1859–1862 (1981), or by the triester method according to Matteucci, et al., *J. Am. Chem. Soc.*, 103:3185 (1981), or by other methods, such as commercial automated oligonucleotide synthesizers. Oligonucleotides may also be prepared by the methods described in U.S. patent application Ser. No. 60/005,619, filed Oct. 19, 1995, entitled "Methods for Solution Phase Synthesis of Oligonucleotides", and in U.S. patent application Ser. No. 08/730,556, filed Oct. 15, 1996, entitled "Improved Coupling Activators for Oligonucleotide Synthesis", each of which is herein incorporated by reference. Nucleotide component as used herein also includes chemical modifications of nucleotides and chemical modifications of the naturally occurring oligonucleotide skeleton at any nucleotide in the polymer. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodouracil, backbone modifications, methylations, unusual base-pairing combinations such as the isobases isocytidine and isoguanidine and the like. Modifications can also include 3' and 5' modifications such as capping.

Figures 12A, 12B:
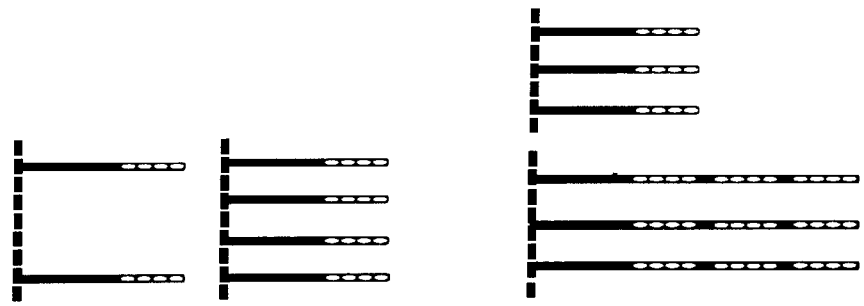
FIGS. 12A–F illustrate several embodiments of non-aptameric nucleotide-based prodrugs containing pharmacologically active nucleoside analogs.

"Photoreactive base" is a modified base that contains a photochromophore and that is capable of photocrosslinking with a target molecule. Preferentially, the photoreactive group will absorb light in a spectrum of the wavelength that is not absorbed by the target or the non-modified portions of the oligonucleotide. This invention encompasses, but is not limited to, a photoreactive group selected from the following: 5-bromouracil, 5-iodouracil, 5-bromovinyluracil, 5-iodovinyluracil, 5-azidouracil, 4-thiouracil, 5-bromocytosine, 5-iodocytosine, 5-bromovinylcytosine, 5-iodovinylcytosine, 5-azidocytosine, 8-azidoadenine, 8-bromoadenine, 8-iodoadenine, 8-iodoadenine, 8-azidoguanine, 8-bromoguanine, 8-iodoguanine, 8-aziodhypoxanthine, 8-bromohypoxanthine, 8-iodohypoxanthine, 8-azidoxanthine, 8-bromoxanthine, 9-idoxoanthine, 5-bromodeoxyuracil, 8-bromo-2'-deoxyadenine, 5-iodo-2'-deoxyuracil, 5-iodo-2'-deoxycytosine, 5-[(4-aziodphenacyl)thio]cytosine, 5-[(4-azidophenacyl)thio]uracil, 7-deaza-7-iodoadenine, 7-deaza-7-iodoguanine, 7-deaza-7-bromoadenine, and 7-deaza-7-bromoguanine (see FIG. 12).

"Photoreactive nucleotide" is defined as any nucleotide containing a photoreactive base.

"SELEX" methodology involves the combination of selection of nucleic acid ligands which interact with a target in a desirable manner, for example binding to a protein, with amplification of those selected nucleic acids. Iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention the SELEX methodology can be employed to obtain a nucleic acid ligand to a desirable target. The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixtures. The SELEX Patent Applications also describe ligand solutions obtained to a number of target species, including protein targets wherein the protein is or is not a nucleic acid binding protein.

"Nucleic acid ligand" as used herein is a non-naturally occurring nucleic acid having a specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. In one embodiment, the nucleic acid ligand is a non-naturally occurring nucleic acid. In preferred embodiments of the invention, the nucleic acid ligands are identified by the SELEX methodology. The SELEX Patent Applications also describe ligand solutions obtained to a number of target species, including protein targets wherein the protein is or is not a nucleic acid binding protein.

"Aptameric" or "Aptameric binding" refers to nucleic acid ligand binding, which is defined as an specific binding interaction between a nucleic acid ligand and a target molecule, wherein the nucleic acid ligand is not a nucleic acid having the known physiological function of being bound by the target molecule.

"Target" means any compound of interest to which a pharmacologically active compound (i.e., a nucleotide-based prodrug) binds to achieve a therapeutic response.

Drug binding may inhibit or activate the biological activity of the target molecule. A target molecule can be a protein, peptide, nucleic acid, carbohydrate, lipid, polysaccharide, glycoprotein, hormone, receptor, antigen, antibody, virus, pathogen, substrate, metabolite, cell, tissue, transition state analog, cofactor, inhibitor, drug, dye, nutrient, growth factor, etc., without limitation. In the preferred embodiment, the target is a tissue target.

"Tissue target" or "Tissue" refers to a certain subset of targets described above. According to this definition, tissues are macromolecules in a heterogeneous environment. As used herein, tissue refers to a single cell type, a collection of cell types, an aggregate of cells, or an aggregate of macromolecules. Tissues are complex targets made up of numerous macromolecules, each macromolecule having numerous potential epitopes. The different macromolecules which comprise the numerous epitopes can be proteins, lipids, carbohydrates, etc., or combinations thereof. Tissues are generally a physical array of macromolecules that can be either fluid or rigid, both in terms of structure and composition. Extracellular matrix is an example of a more rigid tissue, both structurally and compositionally, while a membrane bilayer is more fluid in structure and composition. Tissue includes, but is not limited to, an aggregate of cells, usually of a particular kind together with their intracellular substance that form one of the structural materials commonly used to denote the general cellular fabric of a given organ, e.g., kidney tissue, brain tissue. The four general classes of tissues are epithelial tissue, connective tissue, nerve tissue, and muscle tissue. Sources of the tissue, cell or subcellular structures can be obtained from prokaryotes as well as eukaryotes. This includes human, animal, plant, bacterial, fungal and viral structures. In the preferred embodiment, the target is a diseased tissue.

"Prodrug reservoir" is defined as a repository or depot of prodrug that is anchored at or in the vicinity of a target.

To "target" a drug is to provide means for directing a nucleotide-based prodrug to the target or to a site in the immediate vicinity of the Target.

"Tissue compartment" is a microanatomical subdivision within a tissue, which is defined by boundaries such as discrete sheets of epithelial or endothelial cells, or discrete structures comprised of extracellular matrix. A microanatomical subdivision is identified by analysis of appropriately prepared sections of tissue using a light or fluorescence microscope.

"Macromolecular support" is any polymer which may be covalently attached to a nucleotide-based prodrug to reduce its diffusion in the tissues. Macromolecular supports may be biological polymers (e.g., polysaccharides, polyamides, pharmacologically inert nucleotide components, etc.), derivatives of biological polymers, or non-biological polymers. Preferably the macromolecular support is a biocompatible, biodegradable polymer such as poly-lactic acid (PLA), poly-glycolic acid, poly($\epsilon$-caprolactone), poly($\beta$-hydroxybutyrate), poly($\beta$-hydroxyvalerate), polydioxanone, poly(ethylene terephthalate), poly(malic acid), poly(tartronic acid), poly(ortho esters), polyanhydrides, polycyanoacrylates, poly(phosphoesters), polyphosphazenes, hyaluronidate, polysulfones, polyacrylamides, polymethacrylate, CarboPol, hydroxyapaptite, chimeric recombinant elastin-silk protein (Protein Polymers, Inc) and collagen (Matrix Pharmaceuticals, Inc) (for detailed discussion of the above mentioned polymers, see, Park, K. et al. (1993) Biodegradable Hydrogels for Drug Delivery. Technomic Publishing Co., Inc. Lancaster, Pa.). In preferred embodiments, macromolecular supports are resorbed in the tissues, but in certain applications the macromolecular support may resist tissue resorption.

A "biocompatible polymer" is any chemical polymer that is sufficiently non-toxic and inert to use as a macromolecular support.

To "anchor" is to bind a nucleotide-based prodrug at or in the vicinity of a target, thereby restricting the nucleotide-based prodrug's volume of distribution within or around the target. In one embodiment of the invention, the nucleotide-based prodrug is anchored by means of aptameric binding of a nucleic acid ligand component of the nucleotide-based prodrug to the target. In another embodiment, the nucleotide-based prodrug is anchored at or in the vicinity of the target by forming a covalent bond between one or more photoreactive bases in the nucleotide component of the nucleotide-based prodrug and the target. In another embodiment, the nucleotide-based prodrug is anchored at the desired site by covalently coupling the nucleotide components of the nucleotide-based prodrug to a macromolecular support.

"Drug activation" is the process whereby a prodrug is converted to a pharmacologically active drug.

"Drug release" is the process whereby a pharmacologically active drug is released from a nucleotide-based prodrug reservoir.

"Adapter molecule" is defined as a molecule that can be used to couple a pharmacologically active drug to a nucleotide component via junctional phosphodiester or carbonyl ester bonds. Examples of adapter molecules include, but are not limited to, 1,2 ethanediol, succinic acid and $\gamma$-hydroxy butyric acid.

"Radiosensitizer" or "Radiosensitizing drug" as used herein is an agent whose presence in a tissue potentiates the efficacy and/or reduces the adverse affects of any radio therapeutic modality, including but not limited to, X-irradiation, gamma irradiation, ultraviolet light irradiation, neutron beam irradiation, etc. Radiosensitizers do not emit therapeutic photons or any therapeutic particles such as electrons, but they may be stimulated to do so by an external source of radiation. Examples known in the art include halopyrimidines, including 5-fluorodeoxyuridine, 5-bromodeoxyuridine and 5-iododeoxyuridine.

"Radiotherapeutic" as used herein is a molecule whose emission of photons, $\beta$-particles (electrons) or alpha particles can be exploited as a therapeutic agent. Radiotherapeutic agents may be administered by multiple routes of administration, including intravenous injection, subcutaneous injection, intramuscular injection, intraoccular injection, intraarticular injection, intradermal injection, iontophoretic application, intrathecal injection, intraumoral injection, intraperitoneal injection, intralesional injection or topical administration.

"Bilayer vesicles" are closed, fluid-filled microscopic spheres which are formed principally from individual molecules having polar (hydrophilic) and non-polar (lipophilic) proteins. The hydrophilic portions may comprise phosphato, glycerolphosphato, carboxy, sulfato, amino, hydroxy, choline and other polar groups. Examples of non-polar groups are saturated or unsaturated hydrocarbons such as alkyl, alkenyl or other lipid groups. Sterols (e.g., cholesterol) and other pharmaceutically acceptable adjuvants (including antioxidants like alpha-tocopherol) may also be included to improve vesicle stability or confer other desirable characteristics.

"Liposomes" are a subset of bilayer vesicles and are comprised principally of phospholipid molecules which contain two hydrophobic tails consisting of long fatty acid chains. Upon exposure to water, these molecules spontaneously align to form a bilayer membrane with the lipophilic ends of the molecules in each layer associated in the center of the membrane and the opposing polar ends forming the respective inner and outer surface of the bilayer membrane. Thus, each side of the membrane presents a hydrophilic surface while the interior of the membrane comprises a lipophilic medium. These membranes when formed are generally arranged in a system of concentric closed membranes separated by interlamellar aqueous phases, in a manner not dissimilar to the layers of an onion, around an internal aqueous space. These multilamellar vesicles (MLV) can be converted into unilamellar vesicles (UV), with the application of a shearing force.

"Pharmaceutically or therapeutically effective dose or amount" refers to a dosage level sufficient to induce a desired biological result. That result may be the delivery of a pharmaceutical agent, alleviation of the signs, symptoms or causes or a disease or any other desirous alteration of a biological system.

A "host" is a living subject, human or animal, into which a drug is administered.

The present invention provides nucleotide-based prodrugs comprising a pharmacologically active drug covalently attached to one or more nucleotide components. The nucleotide-based prodrugs of the invention simultaneously provide the unique properties of anchoring the nucleotide-based prodrug at or in the immediate vicinity of the target and/or providing for sustained release of the active drug component. Control of the sustained release of the active drug component is achieved by strategically modifying nucleotides within the nucleotide component. No other classes of polymers, biological or non-biological, has the chemical properties suited to perform this function. The ability to control the rate of covalent bond hydrolysis, and therefore the rate of drug release and activation, also distinguishes nucleotide-based prodrugs described in the present invention from all other sustained drug release technologies. The release and activation of the active drug component of a nucleotide-based prodrug arises from hydrolysis of the junctional ester bond joining the active drug component to the nucleotide component of the nucleotide-based prodrug. Significantly, the sensitivity of the junctional ester bond to hydrolysis is controlled by making chemical modifications at appropriate positions within the nucleotide component(s). In addition, the phosphodiester backbone of the nucleotide component may be rendered less susceptible to hydrolysis in vivo by performing one or more chemical modifications to the phosphodiester bond. Further, the rate of hydrolysis of the junctional ester bond may be influenced significantly by the nucleotide component, which may sterically mask the attached drug and/or junctional ester bonds.

The nucleotide-based prodrugs of the invention also have the property of being tightly sequestered and retained at or near the desired target, for example, in a specific histological compartment within a diseased tissue. The nucleotide-based prodrug may be sequestered, for example, by specific aptameric binding and/or photocrosslinking of the nucleotide component to a tissue, or by a poorly diffusible macromolecular support to which the nucleotide component is bound. Histological compartments are bounded by barriers, such as sheets or epithelial or endothelial cells, zones of extracellular matrix comprised of filamentous proteins and glycoproteins, or any sheet-like extracellular structure comprised of macromolecules. Thus, histological compartments are segregated domains within a tissue. The selected tissue compartment will be the optimal therapeutic location to anchor the nucleotide-based prodrug, thereby creating a prodrug reservoir from which the active drug is released upon activation by hydrolysis of junctional phosphodiester or carbonyl ester bonds. Thus, with the nucleotide-based prodrugs of the present invention, high drug levels can be confined to or near the desired target, thereby avoiding systemic toxicity associated with other modes of drug administration.

Some of the preferred nucleotide-based prodrugs are members of the following general classes. These examples are not meant to be limiting and are to be construed as merely illustrative of certain embodiments of the invention.

Nucleotide-Based Prodrugs Comprising a Nucleic Acid Ligand Component

One approach to achieving a nucleotide-based prodrug having the combined properties of tissue anchoring and sustained release of the active drug component is to covalently bind the pharmacologically active drug component via a junctional ester bond to a nucleotide component which is nucleic acid ligand. In the preferred embodiment, the nucleic acid ligand is identified by the SELEX method. The function of the nucleic acid ligand is to target and sequester the nucleotide-based prodrug to the desired target by virtue of specific binding of the nucleic acid ligand to the target. An example of a nucleic acid ligand is illustrated in FIG. 1A. The binding properties of a nucleic acid ligand are determined by its unique 3-dimensional structure, as described in the SELEX Patent Applications.

In one embodiment of the present invention, the nucleotide component of the nucleotide-based prodrug comprises a nucleic acid ligand that incorporates or is covalently bonded via junctional ester bonds to one or more pharmacologically active nucleoside analogs, which are released and activated when the nucleotide-based prodrug is hydrolyzed by tissue nucleases (FIG. 1B). The nucleoside analogs may be inserted at any position of the nucleic acid ligand, provided that the insertions do not interfere with the binding properties of the nucleic acid ligand. In the preferred embodiment, the pharmacologically active nucleoside analogs are attached to the 3' end, the 5' end or both ends of the nucleic acid ligand. In each of these embodiments, it is necessary that such substitutions do not alter the ability of the nucleic acid ligand to bind to its target. The nucleic acid ligand anchors the nucleotide-based prodrug to the target, and the hydrolysis of the nucleic acid ligand releases the nucleoside analogs, which then have access to the target (FIG. 3). The immediate products of nucleotide-based prodrug hydrolysis may include 5' and/or 3' nucleoside monophosphate derivatives of the nucleoside analogs, which are rapidly converted to nucleosides by tissue nucleotidases.

Figures 5A, 5B:
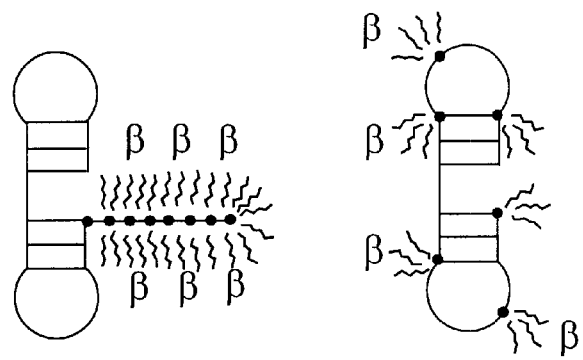
FIGS. 5A and B illustrate one example of a radioactive nucleotide-based prodrug comprising a nucleic acid ligand that binds to a target. In this example, a nucleotide component containing 5-Bromouridine is added to the nucleic acid ligand as a postSELEX modification. The nucleotides in the polymer have 2'O-methyl ribose residues for nuclease resistance.

FIG. 1C illustrates an example of a nucleotide-based prodrug comprising a labelled nucleic acid ligand component wherein α-[$^{32}$P] nucleotides are incorporated into a nucleic acid ligand, thereby providing a radiotherapeutic nucleotide-based prodrug. In this embodiment, it may be desirable to create nucleotide-based prodrugs comprising labelled nucleic acid ligand components with internucleotide bonds that are sufficiently resistant to enzymatic attack to markedly reduce or prevent hydrolysis in vivo (FIG. 5A). For example, in embodiments wherein the nucleic acid ligand comprises radioactive isotopes such as $^{32}$P, it is critical that the $^{32}$P remain at or in the vicinity of the desired target in order to avoid bone marrow toxicity which may occur if $^{32}$P were hydrolyzed from the nucleic acid ligand.

FIG. 1D illustrates a nucleotide-based prodrug comprising a nucleic acid ligand component, pharmacologically active nucleoside analog(s), and photoreactive nucleotide base(s). Examples of photoreactive bases are illustrated in FIG. 7. The photoreactive nucleotides may be inserted at any position within the nucleic acid ligand, provided that they do not interfere with the binding properties of the nucleic acid ligand. The photoreactive bases serve to assist in the anchoring of the nucleotide-based prodrug to the target by forming covalent bonds with the target upon exposure of the nucleotide-based prodrug to UV light.

In the preferred embodiments of the nucleotide-based prodrugs such as those in FIGS. 1B–D the nucleic acid ligand is identified by the SELEX process. In the preferred embodiments, nucleoside analogs, radioactive nucleotides and photoreactive nucleotides are added to the SELEX-derived nucleic acid ligand as postSELEX modifications. The postSELEX modifications may be carried out by first converting the nucleoside analog or photoreactive nucleotide to a phosphoramidite nucleotide or other suitable substrate for standard oligonucleotide synthetic methods (Beaucage, S. L. and Caruthers, M. H. (1981) *Tetrahedron Let.* 22:1859–1862; Beaucage, S. L. (1984) *Tetrahedron Let.* 25:375–378; Beaucage, S. L. (1993) *Oligonucleotide Synthesis: Phosphoramidite Approach.* In: Protocols for Oligonucleotides and Analogs-Synthesis and Properties (Agrawal, Sudhir, Ed). Humana Press, Totowa, N.J. pp. 33–62; Damha, M. and Ogilvie, K. K. (1993) *Oligonucleotide Synthesis: Silyl-Phosphoramidite Method* In: Protocols for Oligonucleotides and Analogs-Synthesis and Properties (Agrawal, Sudhir, Ed). Humana Press Totowa, N.J., pp. 81–114). The nucleoside analogs and photoreactive nucleotides may also be incorporated into the nucleic acid ligand as nucleotide 5'-triphosphates by polymerase enzymes in enzymatic syntheses of the ligands.

U.S. patent application Ser. No. 08/442,062, filed May 16 1995, entitled "Methods of Producing Nucleic Acid Ligands", now U.S. Pat. No. 5,595,877, describes methods for identifying and designing improved nucleic acid ligands identified by the SELEX process, wherein the improvement comprises, for example, improved binding affinity. For example, a nucleic acid ligand is first identified by the SELEX process. The nucleic acid ligand is then modified at stategic positions by adding chemically modified nucleotide residues, such as nuclease resistant nucleotides, and/or by modifying the phosphodiester bonds. The nucleic acid ligand can also be identified by a method termed photo-SELEX. U.S. patent application Ser. No. 08/123,935, filed Sep. 17, 1993, entitled "Photoselection of Nucleic Acid Ligands", supra, describes a SELEX based method for selecting nucleic acid ligands containing photoreactive groups capable of binding and/or photocrosslinking a target molecule. The addition of multiple photoreactive bases increases the number of potential covalent crosslinks.

Upon administration of the nucleotide-based prodrug such as those shown in FIGS. 1B–D, the nucleic acid ligand binds the nucleotide-based prodrug to the target, such as proteins or other macromolecules in a diseased tissue. As the nucleic acid ligand is hydrolyzed over time by nucleases and/or other phosphodiesterases in the tissues, the active drug is in turn released over time and a drug gradient is established at or in the vicinity of the target (see FIG. 3). As such the diffusion distance between the prodrug reservoir and the target is minimized, which results in higher local drug concentrations and thus requires lower total doses to achieve effective therapy. The sustained release properties of the nucleotide-based prodrug leads to less frequent applications of the nucleotide-based prodrug.

Nucleotide-Based Prodrugs Comprising Pharmacologically Active Non-Nucleoside Drugs Bonded to Nucleic Acid Ligands Nucleotide-based prodrugs may also be constructed by covalently binding one or more non-nucleoside drugs to a nucleic acid ligand via a junctional ester bond. In one embodiment, the junctional ester bond is a phosphodiester bond, and the pharmacologically active drug and a ribose molecule in the nucleic acid ligand each contribute a hydroxyl group to the junctional phosphodiester bond (FIG. 1E). In another embodiment, the junctional ester bond is a junctional carbonyl ester, and the pharmacologically active drug molecule contributes a carboxyl group and the terminal ribose molecule in the nucleic acids ligand contributes a hydroxyl group to the junctional ester bond (FIG. 1F). In the preferred embodiments, either a 3' or 5' hydroxyl group is contributed by the nucleic acid ligand. In embodiments in which the non-nucleoside drug component does not have a hydroxyl group, the drug may be coupled to an adapter molecule which possesses a hydroxyl group, preferably via a physiologically hydrolyzable bond. The hydroxyl group on the adapter molecule is then in turn bonded to a nucleotide component via a phosphodiester bond or another suitable linkage such as a carbonyl ester, either or amide bond (FIGS. 1G and 1H). Suitable adapter molecules include, but are not limited to, 1,2-ethanediol, succinic acid and γ-hydroxy butyric acid.

Nucleotide-Based Prodrugs Comprising a Pharmacologically Active Nucleoside Analog Bonded to a Nucleotide Component Which Lacks Nucleic Acid Ligand Binding Properties ("Non-Aptameric Prodrugs")

Nucleotide-based prodrugs may also be constructed by combining one or more pharmacologically active nucleoside analogs with one or more nucleotide components which do not have aptameric binding properties. These nucleotide-based prodrugs are administered locally. In one embodiment, the nucleotide component is attached to a macromolecular support which anchors the nucleotide-based prodrug to the site of administration, thereby reducing diffusion of the nucleotide-based prodrug in vivo and controlling the distribution of active drug (FIG. 2A). In the preferred embodiment, the macromolecular support is a biocompatible polymer. A large number of these nucleotide-based prodrugs, which may be termed non-aptameric nucleotide-based prodrugs, may be designed by using a wide variety of combinations of pharmacologically active nucleoside analogs, including combinations of different nucleoside analogs, nucleotide components and macromolecular supports. By changing the sequence and molar ratio of these components, it is possible to design nucleotide-based prodrugs equipped with a wide range of biochemical activities, potencies and rates of drug release. The combinatorial possibilities are enormous, and a few examples of this class of nucleotide-based prodrugs are shown in FIG. 12.

One embodiment of a non-aptameric nucleotide-based prodrug comprises a sequence of pharmacologically active nucleoside analogs at one end of the nucleotide component of a nucleotide-based prodrug, and a macromolecular support at the other end of the nucleotide component (FIGS.

Figures 12C, 12D, 12E:
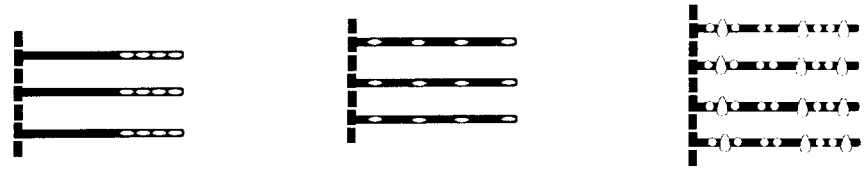
Figure 12F:
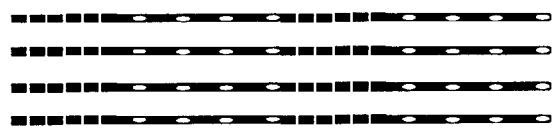

12A–C). The rate of sustained release of the nucleoside analogs from the nucleotide-based prodrug may be manipulated as desired by incorporating nuclease resistant modified nucleotides in the nucleotide component (e.g., 2'-O-methyl, 2'-fluoro, 2'-difluoro or 2'-amino nucleotides or arabinosides) and/or by modifying the phosphodiester bonds at strategic positions in the nucleotide component and/or by altering the length and composition of the nucleotide component (FIGS. 12B–E). In other embodiments, the nucleotide-based prodrug may be comprised of alternating nucleotide components covalently bound to alternating macromolecular support polymers (FIG. 12F). In this embodiment, the nucleotide component of the nucleotide-based prodrug not only provides a reservoir of active drug, but it may also contribute valuable physical properties to the macromolecular support. For example, the nucleotide component may be sufficiently large to reduce diffusion of the nucleotide-based prodrug in tissues. Alternatively, the nucleotide component may form secondary structures by hydrogen bonding between segments of complementary sequences in the nucleotide component. The length and composition of complementary sequences may determine the gelling temperature of the nucleotide-based prodrug in vivo.

Figure 13:
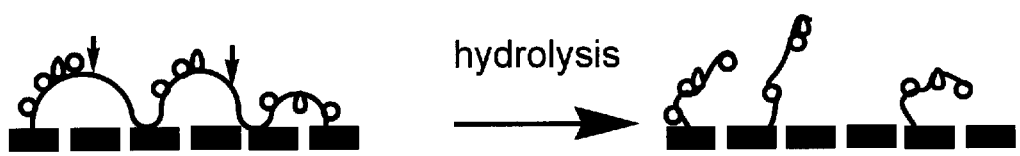
FIG. 13 illustrates non-aptameric nucleotide-based prodrugs with multiple points of attachment to the poorly diffusible macromolecular support. In nucleotide-based prodrugs with a single point of attachment, one endonucleolytic cleavage releases non-activated prodrug nucleotide components from the poorly diffusible macromolecular support. In prodrugs with multiple points of attachment, multiple endonucleolytic cleavages are required to release non-activated prodrug nucleotide components from the macromolecular support. Therefore, multiple points of attachment may prolong the sustained release effect. Arrows indicate sites of endonucleolytic attack.
Figure 26:
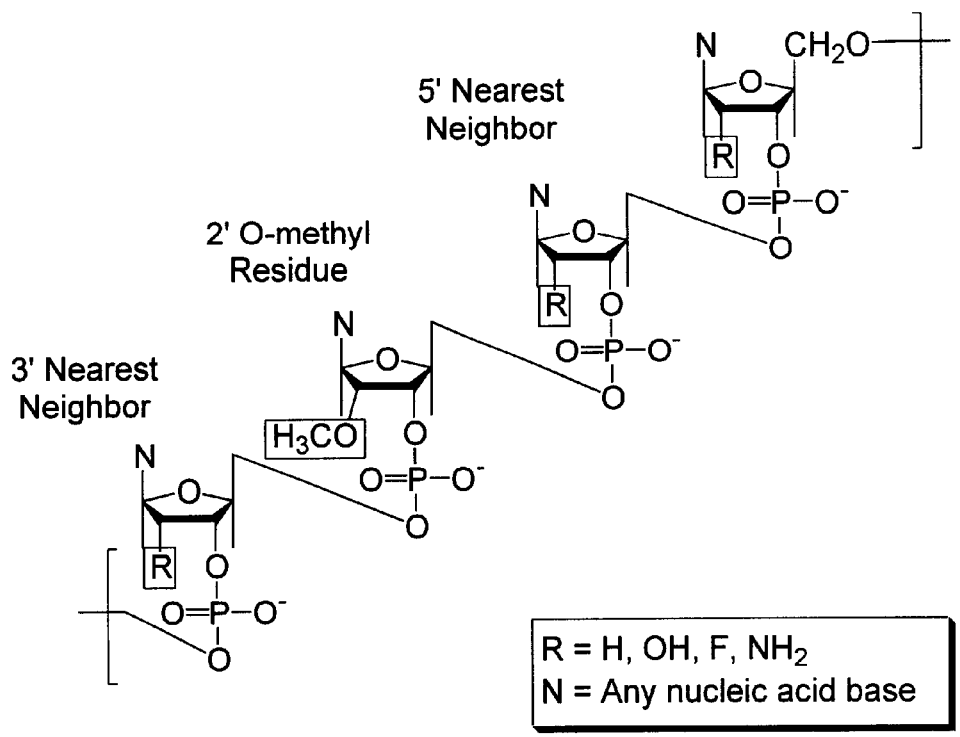
FIG. 26 illustrates 5' and 3' nearest neighbors of a 2'-O-methyl residue in a nucleotide component.

It may be important to avoid cleavage of the modified nucleotide component into short polymers which contain the unactivated (i.e., incompletely hydrolyzed) nucleoside analogs, which might diffuse away from the target prior to release and activation of the nucleoside analog. To ensure that active nucleoside analogs will be released from the polymer in the fully hydrolyzed, active state at or in the vicinity of the target, the nucleotide-based prodrug may be designed such that the active nucleoside analogs are strategically interspersed throughout the nucleotide components as illustrated in FIG. 12D. The function of the non-pharmaceutically active nucleotides comprising the nucleotide component is to influence the release and activation of the active nucleoside analog components. One strategy for preventing the release of incompletely hydrolyzed short polymers is to create nucleotide-based prodrugs in which the bonds between the pharmacologically active drug molecules are more susceptible to hydrolysis than the bonds between the pharmacologically inactive nucleotides within the nucleotide component. For example, the nuclease resistance of the junctional phosphodiester bonds between the pharmacologically inactive nucleotides within the nucleotide component may be maximized by incorporating 2'-O-methyl substituted nucleotides into the nucleotide component (FIG. 26). Less nuclease resistant bonds may be used to link pharmacologically active nucleotides that are to be released and activated by hydrolysis (FIG. 26). For example, a pharmacologically active drug is preferably placed on the 5' side of nucleotides containing, for example, a 2'-O-methyl modification (FIG. 26). In this case, the active nucleoside drug will hydrolyze before the nucleotide adjacent to the drug, since the latter is bound via a highly nuclease resistant bond to its 3' nearest neighbor In another embodiment, the nucleotide-based prodrug may comprise a nucleotide component having nucleoside analogs interspersed throughout the polymer, wherein the polymer is attached to the macromolecular support at multiple positions in the nucleotide sequence (FIG. 13). In this embodiment, as the polymer is hydrolyzed, multiple subfragments of the nucleotide component will remain bound to the macromolecular support. These subfragments will then be hydrolyzed further in a manner designed to provide a sustained release of the active nucleoside analogs.

Nucleoside-based prodrugs containing multiple sites of attachment to the macromolecular support and multiple pharmacologically active nucleoside analogs are expected to provide more prolonged sustained drug release, and to have increased in vivo half lives compared with nucleotide-based prodrugs that are attached at only one site. By varying the number of attachment sites in each nucleotide-based prodrug, it is possible to create a series of nucleotide-based prodrugs with a range of drug release rates. In addition, by modifying the nuclease sensitivity of certain nucleotides within the nucleotide component it may be possible to further reduce the rate of drug release and activation.

A further embodiment of the invention provides nucleotide-based prodrugs comprising two or more different pharmacologically active nucleoside analogs within the same nucleotide-based prodrug (FIG. 12E). For example, two different nucleotide analogs containing immunosuppressive purines with different mechanisms of action, such as 6-mercaptopurine and deoxycoformycin, may be inserted into the same nucleotide component to create a nucleotide-based prodrug having a synergistic combination of therapeutic agents (FIG. 15). In this example, deoxycoformycin's immunosuppressive effect is achieved by inhibiting adenosine deaminase, whereas 6-mercaptopurine's effect is achieved by its metabolite, thioinosine monophosphate (TIMP), which inhibits the early steps in de novo purine biosynthesis, including the first enzyme in the pathway, amidophosphoribosyl transferase. Examples of pharmacologically active nucleoside analogs that may be used to create nucleotide-based prodrugs are listed in Tables 1–2.

Figure 17:
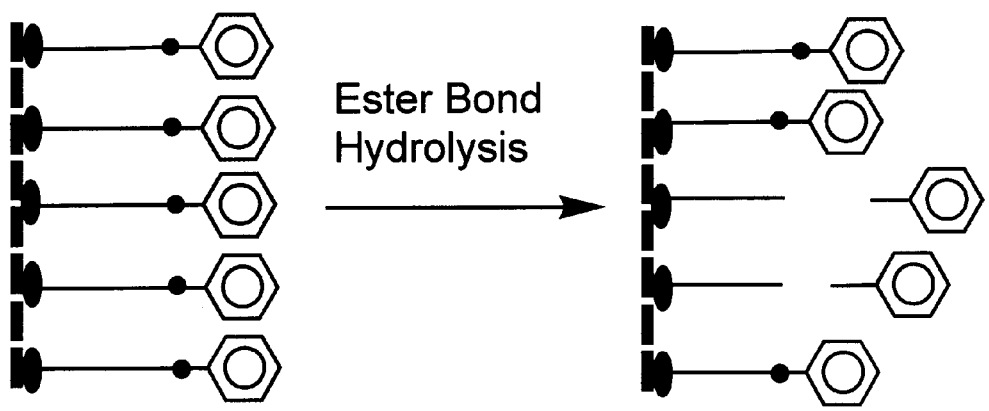
FIG. 17 illustrates the sustained release properties of a non-aptameric nucleotide based prodrug containing pharmacologically active non-nucleoside drugs. Hydrolysis of junctional ester bonds releases active drugs from the poorly diffusible macromolecular support.
Figure 19A:
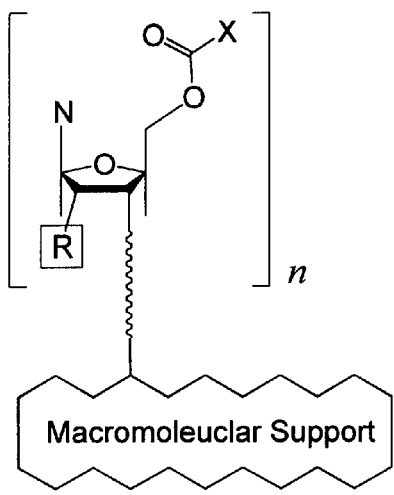
FIGS. 19A and B illustrate examples of nucleotide-based prodrugs comprised of non-nucleoside drugs coupled to nucleotide components via 5' junctional carbonyl ester bonds (19A) or 3' junctional carbonyl ester bonds (19B). n is greater than or equal to 1. X is any drug with a carboxyl group.
Figure 19B:
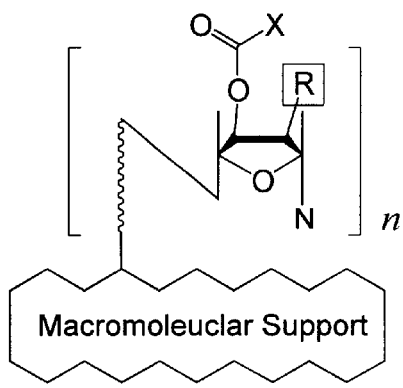
Figures 20A, 20B:
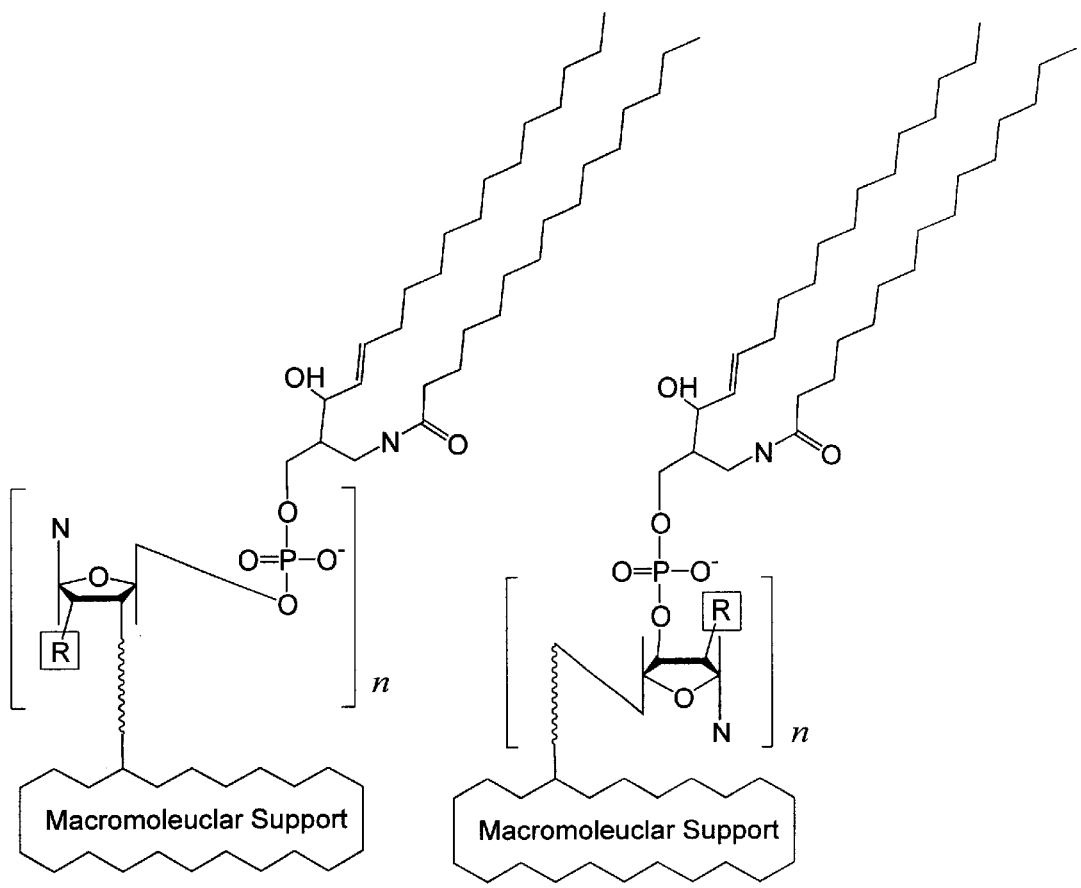
FIGS. 20A and B illustrate examples of nucleotide-based prodrugs comprised of ceramide coupled to nucleotide components via 5' junctional phosphodiester bonds (20A) or 3' junctional phosphodiester bonds (20B).

Nucleotide-based Prodrugs Comprising
Pharmacologically Active Non-nucleoside
Compounds Bonded to Non-aptameric Nucleotide
Components Nucleotide-based prodrugs may be constructed by covalently bonding one or more pharmacologically active non-nucleoside drugs via junctional ester bonds to a nucleotide component which in turn is covalently bonded to a macromolecular support (FIG. 17). The nucleotide-based prodrugs of this embodiment are administered locally. In one embodiment, the covalent bond between the drug component and the nucleotide component is a junctional phosphodiester bond between a hydroxyl group on the drug and the 3' or 5' phosphate of a nucleotide or a nucleotide component (FIG. 18). In other embodiments, the covalent bond involves a junctional carbonyl ester bond between a carboxyl group on the pharmacologically active non-nucleoside drug and the 3' or 5' hydroxyl group of a nucleotide component (FIG. 19). Hydrolysis of the junctional ester bonds linking the non-nucleoside drug to the nucleotide component releases and activates the drug, resulting in a higher concentration of the active drug in the immediate vicinity of the target. While the junctional ester bonds illustrated in FIGS. 18 and 19 have not been identified in naturally-occurring molecules, it is anticipated that these junctional carbonyl ester and phosphodiester bonds will be cleaved by esterases and nucleases in vivo, and that chemical modifications of the nucleotide component can be used to modulate the sensitivity of this junctional ester bond to hydrolysis. The ability to utilize a junctional carbonyl ester to covalently bond the drug to the nucleotide component will expand the repertoire of non-nucleoside drugs that can be converted into nucleotide-based prodrugs, and will give rise to nucleotide-based prodrugs with a broader range of hydrolytic sensitivity than that afforded by phosphodiester bonds.

A wide variety of non-aptameric nucleotide-based prodrugs may be synthesized by combining a pharmacologically active non-nucleoside compound with one or more nucleotide components. In one embodiment, the nucleotide-based prodrug comprises one or more pharmacologically active non-nucleoside drugs having hydroxyl groups covalently bonded via a junctional phosphodiester bond to the 3' or 5' position of one or more nucleotide components, which in turn are covalently coupled to a macromolecular support. The addition of multiple nucleotides or multiple nucleotide components to a drug molecule is expected to further delay the rate of drug release and activation. The rate of sustained release may be further altered by incorporating nuclease resistant nucleotides, for example, 2'-O-methyl, 2'-fluoro, 2'-difluoro or 2'-amino nucleotides or arabinosides at strategic positions in the nucleotide component, and/or by modifying the phosphodiester bonds in the nucleotide component and/or by altering the length and composition of the intervening sequence.

A further embodiment of the invention provides a nucleotide-based prodrug comprising combinations of both a pharmacologically active non-nucleoside compound and one or more pharmacologically active nucleoside analogs which are covalently bonded to one or more nucleotide components. Pharmacologically active non-nucleoside drugs that may be used to create nucleotide-based prodrugs are listed in Tables 3–8.

Figures 24A, 24B, 24C, 24D:
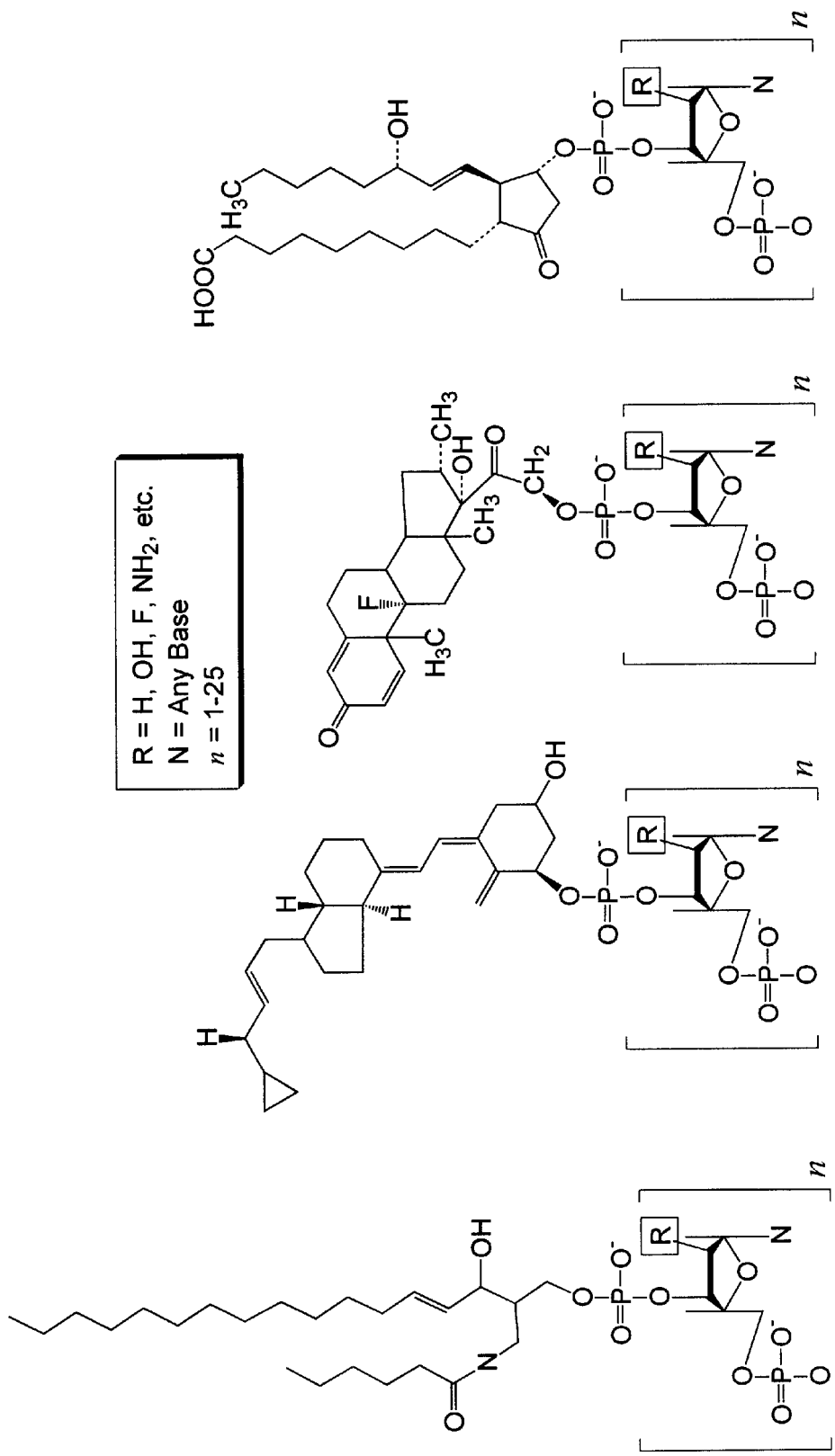
FIGS. 24A–D illustrate several examples of nucleotide-based prodrugs comprising pharmacologically active lipophilic compounds linked to nucleotide components. The hydrophilic nucleotides are aligned at the bottom of the figure, and the lipophilic components of the prodrugs are at the top.

Nucleotide-based Prodrugs Comprising a Pharmacologically Active Lipophilic Compound Covalently Bonded to a Nucleotide Component The invention further includes nucleotide-based prodrugs with amphiphilic properties. These nucleotide-based prodrugs comprise pharmacologically active, non-polar lipids, such as retinoids, vitamin D analogs, eicosanoids, steroids or ceramide analogs covalently bonded to one or more nucleotide components via junctional ester bonds (FIG. 24). Hydrolysis of the junctional ester bonds in vivo releases either the active lipid compound or a monophosphorylated derivative of the active lipid compound that is subsequently activated by tissue phosphatases. In one embodiment, the amphiphilic nucleotide-based prodrug is administered in a lipid vehicle comprised of a lipid bilayer vesicle, preferably a liposome. In one embodiment, the amphiphilic nucleotide-based prodrug is inserted into the lipid bilayer of the liposome and the hydrophilic nucleotide component of the nucleotide-based prodrug is oriented either towards the outside or the inside surface of the liposome. Since certain non-polar lipophilic drugs tend to diffuse more rapidly out of liposomes in vivo compared to certain amphiphilic drugs, this embodiment offers a significant advantage since these amphiphilic nucleotide-based prodrugs will be encapsulated more efficiently into the liposomes. This will result in a reduction of the diffusion of the amphiphilic nucleotide-based prodrugs from liposomes, thereby prolonging the in vivo half life of the lipophilic drugs. Release and full activation of liposomally delivered amphiphilic nucleotide-based prodrug arises from hydrolysis of the junctional ester bonds joining the pharmacologically active lipid drug to the nucleotide components.

Many pharmacologically active lipophilic compounds may be converted into nucleotide-based prodrugs. Nucleotide-based prodrugs of this type may be described as amphiphilic phospholipids having a hydrophilic head group (the nucleotide component) linked via junctional ester bonds to a pharmacologically active lipid. Examples of nucleotide-based prodrugs comprising pharmacologically active lipophilic compounds are illustrated in FIG. 24. In one embodiment, the nucleotide-based prodrug comprises one or more lipophilic compounds having hydroxyl groups covalently bonded to the 3' or 5' end of one or more nucleotide components via junctional phosphodiester bonds. In another embodiment, the covalent bond is a carboxyl ester which occurs through a carboxyl group of the lipophilic compound. Examples of 5' and 3' junctional phosphodiester linkages and 3' and 5' junctional carbonyl ester linkages are illustrated in FIG. 24.

As mentioned above, the nucleotide-based prodrugs of this embodiment are amphipathic, and therefore they may be readily loaded into lipid bilayer vesicles using, for example, pH gradient methodology. These nucleotide-based prodrugs are oriented in a polarized fashion, such that the lipid component penetrates the lipid bilayer and the charged nucleotide component is restricted to the membrane surface as illustrated schematically in FIG. 25. In a preferred embodiment, the lipid bilayer vesicle is a liposome. The organization of the nucleotide-based prodrugs illustrated in FIGS. 24 and 25 relative to the lipid bilayer is strongly supported by ordering of natural phospholipids. The polarized orientation of amphiphilic nucleotide-based prodrugs in the lipid bilayer is also expected to provide a means of reducing the diffusion of lipophilic drugs from liposomes in vivo.

Figures 25A, 25B:
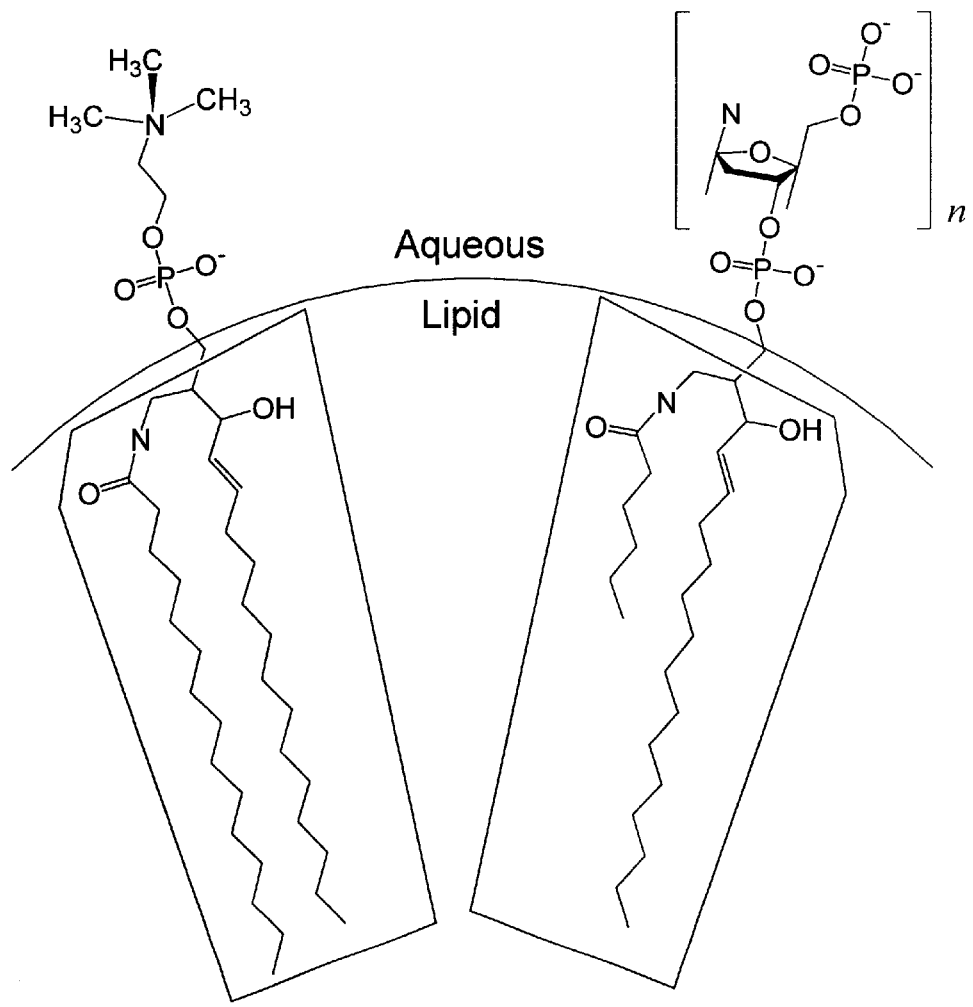
FIGS. 25A and B illustrate a physiological membrane phospholipid, sphingomyelin (25A), and an amphiphilic nucleotide-based prodrug of ceramide C-6 (25B) as they would be oriented in the lipid barrier of a lipid emulsion, liposome or cellular membrane.

Relevant to the present invention is the observation that the amphiphilic structures of the nucleotide-based prodrugs illustrated in FIG. 24 are similar to the structures of certain natural phospholipids in mammalian cell membranes. For example, sphingomyelin (SM) is present in the outer leaflet of the lipid bilayer of cell membranes. SM is comprised of a charged hydrophilic choline head group linked via junctional phosphodiester bonds to a lipid alcohol, ceramide (FIG. 25). Ceramide is a lipid "second messenger" and amplifies certain growth suppressive signals by activating ceramide responsive enzymes within the cell. Ceramide is released from sphingomyelin by phospholipases termed "sphingomyelinases" (Smases) that cleave the junctional phosphodiester bond joining ceramide to phosphocholine. Thus, SM may be viewed as a membrane-associated reservoir of pro-ceramide molecules, poised to be delivered to its protein targets in the cell interior.

Ceramide, retinoids, vitamin D analogs, steroids, eicosanoids and other biologically active lipid compounds must gain access to the cell interior to reach the proteins that mediate their biological effects. The lipid compounds in these nucleotide-based prodrugs are inactive until released by hydrolysis of the junctional ester bonds joining the lipophilic compound to the nucleotide component. Thus, junctional ester bond hydrolysis is required to activate not only natural sphingophospholipids but also the nucleotide-based lipid prodrugs. By analogy to sphingomyelin, the amphiphilic nucleotide-based prodrugs may be viewed as membrane associated reservoirs of potent agonists, poised to enter the cell interior. The main difference is that specific enzymes, sphingomyelinases, have evolved to release ceramide, whereas the lipophilic drugs are released from the nucleotide-based prodrugs via enzymatic activities (e.g., nucleases, phosphodiesterases and other esterases) that have other physiological functions. The amphiphilicity of nucleotide-based prodrugs will promote efficient encapsulation of these nucleotide-based prodrugs into liposomes and other lipid based formulations. Thus, the emphilic nucleotide-based prodrugs of the present invention provide a novel drug reformulation technology and a method by which to expand lipid-based drug delivery.

Another potential therapeutic benefit of using liposomal formulations of these nucleotide-based prodrugs is to reduce the pharmacokinetic problem of self-induced metabolism. For example, certain retinoids stimulate cells to express enzymes, which can catalyze reactions that inactivate the retinoids. Retinoids sequestered in liposomes are protected from catabolism, and their prolonged release provides a continuous source of active drug to compensate for the self-induced metabolism.

Manipulating the Sustained Release Properties of Nucleotide-based Prodrugs

The ability to manipulate the sustained release of the active form of a drug from a nucleotide-based prodrug is one important feature of nucleotide-based prodrugs. Sustained release requires that the nucleotide-based prodrug bind to the target. The binding of the nucleotide-based prodrug is non-covalent in the case of nucleotide-based prodrugs comprising nucleic acid ligands, and it is covalent in the case of non-aptameric nucleotide-based prodrugs comprising photoreactive nucleotide components. In the case of non-aptameric nucleotide-based prodrugs comprising a macromolecular support, the support reduces or eliminates diffusion of the nucleotide-based prodrug, thereby restricting the volume of the drug distribution.

Another critical factor influencing the sustained release properties of a nucleotide-based prodrug is the sensitivity of the junctional ester bond between the nucleotide component and the drug to hydrolysis by tissue nucleases and esterases. Together, the binding properties, diffusion rate and the sensitivity of nucleotide-based prodrugs to hydrolytic activation will determine the residence time of the nucleotide-based prodrug in the tissue and the in vivo half life of the nucleotide-based prodrug. Additionally, the in vivo half-life of the pharmacologically active component released from the nucleotide-based prodrug will be determined by many factors, including the rate of hydrolysis of the nucleotide component, the chemical structure of the drug, the anatomic site from which it is released, its volume of distribution and factors relating to the host.

In one embodiment, the junctional phosphodiester bond joining the pharmacologically active drug to the nucleotide component is highly susceptible to nuclease hydrolysis. For example, the bond may link a drug to the 3' position of an unmodified ribonucleotide which has a 2' hydroxyl group that is exploited as a nucleophile by ribonucleases which rapidly hydrolyze such phosphodiester bonds.

In another embodiment, increased nuclease resistance may be desirable for drug design. In this embodiment, the junctional phosphodiester bond may link a drug to the 3' position of an unmodified deoxyribonucleotide lacking a 2' hydroxyl group.

In another embodiment, it may be useful to increase the nuclease resistance beyond the level afforded by phosphodiester bonds in deoxyribonucleotides. Below, a number of methods for modifying a nucleotide component's resistance to nuclease degradation are discussed.

Modifications of the Bases

U.S. patent application Ser. No. 08/622,772, filed Mar. 27, 1996, entitled "Pyrimidine Nucleosides as Therapeutic and Diagnostic Agents", describes nucleosides with modifications at the 5- or 6-position of a pyrimidine ring or at the 2-, 6- or 8-positions of a purine ring which may impart endo and exonuclease resistance. It is established that these modifications increase the nuclease resistance of phosphodiester bonds between two nucleotides. It is expected that in certain cases such modifications will also modify the nuclease resistance of junctional phosphodiester bonds between a nucleotide and a non-nucleotide drug molecule.

Modifications of the Sugars

RNA has been stabilized against endonucleolytic cleavage by modifying the 2'-position of the ribonucleotides. One approach to stabilization against base-specific endonucleolytic cleavage rests on the interference with base recognition by enzymes. Several strategies for this modification are known, including modification with 2'-amino and 2'-fluoro (Hobbs et al. (1993) Biochem. 12:5138; Guschlbauer et al. (1977) Nuc. Acids Res. 4:1933–1943); 2'-OCH$_3$ (Shibahara et al. (1987) Nuc. Acids Res. 15:4403; and Sproat et al. (1989) Nuc. Acids Res. 17:3373); and 2'-deoxy-2'-a-C-branched nucleosides and nucleotides (Lawrence et al. (1996) J. Org. Chem. 66:9213–9222), each of which is hereby incorporated by reference. PCT WO91/06556 (Buhr and Matteucci), also incorporated by reference, describes nuclease-resistant oligomers with substituents at the 2'-position. PCT WO91/10671 (Acevedo), also incorporated by reference, describes antisense oligonucleotides chemically modified at the 2'-position and containing a reactive portion capable of catalyzing, alkylating or otherwise affecting the cleavage of RNA, a targeting portion, and a tether portion for connecting the targeting and reactive portions.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides", abandoned in favor of U.S. patent application Ser. No. 08/430,709 filed Apr. 27, 1995, now U.S. Pat. No. 5,660,985, that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Known and Novel Preparation of 2'-Modified Nucleosides by Intramolecular Nucleophilic Displacement", now abandoned, describes oligonucleotides containing various 2'-modified pyrimidines.

In one embodiment, the rate of sustained drug release is manipulated by incorporating one or more nuclease resistant nucleotides (e.g., 2' O-methyl, 2' fluoro and 2' amino, and arabinosides) into strategic positions of the nucleotide-based prodrug. In this way, it is possible to design a series of nucleotide-based prodrugs with different rates of sustained drug release. In another embodiment of the invention, a series of nucleotide-based prodrugs each having a different nuclease resistance are combined to give rise to a drug formulation with continuous sustained release properties.

In one embodiment, the nucleotide components are rendered maximally resistant to nucleases and phosphodiesterases by employing α-N-glycosyl linkages between the base and carbon 1 of the pentose ring (Ashley, G. W. (1992) J. Am. Chem. Soc. 114:9731–9736).

Modifications of the Phosphate Backbone and Oligonucleotide Analogs

The nucleotide based pro-drugs of the present invention comprise pharmacologically active drug components whose release and activation requires hydrolysis of the junctional ester bonds which covalently bind a nucleotide component to the pharmacologically active drug. In the preferred embodiments, junctional phosphodiester bonds are used to link the drug and the nucleotide component.

Chemically modified phosphodiester linkages are known to markedly reduce nuclease sensitivity and may therefore be used to decrease the rate of drug release from nucleotide-based pro-drugs. These modifications may also be used to improve the properties of nucleotide components that are attached to the pharmacologically active component of the nucleotide-based prodrug. Modified phosphodiester linkages include phosphorothioate (Wiesler, W. T. et al. (1993) *Synthesis and Purification of Phosphorothioate DNA* In: Protocols for Oligonucleotides and Analogs-Synthesis and Properties (Agrawal, Sudhir, Ed). Humana Press, Totawa, N.J., pp. 191–206); methylphosphonate (Hogrefe, R. I. et al. (1993) *An Improved Method for the Synthesis and Deprotection of Methylphosphonate Oligonucleotides*, In: Protocols for Oligonucleotides and Analogs-Synthesis and Properties (Agrawal, Sudhir, Ed). Humana Press. Totowa, N.J. pp. 143–164), borane phosphonate (Shaw, B. R. et al., (1993) *Oligonucleotide Boranophosphate (Borane Phosphonate)* In: Protocols for Oligonucleotides and Analogs-Synthesis and Properties (Agrawal, Sudhir, Ed). Humana Press. Totowa, N.J., pp. 225–244); phosphorofluoridate and fluoridate linkages (Dabkowski, W. et al. (1993) *Oligonucleotide Phosphorofluoridates and Fluoridites*, In: Protocols for Oligonculeotides and Analogs-Synthesis and Properties (Agrawal, Sudhir, Ed) Humana Press, Totowa, N.J., pp. 245–260). PCT Publication WO 90/15065 (Froehler) describes a method for making exonuclease-resistant oligonucleotides by incorporating two or more phosphoramidite, phosphoromonothionate and/or phosphorodithionate linkages at the 5' and/or 3' ends of the oligonucleotide. PCT Publication WO 91/06629 discloses oligonucleotides with one or more phosphodiester linkages between adjacent nucleosides replaced by forming an acetal/ketal type linkage which is capable of binding RNA or DNA (Lawrence et al. (1996) *J. Org. Chem.* 66:9213–9222).

Oligonucleotide analogs may also be used to improve the properties of nucleotide components that are attached to the pharmacologically active component of the nucleotide-based prodrug. Oligonucleotide analogs include dimethylene sulfide, dimethylene sulfoxide and dimethylene sulfone linkages, as well as methylene-bridged, siloxane-bridged, carbonate-bridged, carboxymethyl-bridged, acetamide-bridged, carbamate-bridged, carbamate-morpholino-bridged and polyamide nucleic acid bridged structures (Uhlmann, E. and Peyman, A. (1993) Oligonucleotide Analogs Containing Dephospho-Internucleoside Linkages. In: Protocols for Oligonucleotides and Analogs-Synthesis and Properties (Agrawal, Sudhir, Ed). Humana Press. Totawa, N.J., pp. 355–390).

Nuclease Protective Caps.

The 3' hydroxyl termini of nucleotide components are vulnerable to exonucleolytic degradation. To stabilize and protect the 3' hydroxyl terminus, a 3'-3' cap may be attached. Synthesis is usually, but not always, initiated with a thymidine residue and the 5' end is linked to the resin. The second residue, usually another thymidine, is linked to the first via a 3'-3' phosphodiester, a nuclease resistant bond. In another embodiment, variations of the 3'-3' cap are used, including the use of all nucleotides and nucleotide analogs.

Length of the Nucleotide Component

Nucleotide components having less than 10 nucleotides are probably less dependent on secondary structure for in vivo stability than nucleotide components having greater than 10 nucleotides. The in vivo stability of unfolded polymers of 2–10 nucleotides may be dependent upon length. In general, long nucleotide components are probably more susceptible to nuclease hydrolysis than short polymers, because longer nucleotide components have more phosphodiester bonds to be attacked by nucleases.

In preferred embodiments of nucleotide-based prodrugs, the length and complexity of the nucleotide component is minimized, that is, the pharmacologically active drug is attached to a single nucleotide, or a polymer of 2–40, preferably 2–20, most preferably 2–10 nucleotides. But in certain embodiments, the nucleotide component may be lengthened up to at least 40 nucleotides to accommodate many photoreactive bases, and/or to accommodate many pharmacologically active nucleoside analogs.

Nearest Neighbor Effects on Hydrolysis of Junctional Phosphodiester Bonds Between Nucleotides Phosphodiester bonds coupled at the 3' of an adjacent nucleotide containing 2' modified ribose sugars (e.g., 2'-fluoro, 2'-amino and 2'-O-methyl substitutions) are much less susceptible to hydrolysis than phosphodiester bonds coupled to unmodified nucleotides, for example, ribonucleotides or naturally occurring deoxyribonucleotides. Therefore, a potentially active nucleoside analog is preferably inserted on the 5' side of modified nucleotides, preferably 2' O-methyl-modified nucleotides (see, e.g., FIG. 26).

Nucleotide-based Prodrug Intermediates Containing Residual Phosphoester Groups

Nucleotide-based prodrugs comprising a nucleoside analog as the drug component will be hydrolyzed in the presence of tissue nucleases, ultimately providing 5' monophosphate or 3' monophosphate derivatives of the nucleotide analogs. The monophosphate group is rapidly removed by ectonucleotidases and phosphatases to provide the active nucleoside analog drug, as illustrated by the conversion of fludarabine monophosphate to n-phosphorylated fludaribine nucleoside (9-β-D-arabinofuranosyl-3-fluoroadenine, Chun H. G. et al. (1991) *J Clin Oncol.* 9:175–88).

Nucleotide-based prodrugs containing non-nucleoside drug components coupled via junctional phosphodiester bonds to nucleotide components (see FIGS. 1C and 1F) may have a residual phosphate group that must be removed by phosphatases to fully activate the nucleotide-based prodrug. In this situation, the residual phosphate will be rapidly and quantitatively removed similar to the case of Etoposide, i.e., the phosphate is quantitatively removed by serum alkaline phosphatase, thereby activating the drug. In other cases, nucleases may initially cleave the junctional phosphodiester bond such that no phosphate remains on the non-nucleoside drug. In this case, release and activation occur simultaneously to release a pharmacologically activated compound.

Junctional Carbonyl Esters to Join Non-Nucleotide Drugs to Modified Nucleotides or Modified Nucleotide Components Hydrolysis of junctional carbonyl esters does not give rise to intermediate prodrugs having residual phosphoesters. For example, hydrolysis of each of the nucleotide-based prodrugs illustrated in FIGS. 18 and 23 will give rise to one nucleotide component plus one retinoic acid molecule, the pharmacologically active species. Typically, carbonyl esters are generally more susceptible to hydrolysis in vivo than simple phosphoesters. However, certain carbonyl esters are more resistant to hydrolysis in vivo. This may be achieved via some of the same chemical modifications that are used to stabilize phosphodiester bonds between nucleotides. For example, in cases wherein non-nucleoside drugs are coupled to the nucleotide via a junctional carbonyl ester involving the 3' hydroxyl group of ribose, it is believed that 2' substitutions of the ribose will stabilize the junctional carbonyl ester. It is not clear which enzymes cleave 3' junctional carbonyl ester bonds, since carbonyl esters do not occur in nucleic acids found in nature. However, it is known that serum and tissue fluids contain a myriad of esterase activities capable of cleaving many unnatural esters on drug molecules.

Nucleotide Components Have Unique Sustained Release Properties

The ability to manipulate the susceptibility of a nucleotide component to hydrolysis in vivo distinguishes the nucleotide-based prodrugs of the present invention from other classes of prodrugs. Peptide bonds have been used to attach drug molecules to pendant chains on hydrogel polymers (Shen, W-C et al. (1985) *J. Biol. Chem.*, 260:10905–10908; Kopecik, J. (1984) *Biomaterials*, 5:19–25; Rejmanova et al. (1985) *Biomaterials*, 6:45–48) For a review, see, Gebelein in: Bioactive Polymeric Systems (1985) Gebelein, C. G. and Carraher, C. E. Editors. Plenum Press, New York, N.Y. Proteins are hydrolyzed in vivo, however, protease sensitivity is much more difficult to manipulate than nuclease sensitivity. In fact, most amide-linked bioactive polymers have been found to require intracellular lysosomal degradation for their activation.

Certain carbohydrate molecules are hydrolyzed in vivo, but their sensitivity to hydrolysis is also more difficult to manipulate than that of nucleotide components. Many non-biological polymers require uptake by macrophages or hepatocytes to be efficiently metabolized, and are also excreted unchanged in the urine. In contrast, nucleotide components, including a variety of relatively nuclease resistant nucleotide components not encountered in natural nuclease acids, are hydrolyzed by nucleases and other esterases in serum and tissue fluids.

Other Modifications of Nucleotide-Based Prodrugs

A polyalkyl glycol, such as polyethylene glycol (PEG) can be linked to a nucleic acid ligand component of the nucleotide-based prodrug after the ligand has been identified by the SELEX method to improve the pharmacokinetic properties of the nucleic acid ligand. U.S. patent application Ser. No. 08/434,465, filed May 4, 1995, entitled "Nucleic Acid Ligand Complexes", which is incorporated herein by reference, describes a method for preparing a therapeutic or diagnostic complex comprised of a nucleic acid ligand and a lipophilic compound or a non-immunogenic, high molecular weight compound and illustrates the improved pharmokinetic properties of nucleic acid ligands complexed to a PEG relative to the nucleic acid ligand alone. PEGylation of the nucleotide component of the nucleotide-based prodrugs of the present invention may retard absorption of the ligand into the capillaries.

Synthetic Methods

The nucleotide-based prodrugs of the present invention can be synthesized according to synthetic methods which couple a nucleotide component to a nucleoside analog or to a non-nucleoside drug which has a hydroxyl functional group.

Pharmacologically active purine and pyrimidine analogs may be incorporated as nucleotides into nucleotide components using standard oligonucleotide synthetic protocols. The nucleotide forms of these bases may be converted into phosphoramidites, which may be used in oligonucleotide synthesis. Exceptions include several chain terminating antiviral purine nucleoside analogs, which lack 3' hydroxyl groups. These drugs can be incorporated via their free hydroxyl groups to the 5' phosphate group at the end of a nucleotide component. Table 1 lists several purine and pyrimidine analogs that may be incorporated into nucleotide-based prodrugs. Most of the parent drugs have oncolytic, immunosuppressive or antiviral activities.

The nucleotide-based prodrugs of the invention comprising non-nucleoside drugs coupled to a nucleotide component are formed according to synthetic procedures which link a hydroxyl group of the a non-nucleotide drug to a phosphate group provided by the activated nucleotide, such as a phosphoramidite. In one embodiment of the invention, the drug is attached to a nucleotide component via a junctional phosphodiester bond by coupling a hydroxyl group on the active drug and a 5' phosphoramidite on a nucleotide component. In another embodiment, the drug is attached to a nucleotide component via a junctional phosphodiester bond by coupling a hydroxyl group on the active drug and a 3' phosphoramidite on a nucleotide component. Many 3' and 5' phosphoramidites are commercially available, or they may be synthesized by conventional methods known to those skilled in the art. Table 1 lists several non-nucleoside drugs that may be incorporated into nucleotide-based prodrugs.

Therapeutic Use of Nucleotide-based Prodrugs

The present invention also relates to the use of the nucleotide-based prodrugs. The nucleotide-based prodrugs of the present invention may be used for a variety of applications, including but not limited to local drug therapy applications involving anatomic sites that are accessible to the practitioner. Examples of the latter are cutaneous diseases, diseases of the oropharynx and the joints.

In one embodiment, photocrosslinkable nucleotide-based prodrugs (FIGS. 2D–F) may be used for local therapy, for example in dermatologic applications. One or more of the photocrosslinkable bases illustrated in FIG. 7 are incorporated into such nucleotide-based prodrugs. In one embodiment, nucleotide-based prodrugs may be applied locally in a topical drug formulation for example, to diseased skin. The drug may enter the diseased skin by passive diffusion, and it may be subsequently photocrosslinked to proteins or other macromolecules in the dermis and/or epidermis. In another embodiment, nucleotide-based prodrugs may be introduced via iontophoresis, whereby an electrical current is applied to the drug, and as a result the drug is driven into the skin lesion (Singh, J. and Roberts, M. S. (1989) *Drug Design and Delivery* 4:1–12). Certain nucleotide-based prodrugs may be administered using an adaptation of iontophoresis wherein the cornified layers of the epidermis are breached with sharp metallic bristles connected to an electrode that transmits electrical current into the skin. Subsequently, the nucleotide-based prodrug is photocrosslinked to proteins or other macromolecules in the dermis and/or epidermis.

In another embodiment, nucleotide-based prodrugs may be injected intravenously, and subsequently photocrosslinked to the skin by photochemotherapeutic methods known in the art, for example, using PUVA or a related procedure. The photocrosslinked nucleotide-based prodrugs comprise a reservoir of prodrug, which provides sustained release of active drug over a period of time. Examples of the clinical use of nucleotide-based prodrugs are provided in the Examples.

The dosage of nucleotide-based prodrugs for a mammal, including a human, may vary depending upon the extent and severity of the condition that is treated and the activity of the administered compound. The dosage of the nucleotide-based prodrug is determined by reference to the recommended dosages of the active agent, bearing in mind that in selecting the appropriate dosage in any specific case, consideration must be given to the patient's weight, general health, metabolism, age and other factors which influence response to the drug. Dosage levels for most commercially available therapeutic agents, as well as many agents that are being clinically investigated, are well established.

Formulations for oral ingestion are in the form of tablets, capsules, pills, ampoules of powdered active agent, or oily or aqueous suspensions or solutions. Tablets or other non-liquid oral compositions may contain acceptable excipients, vehicles, diluents, fragrances, or flavors known to the art for the manufacture of pharmaceutical compositions, to make the medication palatable or pleasing to use. The formulation can therefore include diluents, such as lactose or calcium carbonate; binding agents such as gelatin or starch; and one or more agents selected from the group consisting of sweetening agents, flavoring agents, coloring or preserving agents to provide a palatable preparation. Moreover, such oral preparations may be coated by known techniques to further delay disintegration and absorption in the intestinal tract.

Aqueous suspensions may contain the active ingredient in admixture with pharmacologically acceptable excipients, comprising suspending agents, such as methyl cellulose; and wetting agents, such as lecithin or long-chain fatty alcohols. The aqueous suspensions may also contain preservatives, coloring agents, flavoring agents and sweetening agents in accordance with industry standards. The preparations may further comprise antioxidants, such as ascorbic acid or tocopherol, and preservatives, such as p-hydroxybenzoic acid esters.

This invention will be more clearly understood with reference to the following non-limiting examples.

EXAMPLE 1

Nucleotide-based Prodrugs Comprising Nucleic Acid Ligands Containing Radiosensitizing Halopyrimidines One embodiment of the present invention provides therapeutic nucleotide-based prodrugs comprising nucleic acid ligands comprising nonradioactive halopyrimidine nucleoside analogs which act as radiosensitizers when exposed to an appropriate dose of externally applied X-irradiation (Szybalski, W. (1974) Cancer Chemother Rep. 58:539–557). In previous studies, radiosensitizers such as a halogenated pyrimidine have been administered to the patient via a systemic or local route of delivery (Hoshino, T. Radiosensitization of brain tumors. In Central Nervous System Tumors. Modern Radiotherapy and Oncology Series. Edited by T. J. Deeley. London. Butterworth. 1974; Kinsela et al. (1985) Int. J. Radiation Oncol. Biol. Phys. 11:1941; Levin, V. A. et al. (1990) Proc. Am Soc. Clin Oncol. 9:91). Halogenated pyrimidine nucleoside have been considered particularly promising, since they can be selectively taken up by proliferating malignant cells. Clinical trials have been undertaken to test bromo-deoxyuridine (BrdU) and iodo-deoxyuridine (IdU) in multiple tumors, including malignant astrocytomas. While the radiosensitization by halopyrimidines has been validated in vitro, it has been difficult to translate this information into clinical practice, because only a small fraction of an intravenously injected dose of halopyrimidines is taken up by the tumor cells.

Clearly it would be useful to have a method whereby halopyrimidines could be concentrated and retained in the tumor prior to the irradiation step. The present invention provides nucleic acid ligands which have properties uniquely suited for the delivery and release of radiosensitizing halopyrimidines into tumors. One embodiment of the present invention provides nucleotide-based prodrugs comprising nucleic acid ligands that bind to abundant macromolecules within the tumor, for example extracellular matrix proteins, and halopyrimidines. The nucleic acid ligand is identified by the SELEX procedure as described in the SELEX Patent applications (See also, Tuerk and Gold (1990) Science 249:505–510). 5-Bromodeoxyuridines may be incorporated into the nucleic acid ligand postSELEX, either as internal substitutions or as "tails" added onto the 3' and/or 5' ends.

One embodiment of this Example provides for the sustained release of the halopyrimidine nucleotides from the nucleotide-based prodrug, which takes place by hydrolysis of the nucleic acid ligand component or the prodrug which contains the halopyrimidine nucleotides. After the halopyrimidine nucleotides are released from the nucleic acid ligand, they are rapidly hydrolyzed by tissue nucleotidases, thereby yielding the pharmacologically active halopyrimidine nucleosides, which are taken up by tumor cells. In this embodiment, the halopyrimidine nucleosides are incorporated into the cell's nucleic acids.

Figure 4:
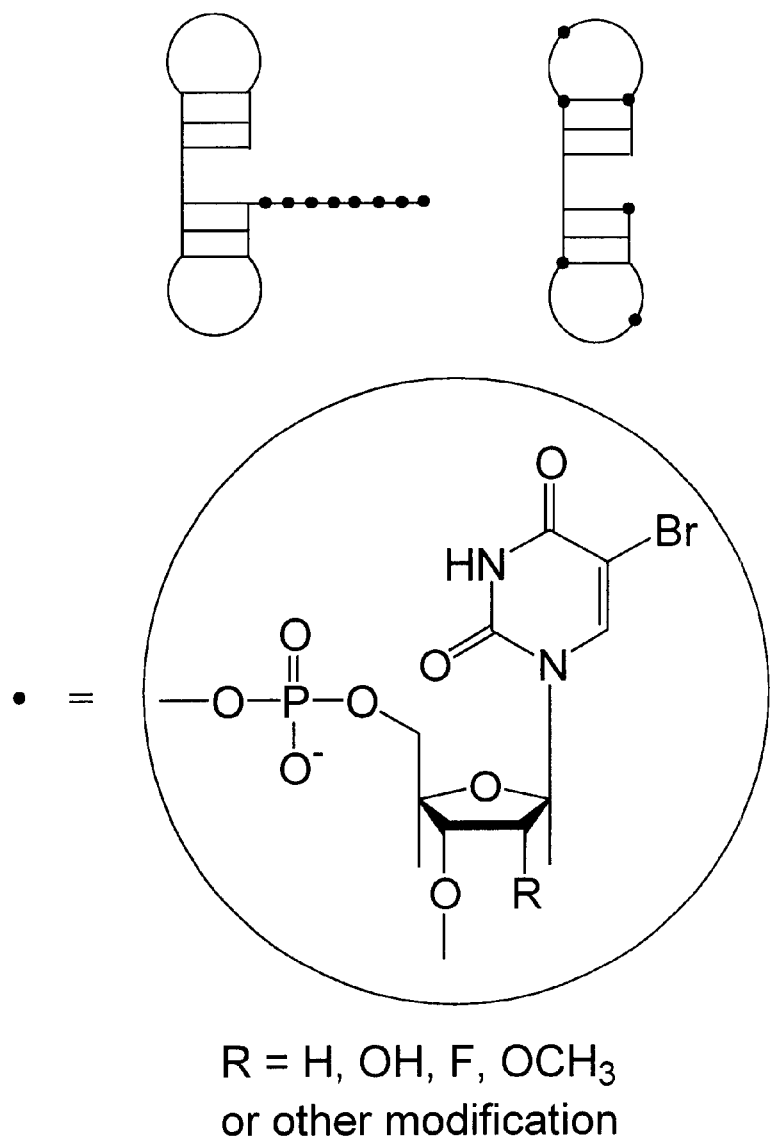
FIG. 4 illustrates one example of a radiosensitizing nucleotide-based prodrug comprising a nucleic acid ligand that binds to a target. In this example, the nucleotides in the radiolabeled polymer have 2'O-methyl ribose residues and phosphates containing $^{32}P$.

Another embodiment of this Example provides nucleotide-based prodrugs comprising nucleic acid ligands that are more resistant to tissue nucleases, for example nucleotide-based prodrugs comprising a nucleic acid ligand, wherein the nucleic acid ligand comprises 2'-OMe modified nucleotides in addition to the halopyrimidine nucleoside drug (FIG. 4). In this embodiment, the nucleic acid ligand containing one or many halopyrimidines remains anchored to the target, such as proteins or other macromolecules associated with the tumor, for a longer period during the irradiation phase of the treatment. In both of the above-mentioned embodiments, externally applied X-irradiation, or another type of radiation such as ultraviolet rays, activates the halopyrimidine, thereby magnifying the tissue-destructive properties of the irradiation (Szybalski, W. supra).

Nucleic acid ligands containing halopyrimidines are assembled on an ABI 394 DNA/RNA synthesizer using established ribonucleic acid synthesis chemistry protocols, such as methods using 2'-O-silyated ribonucleosides, and 3'O-Phosphoramidites on controlled pore glass supports (Usman, N., et al. (1987) J. Am. Chem. Soc. 109, 7845–7854; Sinha, N. D., et al. (1993) Biochemie 75, 13–23; Reddy, M. P., et al. (1994) Tetrahedron Letters 35, 4311–4314), with t-butyl phenoxyacetyl 2 and acetyl 3 nucleoside protecting groups. The oligonucleotides are cleaved and deprotected with 1.0 ml of $NH_4OH$ per μmole support at 55° C. for 2 hours. The support is filtered and rinsed with 50/50 ethanol:water and dried. The TBDMS groups are removed with 1.5 ml of 1M tetrabutylammonium fluoride (TBAF) in THF per μmol of oligonucleotide at room temperature for 24 hours. The TBAF solution is quenched with an equal volume of 1.0 M Tris; 2 mM EDTA; pH 7.0. Samples may be desalted by size exclusion chromatography. 5-BrdU phosphoramidites are available commercially from any number of suppliers (e.g., Glen Research, Inc. Sterling, Va.). 5-BrU phosphoramidites with 2' modifications on the ribose ring (e.g., 2' O-methyl or 2' Fluoro) can be synthesized using standard chemical protocols.

The above mentioned agents may be delivered by methods known in the art, including the intravenous, intra-arterial, direct installation, direct injection, iontophoresis, intracavitary and intrathecal routes. In the case of solitary brain tumors, a preferred delivery method is convection delivery, whereby a solution of the radiotherapeutic agent is pumped directly into the edematous zone of the tumor mass (Bobo, R. H. et al. (1994) *Proc. Natl. Acad. Sci.* 91:2076–2080), but intra-arterial and systemic routes of administration are also possible. In the case of head and neck carcinomas, the nucleic acid ligand may be directly injected into the tumor hours to days before radiotherapy. This embodiment of the invention is novel, because it provides a highly efficient means by which to concentrate and retain the halogenated pyrimidine radiosensitizers in the immediate vicinity of the tumor cells and neovessels.

EXAMPLE 2

Nucleotide-based Prodrugs Comprising Radiotherapeutic Nucleic Acid Ligands Containing $^{32}P$ The present invention provides for methods for delivering nucleotide-based prodrugs comprising nucleic acid ligand components and pharmacologically active drugs and/or tissue-destructive radionuclides (i.e., radioactive molecules) to neoplastic tissues, wherein the nucleic acid ligand serves to precisely anchor the prodrug directly onto the malignant cell surface. Alternatively, the prodrug may be anchored in the immediate vicinity of the tumor cells, such as in the tumor stroma or in the immediate vicinity of the tumor neovessels.

In one embodiment of the present invention, the nucleotide-based prodrug comprises a nucleic acid ligands comprising tissue-damaging radionuclides. This embodiment of the invention may be applied to the treatment of various types of malignant neoplasms arising in different sites throughout the body, but it is best described in the context of a specific type of tumor, for example, a malignant brain tumor. Malignant astrocytomas arise from astrocytic glial cells in the brain (deGirolami, U. et al. *Pathology of the Central Nervous System*. In: Robbins Pathologic Basis of Disease. Fifth Edition. Edited by T. J. R. Cotran. Philadelphia. W. B. Saunders and Co. 1994). Astrocytomas nearly always form a single mass lesion and they rarely if ever metastasize to sites outside of the central nervous system. It is widely accepted that prolonged survival would result if an effective local control of the tumor could be achieved. Nucleotide-based prodrugs comprising radionuclides may be introduced by appropriate routes into malignant tumors, such as astrocytomas, where they are expected to bind to proteins and/or other macromolecules in the tumor. These nucleotide-based prodrugs are expected to induce cytocidal effects on the tumor cells and/or the tumor associated neovasculature. Before describing these radiopharmaceutical agents, their mechanism of action, and their novel features, it is necessary to briefly review the histopathological features of a tumor such as malignant astocytoma and the current therapies used to treat these brain tumors.

High grade malignant astrocytomas are comprised of anaplastic malignant astrocytes with a high proliferative rate, and they have prominent neovessels (Girolami, U. et al. *The Central Nervous System* In Robbins Pathologic Basis of Disease. Fifth Edition. T. J. R. Cotran, Ed. Philadelphia. W. B. Saunders and Co. 1994). Eventually growth outpaces neovascularization resulting in necrosis, which is particularly prominent in the center of the most aggressive tumors called glioblastoma multiforme. Another consistent histological feature is the abundant deposition of extracellular matrix, including proteins such as tenascin-C, a protein secreted by the malignant astrocytes (Zagzag, D. et al. (1995) *Cancer Research* 55:907–914; Castellani P. et al., (1995) *Acta Neurocir.* 136:44–50). Tenascin-C is deposited in the immediate vicinity of the tumor cells, but it is most abundant in a cuff-like distribution around the intratumoral blood vessels. Tenascin-C is also overproduced by many different types of tumors, including malignancies of the breast, lung, colon and prostate (Leprini, A. et al. (1994) *Perspectives on Dev. Neurobiol.* 2:117–123; Erickson, H. P. et al. (1989) *Ann. Rev. Cell Biol.* 5:71–92; Chiquet-Ehrismann, R. (1990) *FASEB J.* 4:2598–2604; Chiquet-Ehrismann, R. (1995) *Experientia* 5:853–862).

Although malignant astrocytomas do not metastasize, the cells have a highly infiltrative pattern of growth, so complete surgical resection is not possible (Prados, M. D. and Wilson, C. B. *Neoplasms of the Central Nervous System* pp. 1481–1488. In: Cancer Medicine 4th Edition. Holland et al. Ed. Williams and Wilkins. 1997). Current standards of care in the United States call for the surgical removal of a central region of the tumor (i.e., the so-called "apple core") of the astrocytoma followed by radiotherapy to destroy the residual malignant cells, which are inevitably left behind in an irregular edematous zone at the periphery of the tumor. Approximately 80% of tumor recurrences arise within a 2-cm deep peripheral margin of residual infiltrative tumor tissue. Not surprisingly, patient survival correlates directly with the quantity of tumor tissue left behind in the peripheral zone. Destruction of the infiltrating malignant cells in this peripheral zone is the key problem facing neuro-oncologists.

Surgery followed by brain irradiation increases survival in these patients compared to surgery alone, and radiotherapy has impacted survival more than any other modality (Prados, M. D. supra). Whole brain irradiation offers no survival advantage compared to X-rays directed at the tumor mass, so there has been an increasing trend to localize radiotherapy. Conformal radiotherapy is a technique whereby malignant astrocytomas having highly irregular borders are exposed to X-rays projected in a pattern that matches as closely as possible the three dimensional contours of the tumor. But when the X-rays are directed at the tumor mass there is a risk of radiation necrosis especially above the dose of 60 Grays. Another local radiotherapy technique, "interstitial brachytherapy" (Liebel, S. A. et al. (1989) *Int. J. Radiat. Oncol. Biol. Phys.* 17:1129–1137), involves the insertion of radioactive (e.g., $^{125}I$) pellets into the postsugical cavity.

Clearly, malignant astrocytomas do respond to radiotherapy, but there is a great need for improved methods to precisely direct the radiation to the highly infiltrative malignant astrocytes in the peripheral zone of the tumor, while sparing the surrounding tissue as much as possible. It would be useful to have a radiotherapeutic method whereby the malignant astrocytes and/or tumor neovessels are subjected to a precisely localized and more protracted dose of irradiation. By avoiding rapid tissue destruction, one avoids the induction of acute myelotoxicity, necrosis and hemorrhage which may be fatal.

Nucleotide-based prodrugs comprising nucleic acid ligands directed at tumor and/or neovessel-associated macromolecules, for example tenascin-C, have unique properties required to precisely localize radionuclides and other radiotherapeutic agents in the tumor, and to provide a more protracted dose. As described below, these nucleotide-based prodrugs provide more therapeutic options than are afforded by other methods such as radiotherapeutic antibodies. For example, SELEX may be used to generate the nucleic acid ligand component of the nucleotide-based prodrugs that bind tenascin-C with high affinity. Similar experiments may be undertaken to create nucleic acid ligands which bind to tumor-associated macromolecules besides tenascin-C, which is only used as an example of this embodiment. U.S.

patent application Ser. No. 08/434,425, filed May 3, 1995, entitled "Systematic Evolution of Ligands by EXponential Enrichment: Tissue SELEX", which is incorporated herein by reference, describes a method for identifying nucleic acid ligands to tissues.

The tissue distribution and residence time of the nucleic acid ligands may be determined by standard imaging and/or autoradiographic techniques performed on xenografted glioblastoma tumors. High affinity nucleic acid ligands are then modified by postSELEX procedures to create nucleotide-based prodrugs carrying radiotherapeutic nuclides as described below. The localizing ability, efficacy and toxicity of such radioactive ligands may be tested using the glioblastoma xenograft models as well as orthotopic glioblastoma models.

The most effective therapeutic radionuclides emit high energy β-particles that maximize self irradiation of tumor cells, and minimize the exposure of non-target cells which are outside of the region of diseased tissue (Harber, J. C. (1987) *Nuclear Medicine Therapy* New York; Thieme, pp. 321–322; Adelstein, S. J. et al. (1995) Radiobiology. In: Principles of Nuclear Medicine. $2^{nd}$ Edition. Edited by Wagner, Szabo and Buchanan. pp. 102–103.). Unfortunately, it is difficult to attach the most useful of these isotopes to antibodies. $^{131}$I has a half life of 8 days and it emits several β-particles, including one relatively strong one ($E_{max}\beta$=0.61 MeV), and only a few moles of iodine can be attached to each antibody. $^{32}$P emits much higher energy β-particles ($E_{max}\beta$=1.71 MeV; $E_{ave}\beta$=0.70 MeV) and it has a half life of 14.3 days. It would be useful to have a method by which $^{32}$P could be concentrated in the immediate vicinity of malignant cells and neovessels of tumors, but there is currently no efficient way to attach $^{32}$P to antibodies. Nucleotide-based prodrugs comprising nucleic acid ligands are equipped to deliver $^{32}$P to tumor associated macromolecules, for example, tenascin-C. $^{32}$P can be directly incorporated into the nucleic acid component of the the prodrug as the phosphorous atom within the nucleotides, and significantly, many moles of $^{32}$P can be incorporated into each ligand, thereby providing potent radiopharmaceutical agents (FIG. 5).

The above mentioned embodiment provides $^{32}$P-enriched tails that relatively resistant to nuclease attack, thereby avoiding the diffusion of radioactivity from the tumor lesion. For example, nuclease resistance may be conferred by incorporating 2'-modified nucleotides, such as 2'-fluoro or 2'-O-mehtyl nucleotides into the nucleic acid ligand component of the nucleotide-based prodrug. When these nucleotide-based prodrugs are bound to tumor cells or tumor cell associated stroma (e.g., tension-C), the β-particles emitted by $^{32}$P will inflict the damage to cells within less than 3.5 mm from the tissue-bound $^{32}$P-source. Significantly, maximal damage will be inflicted to cells less than half of a millimeter (~50–100 cell diameters) away from the tissue anchored $^{32}$P-labeled aptamer (Harber, J. C., supra). Examples of this embodiment are illustrated in FIG. 5.

In another embodiment, α-[$^{32}$P] nucleotides are incorporated into the nucleic acid ligand component of a nucleotide-based prodrug via an enzymatic (i.e., T7 polymerase, T3 polymerase or terminal transferase) reaction. In another embodiment, nucleic acid ligand components containing [$^{32}$P] nucleotides are assembled using established ribonucleic acid synthesis chemistry protocols (Usman, N. et al., supra, Sinha, N. D., supra; Reddy, M. P., supra). The latter synthesis method calls for [$^{32}$P] -containing phosphoramidites, which may be synthesized by methods known in the art such as that described by Beaucage and Caruthers, (1981) *Tetrahedron Lett.* 22:1859–1862.

The nucleotide-based prodrugs comprising $^{32}$P labeled nucleic acid ligands may be delivered by methods known in the art, including the intravenous or intraarterial routes, or by direct installation, including intracavitary and intrathecal routes. In the case of solitary brain tumors, a preferred delivery method is "convection delivery," whereby a solution of the radiotherapeutic agent is pumped directly into the edematous zone of the tumor mass (Bobo, R. H. supra), either pre- or postoperatively. $^{32}$P labeled nucleic acid ligand may find many applications in oncology, including the treatment of head and neck carcinomas, liver metastases and ovarian carcinomatosis. In the latter case, the radiotherapeutic nucleic acid ligand is introduced into the body cavity via a catheter. Intra-arterial administration may also be used to treat certain tumors, such as hepatic metastases from colorectal carcinomas.

EXAMPLE 3

Nucleotide-Based Prodrugs Comprising Nucleic Acid Ligands Containing $^{125}$I-Labeled Pyrimidines Radionuclide therapy is almost completely based upon isotopes that emit β-particles. $^{125}$I emits primarily γ photons, which are highly penetrating and do not effectively damage tissue in the immediate vicinity of the radiation source. But $^{125}$I can effectively kill cells via Auger electron emissions, low energy electrons that are only effective when the radionuclide is within 5–10 nm of the cell's DNA (Adelstein, S. J. supra). However, most cells are 10–20 mm in diameter and their nuclei are ~5 nm in diameter—dimensions 1000-fold beyond the effective range of Auger emissions. Clearly, efficient cell killing by Auger emissions requires the radionuclide to be concentrated in the cell nucleus.

Antibodies cannot gain access to the cell cytoplasm, much less the nucleus, so the Auger-emissions produced by antibody-bound 125I cannot effectively kill cells in the immediate vicinity of the isotope. The present invention provides methods for creating novel radiotherapeutic nucleotide-based prodrugs comprising nucleic acid ligands components, which can efficiently deliver radiohalogentated pyrimidines to malignant cells in vivo. According to one embodiment of the inveniton, the nucleic acid ligand components of the prodrug are labeled with $^{125}$I-containing deoxynucleotides. The sustained release properties of the nucleic acid ligand component provides a method to exploit the destructive power of Auger low energy electrons emitted by halopyrimidines, for example, 5-$^{125}$I dexoyuridylic acid (thymidine analog).

As tissue anchored ligands containing 5-$^{125}$I dexoyurdylic acid are hydrolyzed, the neighboring cells will take up the resulting radioactive nucleosides, which are phosphorylated inside of the cells and subsequently incorporated into chromosomal DNA. Auger emissions produced by halogenated pyrimidines within the DNA efficiently damage chromosomes.

Another advantage of nucleotide-based prodrugs comprising nucleic acid ligand components over antibodies is that several moles of 5-$^{125}$I dexoyuridylic acid can be incorporated into each nucleic acid ligand, thereby maximizing specific activity. Thus, the nucleic acid ligand components have tumor localizing properties similar to antibodies, but their ability to supply the surrounding cells with halogenated pyrimidines distinguishes them from antibodies. To ensure that the radioactive halogen is incorporated into high molecular weight DNA, the $^{125}$I enriched tails might be synthesized as deoxynucleotides. In another embodiment, $^{131}$I- labeled pyrimidines are incorporated into the nucleic acid ligand components. $^{125}$I- and $^{131}$I-labeled nucleic acid ligands may be delivered by methods known in the art (see Examples 1 and 2).

Radioactive halogenated pyrimidines such as 5-$^{125}$I dexoyuridylic acid may be incorporated into the ligand as a postSELEX modification using a variety of nucleotide polymerases, or using established ribonucleic acid synthesis chemistry protocols (Usman, N. supra; Sinha, N. D., supra; Reddy, M. P. supra). The latter synthesis method calls for [$^{125}$I]-containing pyrimidine phosphoramidites, which may be synthesized by methods known in the art such as that described by Beaucage and Caruthers, (1981) *Tetrahedron Lett.* 22:1859–1862.

EXAMPLE 4

Nucleotide-Based Prodrugs Containing Oncolytic Nucleoside Analogs

Figure 6:
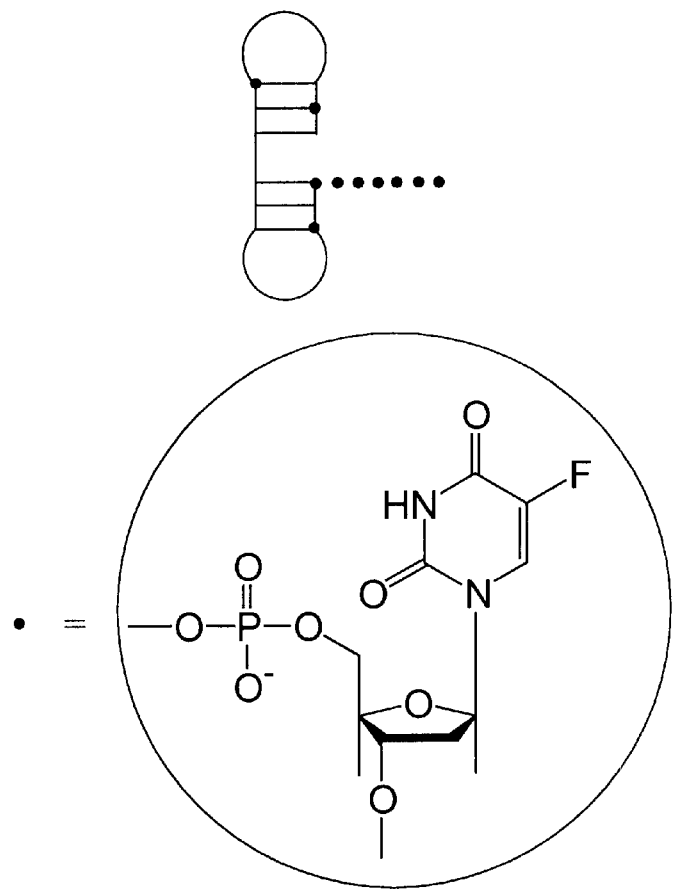
FIG. 6 illustrates one example of a nucleotide-based prodrug comprising a nucleic acid ligand containing an oncolytic nucleoside analog, in this case 5-fluorodeoxyuridine (5-FdU).

Another embodiment of the present invention provides nucleotide-based prodrugs comprising nucleic acid ligands comprising pharmacologically active nucleoside analogs, which are activated and released by hydrolysis of one or more junctional phosphodiester bonds in the prodrug. Hydrolysis of the nucleic acid ligand component initially releases 3' and/or 5' nucleotides, which are subsequently converted to nucleosides that can be taken up by tumor cells in the immediate vicinity of a prodrug reservoir. For example, a nucleotide-based prodrug comprising a nucleic acid ligand containing one or more 5'-fluorodeoxynucleotides is anchored to a macromolecule, for example a protein, in a diseased tissue. The release and activation of 5-fluodeoxyruridine is mediated by tissue nucleases and phosphodiestrases that celasve the nucleic acid lignad. 5-Fluodeoxyruridine nucleotides may be inserted on the 3' and/or 5' end of the nucleic acid ligand, or they may be substituted for nucleotides in the ligand, provided that the substitutions do not disrupt the ligand's binding ability. Many moles of 5'-fluorodeoxynucleotide may be delivered and released from each prodrug molecule. An example of a nucleotide-based prodrug comprising a nucleic acid ligand comprising 5-fluodeoxyruridineis illustrated in FIG. 6.

In the above mentioned embodiment, the SELEX method is used to identify the nucleic acid ligand to tumor-associated proteins, including membrane proteins on the tumor cells, as well as extracellular matrix proteins, which are organized into structures such as basement membranes, stromal matrix and perivascular cuffs.

The nucleic acid ligands containing oncolytic nucleoside analogs are assembled as described in Example 1. 5-F-Uridine phosphoramidites are available commercially from a number of suppliers(e.g., Glen Research, Inc. Sterling, Va.). 5-FU phosphoramidites with 2' modifications on the ribose ring (e.g., 2'-O-methyl or 2'-Fluoro) may be synthesized using standard chemical protocols.

Nucleotide-based prodrugs comprising nucleic acid ligands containing pharmacologically active nucleoside analogs with oncolytic activity may be used for many types of malignant neoplasms, including carcinomas, sarcomas, lymphomas, leukemias and other hematopoietic neoplasms. This class of prodrugs may also be used for certain pre-neoplastic conditions and benign tumors such as keratoses and warts. This class of prodrugs may be deliverd by methods known in the art, including the intravenous, intra-arterial, intracavitary, intrathecal and topical routes. This embodiment of the present invention is novel, because it provides a unique oncolytic drug delivery system whereby the prodrug serves as a tissue anchor which restricts the volume of drug distribution, but it also serves as the drug depot. Most importantly, the ability to chemically manipulate the rate of hydrolysis of covalent bonds within the nucleic acid aptamers provides a novel controlled release mechanism that is not afforded by other classes of prodrugs.

EXAMPLE 5

Photocrosslinkable Nucleotide-Based Prodrugs Containing Oncolytic Nucleotide Analogs for the Treatment of Hematopoietic Neoplasms One embodiment of the present invention provides photocrosslinkable prodrugs comprised of nucleic acid ligands containing oncolytic nucleoside analogs, which are activated and released by hydrolysis of one or more junctional phosphodiester bonds in the prodrug. In a preferred embodiment, the prodrugs are photocrosslinked to malignant blood cells, for example leukemic cells, using a method commonly referred to as extracorporeal photopheresis, an ex vivo therapeutic procedure whereby blood cells are removed from the body, incubated with a drug and then exposed to a source of ultraviolet light suitable for photocrosslinking the drug to the cells. The viable malignant cells are returned to the systemic circulation.

The photocrosslinked malignant blood cells recirculate continuously to tissue compartments that are frequented by such cells. In these compartments, hydrolysis of the prodrug initially releases 3' and/or 5' nucleotides, which are subsequently converted to nucleosides that can be taken up by other cells in the immediate vicinity of the prodrug reservoir. This approach would be particularly well-suited for treated lymphoid neoplasms which are tropic for one or more target organs, for example the spleen, lymph nodes or skin.

An example of the above mentioned embodiment would be to incorporate nucleoside analogs into the nucleotide-based prodrug that are active against hematopoietic neoplasms, for example, deoxycoformycin, cladribine or cytosine arabinoside. These nucleoside drugs are active in chroninc lymphocytic leukemia, hairy cell leukemia and other leukemias and lymphomas (O'Dwyer P. J. et al. (1988) *Ann. Intern. Med.* 108:733–43; Beutler, E. (1992) *Lancet* 340:952–956; Chabner, B. A. et al. (1996) *Antineoplastic Agents*. In: Goodman and Gilman's The Pharmacological Basis of Therapeutics, Ninth Edition. (Hardman, Limbird, Molinoff, Ruddon, and Gilman Eds). McGraw-Hill. United States of America. pp. 1233–1287). Both inhibit adenosine deaminase, a purine salvage enzyme that catalyzes the conversion of adenosine ribonucleoside to inosine ribonucleoside. Adenosine deaminase does not appear to recognize the 2' position of the ribose ring, since it is strongly inhibited by deoxycoformycin, a deoxyribonucleoside. Therefore, ribonucleotides, deoxyribonucleotides and various 2' modified ribonucleotide derivatives of deoxycoformycin may retain activity against this enzyme. Examples of prodrugs containing deoxycoformycin (Woo, P. W. et al. (1974) *J. Heterocyclic Chem.* 11:64) and cladribine (Estey, E. H. et al. (1992) *Blood* 79:882–887; Beutler, E. supra) are illustrated in FIG. 8. An example of a nucleotide-based prodrug comprising a nucleic acid ligand containing cytosine arabinoside nucleotides is shown in FIG. 9.

The above mentioned embodiment utilizes cell surface associated proteins as targets of the nucleic acid ligand components of the nucleotide-based prodrugs. The protein need not be specific for malignant cells, although this may be the optimal situation. The most important requirement is that the protein is expressed on the malignant cells, and that photocrosslinking does not activate or adversely affect the cell. The novelty of this embodiment of the invention is that the cells carry the prodrug to selected sites in the tissues, where their malignant counterparts are exposed to the active agent released from the prodrug.

Aptamers containing oncolytic nucleoside analogs are assembled as described in Example 1. A variety of cladribine and 4-thiouracil containing phosphoramidites may be synthesized using standard chemical protocols.

EXAMPLE 6

Figure 10:
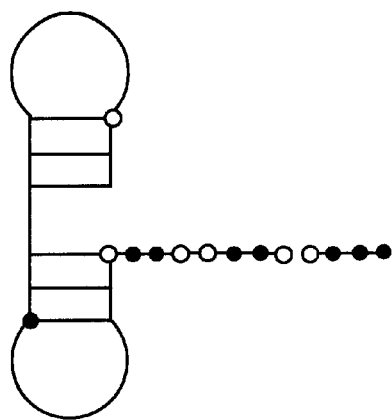
FIG. 10 illustrates one example of a nucleotide-based prodrug comprising a nucleic acid ligand containing a copolymeric "tail" comprised of two pharmacologically active purine nucleoside analogs, in this case the immunosuppressive drugs 6-mercaptopurine and 2'-deoxycoformycin. The nucleic acid ligand is selected for its ability to bind to a cell or tissue macromolecule, thereby providing a local reservoir of prodrug. Hydrolysis of the junctional phosphodiester bonds releases 6-mercaptopurine and deoxycoformycin thereby providing local immunosuppression.
Figure 11:
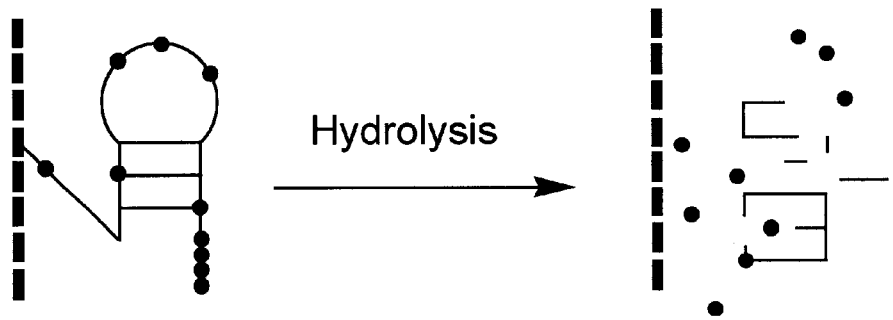
FIG. 11 illustrates the concept of sustained drug release from a non-aptameric nucleotide-based prodrug polymer. The intact nucleotide-based prodrug is bound to a poorly diffusible macromolecule, thereby providing a reservoir of nucleoside analog drug molecules that may be activated and released as the nucleotide component of the prodrug is hydrolyzed by tissue nuclease and/or esterase activities.
Figure 11:
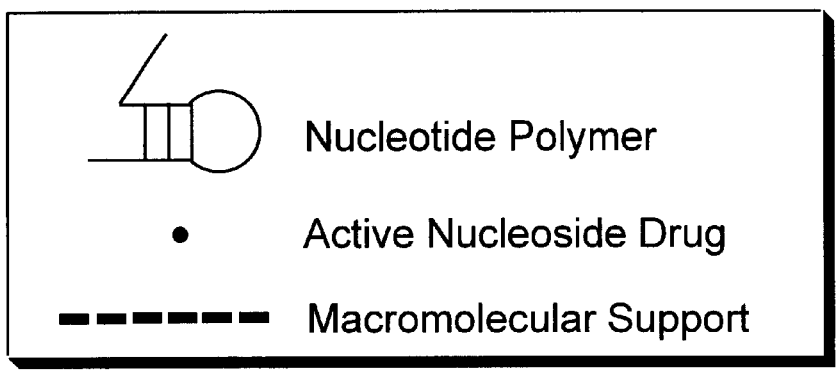

Nucleotide-Based Prodrugs Comprising Nucleic Acid Ligands Containing Immunosuppressive Nucleoside Analogs One embodiment of the present invention provides nucleotide-based prodrugs comprising nucleic acid ligands containing immunosuppressive nucleoside analogs that are released and activated by the hydrolysis of junctional phosphodiester bonds coupling the immunosuppressive nucleoside analog(s) to a nucleotide component (Skipper, H. E. (1954) N. Y. Acad. Sci. 60:315; Elion, G. B. (1967) Fed. Proc. 26:898–999; Snow, J. L. et al. (1995) J. Am. Acad. Dermatol. 32:114–116). An example of a nucleic acid ligand prodrug containing immunosuppressive nucleoside analogs is illustrated in FIG. 10. In this example, two immunosuppressive agents, each with a different mechanism of action, are incorporated into the nucleic acid ligand which has the ability to bind to macromolecules such as extracellular matrix proteins that are abundantly expressed in the diseased tissue. The immunosuppressive prodrug illustrated in FIG. 10 may be used to treat autoimmune diseases that manifest themselves in localized regions of the body, for example psoriasis. Before describing how the drug might be used to treat psoriasis, it is necessary to provide a brief description of this disease.

A thickened epidermis is the most outstanding pathological and clinical feature of psoriasis, but the primary defect is the underlying dermis (Murphy, G. et al., (1994) The Skin, In Robbins Pathologic Basis of Disease. Fifth Edition. Edited by T. J. R. Cotran. Philadelphia. W. B. Saunders and Co.). Current evidence strongly suggests that keratinocyte proliferation and neutrophilic infiltration are reactive processes, and the true culprits are cytokine-producing lymphocytes and monocytes that have migrated into the underlying dermis. Three important pathological features are observed in psoriatic dermis. First, heavy infiltrates of mononuclear cells, including a predominance of CD4+ helper T-cells, are present in the dermal papillae and reticular dermis. Second, the dermal papillae are hypervascular and extend nearly to the surface of the skin. In fact, the epidermis is abnormally thin over the dermal papillae, a histological feature that explains why psoriatic skin is more permeable to topically applied drugs than normal skin, and why minor trauma induces dot-like hemorrhages on the surface of psoriatic plaques; each hemorrhage is a sheared papilla. Third, the dermal zone immediately beneath the epidermis has certain biochemical hallmarks of reparative connective tissue, including abundant deposits of tenascin-C, an extracellular matrix protein (Lightner, V. A. (1994) J. Invest. Dermatol. 102:273–277). Psoriasis is an excellent candidate for sustained release local drug therapy, because the offending cells are highly concentrated in a small volume of accessible tissue, and multiple active drugs are available, but their narrow therapeutic indices preclude effective systemic therapies.

The present invention provides a means by which potent immunosuppressive drugs may be concentrated and slowly released into the dermis, in the immediate vicinity of the abnormal immune cell infiltrate, which are particularly dense in the papillary dermis (upward projections) and in a 50–100 mm zone of superficial reticular dermis just beneath the dermoepidermal junction. A nucleotide-based prodrug comprising an immunosuppressive nucleoside analog that binds with high affinity to an abundant macromolecule, for example a dermal extracellular matrix protein, would produce a concentrated gradient of immunosuppressive nucleoside analog in the vicinity of the target. The goal is to load this subepithelial microdomain with a sufficient amount of prodrug to last for several weeks. Preferably, the diffusion of the drug would be uniform, exposing the entire affected dermis. The nucleotide-based prodrug formulation would be completely free of bulk resins and polymers, and it would not displace any dermal tissue. Preferably the drug formulation would be 100% biocompatible, and the drug and the excipients would be resorbed without a trace.

The above-mentioned nucleotide-based prodrug may be delivered by any method known in the art, including the intravenous route, intralesional injection, intracavitary installation, passive topical application or iontophoretic methods, or adaptations of iontophoretic methods (Singh, J. supra). In one embodiment, it may be desirable to reduce the skin's resistance to the electric current, which drives the nucleotide-based prodrug into the cutaneous lesion. This may be accomplished by the use of a brush-like electrode capable of producing many tiny puncture sites through the cornified layers of epithelium overlying the pathological lesion. The efficiency of iontophoresis would be determined by the electrode bristles' size, sharpness, number and spatial arrangement. The immunosuppressive prodrug may be applied in a viscous, buffered, aqueous electrolyte solution which provides for optimal electrophoresis into the skin. The novelty of the present invention lies in the sustained release properties of the nucleotide-based prodrugs, thereby providing a means of using small doses and infrequent drug applications. The advantage of infrequent drug applications minimizes the inconvenience and expense associated with the use of invasive modifications of the iontophoretic method. In other embodiments of the invention, immunosuppressive prodrugs are delivered via the intravascular route to treat immunologically mediated diseases characterized by activated endothelial cells, which express a host of inducible cell surface proteins such as type II histocompatability antigens, vascular cell adhesion molecule (VCAM) and intercellular adhesion molecule (ICAM). According to these embodiments, the nucleic acid ligand component of the prodrug binds to proteins that are specifically expressed on the activated endothelial cell surface, thereby allowing the nucleotide-based prodrug to be targeted to the desired site. In yet another embodiment of the invention, nucleotide-based prodrugs are delivered to the liver and spleen, which avidly and efficiently remove non-PEGylated nucleotide components from the bloodstream. The above-mentioned nucleotide-based prodrugs may be used for many diseases of autoimmune, or presumed autoimmune etiology, including but not limited to psoriasis, atopic eczema, lichen planus, lupus erythematosus, rheumatoid arthritis and inflammatory bowel disease.

Nucleic acid ligands containing immunosuppressive nucleoside analogs are assembled as described in Example 1. Immunosuppressive nucleoside analogs are not presently commercially available. However, phosphoramidites containing 6-mercaptopurine or deoxycoformycin may be synthesized using standard chemical protocols.

EXAMPLE 7

Figure 14:
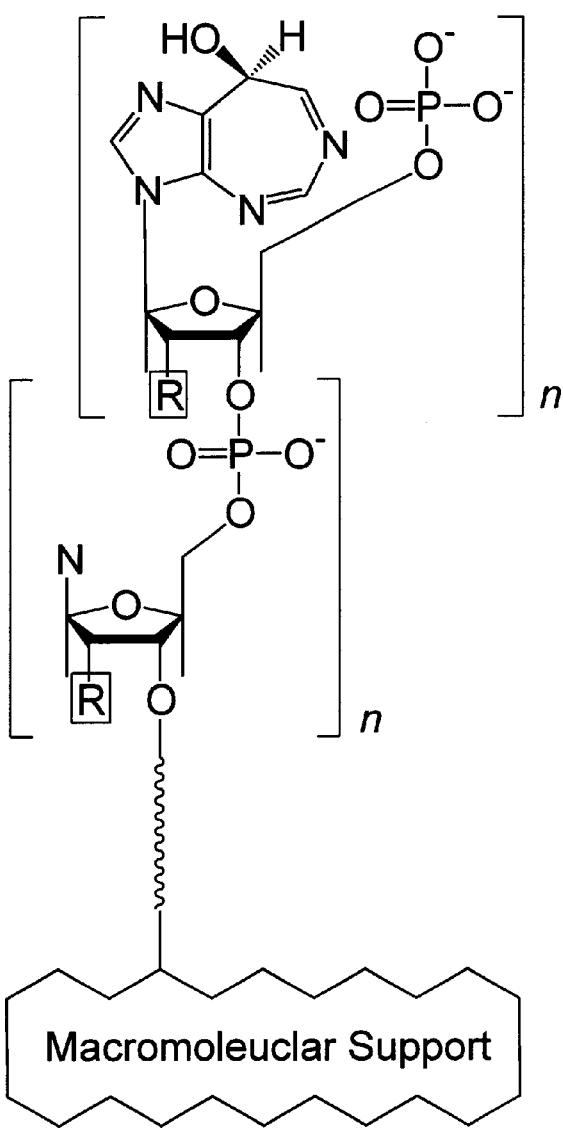
FIG. 14 illustrates an example of a nucleotide-based prodrug comprising one or more pharmacologically active nucleoside analogs—in this case 2'-deoxycoformycin nucleotides—as a contiguous block of nucleotides in the prodrug polymer. The deoxycoformycin polymer is attached to an anchoring nucleotide, which in turn is attached to a poorly diffusible macromolecular support via a nuclease-resistant phosphodiester bond including a 2'-O-methyl ribose sugar.

Non-Aptameric Nucleotide-Based Prodrugs Containing Immunosuppressive Nucleoside Analogs It would be useful for certain clinical applications to have nucleotide-based prodrugs comprising small molecule immunosuppressive nucleoside analogs with the ability to be sequestered in tissue compartments, wherein active nucleoside analogs are released into the diseased tissue. One embodiment of the present invention provides nucleotide-based prodrug polymers comprised of 25 or fewer nucleotides. Such prodrugs are comprised of one or more nucleotides that are attached covalently to macromolecular supports, preferably biocompatible polymers, that reduce the rate of diffusion of the prodrug or the active drug component of the prodrug in the tissues. Such prodrugs also have one or more nucleotide analogs that are converted to immunosuppressive drugs after being released and activated by the hydrolysis of junctional ester bonds (FIG. 12). An example of this embodiment of the invention is illustrated in FIG. 14, where the immunosuppressive nucleoside drug is deoxycoformycin (O'Dwyer P. J. supra; Chabner, B. A. supra). In FIG. 15, two immunosuppressive nucleoside analogs, in this particular example, deoxycoformycin and 6-mercaptopurine, are incorporated into a single prodrug polymer. Any pharmacologically active nucleoside analog may be used in this embodiment, including the drugs listed in Tables 1 and 2.

Non-aptameric oligonucleotides are assembled as described for nucleic acid ligands using established ribonucleic acid synthesis chemistry protocols, and as methods using 2'-O-silyated ribonucleosides, and 3'-O-Phosphoramidites on controlled pore glass supports as described in Example 1, with t-butyl phenoxyacetyl 2 and with acetyl 3 nucleoside protecting groups. Addition of an oligonucleotide to a macromolecular support (e.g., any polymer with appropriate functional groups) can be achieved by direct conjugation of the macromolecular support may support phosphoramidite. Alternatively, the macromolecular support may be derivatized to create a solid phase phosphoramidite, which may be combined to the appropriate nucleotide or nucleotide chain. The choice of a macromolecular support is dictated by the particular application, but one may choose from a vast array of biocompatible, biodegradable polymers such as: poly-lactic acid (PLA), poly-glycolic acid, poly($\epsilon$-caprolactone), poly ($\beta$-hydroxybutyrate), poly-poly($\beta$-hydroxyvalerate), polydioxanone, poly(ethylene terephthalate), poly(malic acid), poly(tartronic acid), poly(ortho esters), polyanhydrides, polycyanoacrylates, poly(phosphoesters), polyphosphazenes, hyaluronidate, polysulfones, polyacrylamides, polymethacrylate, CarboPol, hydroxyapaptite, chimeric recombinant elastin-silk protein (Protein Polymers, Inc) and collagen (Matrix Pharmaceuticals, Inc) (for detailed discussion of the above mentioned polymers, see: Park, K. et al. (1993) Biodegradable Hydrogels for Drug Delivery. Technomic Publishing Co., Inc. Lancaster, Pa.).

In a preferred embodiment for cutaneous diseases, the above-mentioned nucleotide-based prodrugs are introduced into the skin lesion by iontophoresis, or a modification of established iontophoretic methods. For example, one may use iontophoresis or an adaptation of iontophoretic methods known in the art. In one embodiment, the prodrugs may be passively introduced into the skin via the topical route. In certain embodiments, the affected skin is exposed to ultraviolet light after the drug is administered thereby fixing the prodrug in the diseased tissue. Alternatively, the prodrugs may be directly injected into or below the skin lesion. The novelty of the present invention lies in the sustained release properties of the prodrugs, thereby allowing small doses and infrequent drug applications. The above mentioned immunosuppressive prodrugs may be used for many diseases of autoimmune, or presumed autoimmune etiology, particularly diseases affecting superficial tissues, such as psoriasis, atopic eczema, lichen planus, lupus erythematosus and inflammatory bowel disease.

EXAMPLE 8

Figure 16:
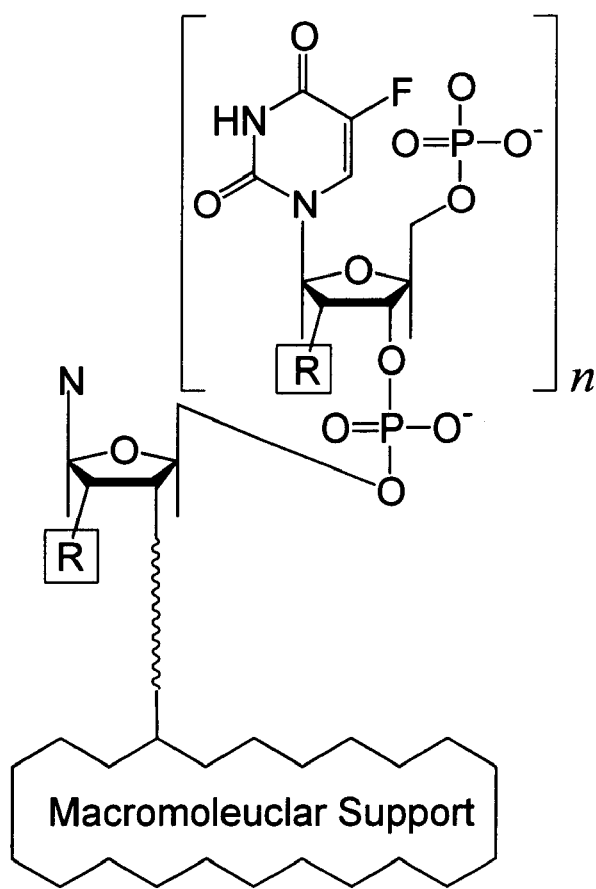
FIG. 16 illustrates a nucleotide-based prodrug comprised of nucleotide component containing pharmacologically active nucleoside analogs, in this example 5-fluorouridylic acid residues. The 5-FU polymer is attached at its base to a pharmacologically non-active anchoring nucleotide, which is linked to a poorly diffusible macromolecular support via a highly nuclease-resistant bond, a phosphodiester bond including a 2'-O-methyl ribose.

Non-Aptameric Nucleotide-Based Prodrugs Containing Oncolytic or Antiviral Nucleoside Analogs It would be useful for certain clinical applications to have small molecule prodrugs that can be sequestered in discrete tissue compartments, and which gradually release oncolytic or antiviral nucleoside analogs into the diseased tissue. One embodiment of the present invention provides nucleotide-based prodrugs comprising nucleotide components comprised of 50 or fewer nucleotides. These nucleotides or nucleotide polymers can be attached covalently to a macromolecular support, which serves to limit the diffusion of the prodrug in the diseased tissue. Such prodrugs also have one or more nucleotides that are converted to oncolytic or antiviral drugs after being released and activated by the hydrolysis of junctional ester bonds. An example of this embodiment is illustrated in FIG. 15. The prodrug in FIG. 16 contains an oncolytic nucleoside, 5-fluorouridine (Chabner, B. A. supra), however, any nucleoside analog may be used, including the drug listed in Tables 1 and 2.

Nucleotide-based prodrugs comprising pharmacologically active non-nucleoside compounds bonded via a junctional phosphodiester bond to nucleotide components are assembled as described in Example 1. The addition of an oligonucleotide to a macromolecular support (e.g., any polymer with appropriate functional groups) can be achieved by direct conjugation of the macromolecular support to a phosphoramidite. Alternatively, the macromolecular support may be derivatized to create a solid phase phosphoramidite, which may be combined to the appropriate nucleotide or nucleotide chain. The choice of a macromolecular support is dictated by the particular application. Examples of suitable supports are described in Example 7. The addition of small molecule drugs to an oligonucleotide can be achieved by direct conjugation to the 5' end with a phosphoramidite derivatized drug or by phosphitilyation of the 5' hydroxyl group and coupling to a hydroxyl version of the drug.

In a preferred embodiment for cutaneous neoplasms, the above mentioned oncolytic prodrugs are introduced into the skin lesion by direct injection, iontophoresis, or a modification of established iontophoretic methods. For example, the prodrugs may be directly injected into the dermis underneath a neoplastic skin lesion. The novelty of the present invention lies in the sustained release properties of the prodrugs, which may avert scarring associated with surgery. The above mentioned oncolytic prodrugs may be used for any neoplastic disorder of sqamous epithelium, for example, actinic keratosis, basal cell carcinoma, kertoacanthoma, leukoplakia with atypia, squamous cell carcinoma, seborrheic keratosis or cutaneous lymphomas. The above mentioned antiviral prodrugs may be used for any virally induced hyperplasia, including but not limited to warts and apthous ulcers located in the superficial tissues, including but not limited to the skin and mucous membranes.

EXAMPLE 9

Nucleotide-Based Prodrugs Containing Ceramide Analogs

Ceramide is a well established intracellular lipid second messenger that mediates the effects of many growth suppressive and apoptotic signaling pathways, including apoptosis (programmed cell death) induced by tumor necrosis factor α, the Fas ligand, and many cytotoxic chemotherapeutic agents (Hannun, Y. A. (1996) Science 274:1855–1859). Ceramide is released from a naturally occurring membrane phospholipid, sphingomyelin when phospholipases cleave phosphodiester bonds that link ceramide to phosphocholine in the sphingomyelin molecule. The structure of sphingomyelin is shown in FIG. 25. Ceramide amplifies the growth suppressive signals by activating enzymes inside of the cell. Thus, sphingomyelin on the outer surface of the cell membrane is essentially a large reservoir of membrane bound "pro-ceramide."

It would be useful for certain clinical applications to have nucleotide-based prodrugs that can be sequestered in discrete tissue compartments, and which gradually release pharmacologically active ceramide analogs into a small volume of diseased tissue. One example of this embodiment is a C-6 ceramide analog attached to a photoreactive bases in the nucleotide component via a phosphodiester bond (FIGS. 24 and 25). Such a prodrug may release and thereby activate the C6 ceramide analog by the hydrolysis of a phosphodiester bond. The rate of hydrolysis of such ceramdie-nucleotide prodrugs would be determined by multiple factors, including the polarity of the linkage (i.e., whether the nucleotide is attached via its 3' or 5' hydroxyl group). In cases where the ceramide analog is linked via its 3' hydroxyl group to a phosphate group, modification of the 2' position the ribose ring will affect the rate of hydrolysis and hence the rate of sustained drug release. The drug formulation will also affect the rate of ester bond hydrolysis. For example, the ceramide prodrugs may be administered as emulsions, in which case it is oriented with polarity within the lipid bilayer. In each case, the phosphodiester bond may be either shielded from, or exposed to, esterases in the aqueous phase. Thus, the formulation may markedly affect the sustained release properties of these prodrugs. The prodrug in FIGS. 24 and 25 contain C6-ceramide, but any non-nucleoside drug may be used, including other ceramide analogs and the drugs listed in Tables 3–8.

Nucleotide-based prodrugs comprising pharmacologically active non-nucleoside compounds bonded via a junctional phosphodiester bond to nucleotide components are assembled as described in Example 1. The addition of an oligonucleotide to a macromolecular support (e.g., any polymer with appropriate functional groups) can be achieved by direct conjugation of the macromolecular support to a phosphoramidite. Alternatively, the macromolecular support may be derivatized to create a solid phase phosphoramidite, which may be combined to the appropriate nucleotide or nucleotide chain. The choice of a macromolecular support is dictated by the particular application. Examples of suitable supports are described in Example 7. The addition of ceramide to an oligonucleotide can be achieved by many established chemistry protocols, including direct conjugation of a hydroxyl group on ceramide with a 3' or 5' phosphoramidite contributed by the nucleotide component. Alternatively, the ceramide may be converted into a phosphoramidite, which can be added to the 3' or 5' hydroxyl group of the nucleotide component.

In embodiments preferred for cutaneous lesions, the ceramide-nucleotide prodrugs may be introduced into the skin lesion by passive diffusion, direct injection, iontophoresis, or a modification of established iontophoretic methods. The novelty of the present invention lies in the sustained release properties of the ceramide, which may achieve therapeutic benefits through its growth suppressive actions. The invention provides a novel method by which to administer ceramide analogs which in concentrated preparations, and in their native chemical forms, are toxic to cells. The invention also provides a method of treating diverse skin diseases without the risk of scarring, which is associated with surgical therapies. Prodrugs containing ceramide analogs may be used for neoplastic disorders of sqamous epithelium for example, actinic keratosis, basal cell carcinoma, kertoacanthoma, leukoplakia with atypia, squamous cell carcinoma, seborrheic keratosis and cutaneous lymphomas. Prodrugs containing ceramide analogs may also be used for virally induced hyperlasia, including but not limited to warts and apthous ulcers located in the superficial tissues, including but not limited to the skin and mucous membranes. Prodrugs containing ceramide analogs may also be used for diseases of presumed autoimmune etiology, including but not limited to psoriasis, lichen planus and refracatory atopic dermatitis.

EXAMPLE 10

Nucleotide-Based Prodrugs Containing Vitamin D Analogs

Figures 21A, 21B:
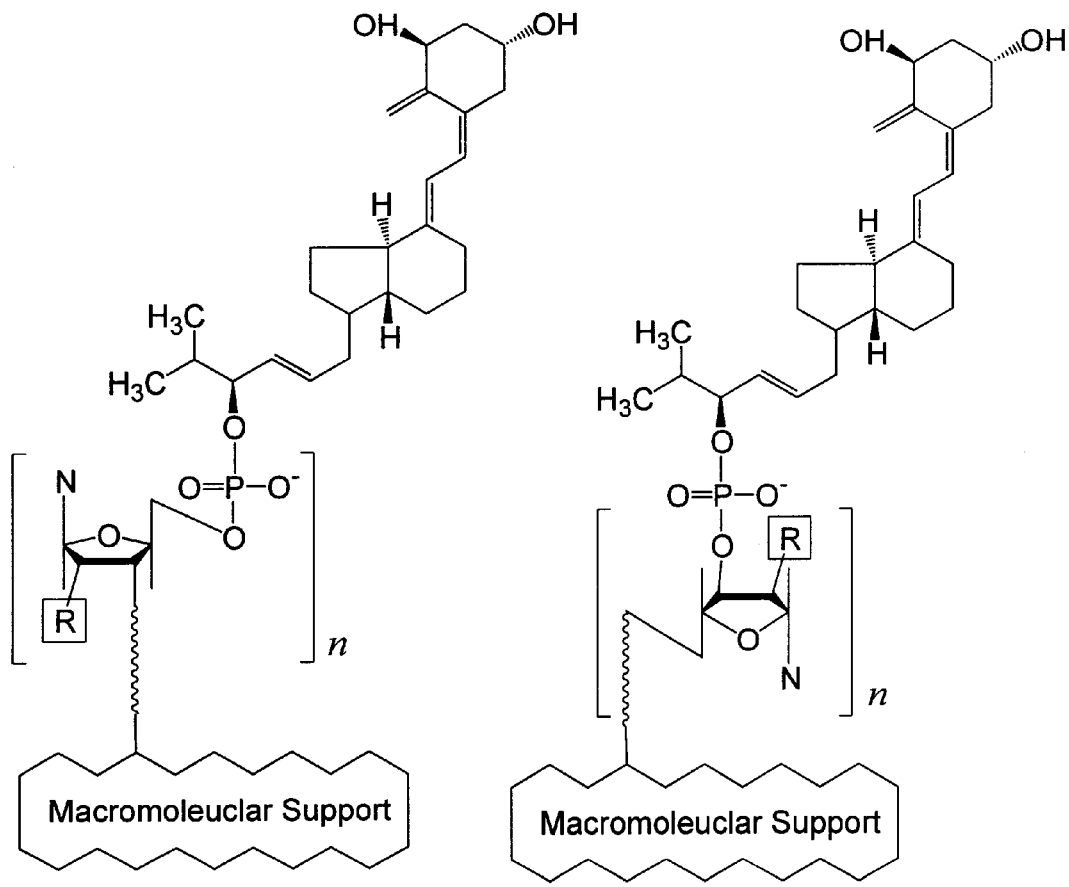
FIGS. 21A and B illustrate examples of nucleotide-based prodrugs comprised of tachysterol coupled to nucleotide components via 5' junctional phosphodiester bonds (21A) or 3' junctional phosphodiester bonds (21B).

It would be useful for certain clinical applications to have nucleotide-based prodrugs that are deposited in discrete tissue compartments, and which gradually release pharmacologically active vitamin D analogs into the diseased tissue. One example of this embodiment is calcipotriene attached to a nucleotide component via a junctional phosphodiester bond (FIG. 21). Such a prodrug may release and thereby activate the calcipotriene molecule by the hydrolysis of a junctional phosphodiester bond. The rate of hydrolysis of such compounds is determined by multiple factors, including the polarity of the linkage, that is whether the nucleotide is attached via its 3' or 5' hydroxyl group. In cases where calcipotriene is linked via its hydroxyl group to a 3' phosphate group, modification of the 2' position the ribose ring should affect the rate of hydrolysis and hence the rate of sustained drug release. The drug formulation will also affect the rate of ester bond hydrolysis. For example, the above mentioned prodrug may be administered as an emulsion, in which case the amphiphilic prodrug is oriented with polarity in the lipid bilayer. The phosphodiester bond may be either shielded from, or exposed to, esterases in the aqueous phase. Thus, the formulation may markedly affect the sustained release properties of these prodrugs. The prodrug in FIG. 21 contains calcipotriene, but any non-nucleoside drug may be used, including all of the examples illustrated in Tables 3–7

Nucleotide-based prodrugs comprising vitamin D analogs bonded via a phosphodiester bond to nucleotide components are assembled as described in Example 1. The addition of an oligo to a macromolecular support (e.g., any polymer with appropriate functional groups) can be achieved by direct conjugation f the macromolecular support to a phosphoramidite. Alternatively, the macromolecular support may be derivatized to create a solid phase phosphoramidite, which may be combined to the appropriate nucleotide or nucleotide chain. The choice of a macromolecular support is dictated by the particular application. Examples of suitable supports are described in Example 7. The addition of vitamin D analogs to a nucleotide component can be achieved by direct conjugation of the 5' end with a phosphoramidite derivatized cholecalcipherol (e.g., tachysterol phosphoramidite).

In embodiments preferred for cutaneous lesions, the above mentioned prodrugs are introduced into the skin lesion by passive diffusion, direct injection, iontophoresis, or a modification of established iontophoretic methods. After the prodrug has been introduced into the dermis underneath a skin lesion, the affected skin is treated with ultraviolet light to fix the prodrug in the diseased tissue. The novelty of the present invention lies in the sustained release properties of the prodrugs, which may achieve therapeutic benefits without the risk of scarring, which is associated with surgical therapies. Prodrugs containing vitamin D analogs may be used for neoplastic disorders of sqamous epithelium, for example, actinic keratosis, basal cell carcinoma, kertoacanthoma, leukoplakia with atypia, squamoous cell carcinoma, seborrheic keratosis and cutaneous lymphomas. Prodrugs containing vitamin D analogs may also be used for virally induced hyperplasia, including but not limited to warts and apthous ulcers located in the superficial tissues, and including but not limited to the skin and mucous membranes (Guzzo, C. supra). Prodrugs containing vitamin D analogs may also be used for diseases of presumed autoimmune etiology, including but not limited to psoriasis, lichen planus and refractory atopic dermatitis (Guzzo, C. supra).

EXAMPLE 11

Nucleotide-Based Prodrugs Containing Retinoids

Retinoids are well known for their effects on growth and differentiation of many cell types (Marcus, R. And Coulston, A. M. (1996) Fat Soluble Vitamins: Vitamins A, K and E. In: Goodman and Gilman's The Pharmacological Basis of Therapeutics, Ninth Edition. (Hardman, Limbird, Molinoff, Ruddon, and Gilman Eds). McGraww-Hill. United States of America pp. 1573–1590). In particular, certain natural and synthetic retinoids have profound effects on epithelial cells. In the absence of retinoic acid or retinol, the pattern of differentiation in epithelial tissues shifts toward basal cell hyperproliferation and excessive keratinization. Retinoid treatment shifts the epithelium back to a less proliferative phenotype characterized by increased mucous production by goblet cells. The differentiative, anti-proliferative effects of retinoids have proven to be beneficial for the treatment of many skin disorders, including but not limited to acne, gram negative folliculitis, ichthyoses, basal cell carcinoma, squamous cell cancer, keratoacanthoma, cutaneous T-cell lymphoma, actininc keratosis, leukoplakia and psoriasis (Guzzo, C. supra).

A major problem with retinoids is their rapid absorption into dermal capillaries, which can lead to significant systemic levels. Retinoids are extremely potent, pleiotropic drugs with significant potential for teratogenesis. Clearly it would be useful for certain clinical applications to have nucleotide-based prodrugs that can be anchored to discrete tissue compartments, and which gradually release retinoids into the diseased tissue, particularly superficial and accessible tissues, such as skin and mucous membranes.

Figures 22A, 22B:
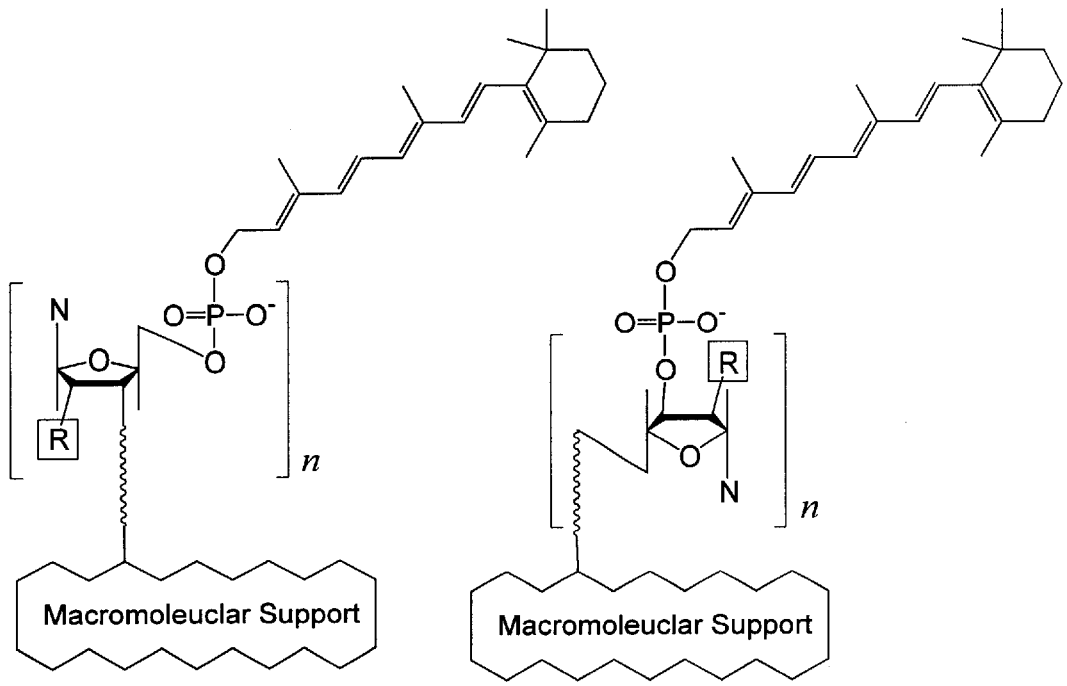
FIGS. 22A and B illustrate examples of nucleotide-based prodrugs comprised of retinol coupled to nucleotide components via 5' junctional phosphodiester bonds (22A) or 3' junctional phosphodiester bonds (22B).

The present invention provides a means by which retinoids may be slowly released into diseased tissues. In one embodiment, retinol or another retinoid with a hydroxyl group, is attached to a poorly diffusible macromeolecular support via a phosphodiester ester bond (FIG. 22). Release and activation of the retinol molecule requires hydrolysis of the ester bond. The rate of hydrolysis is determined by multiple factors, including the polarity of the linkage, that is whether the nucleotide is attached via its 3' or 5' hydroxyl group to the hyroxyl group of the retinol. Modification of the 2' position the ribose ring is expected to affect the rate of hydrolysis and hence the rate of sustained drug release.

Figures 23A, 23B:
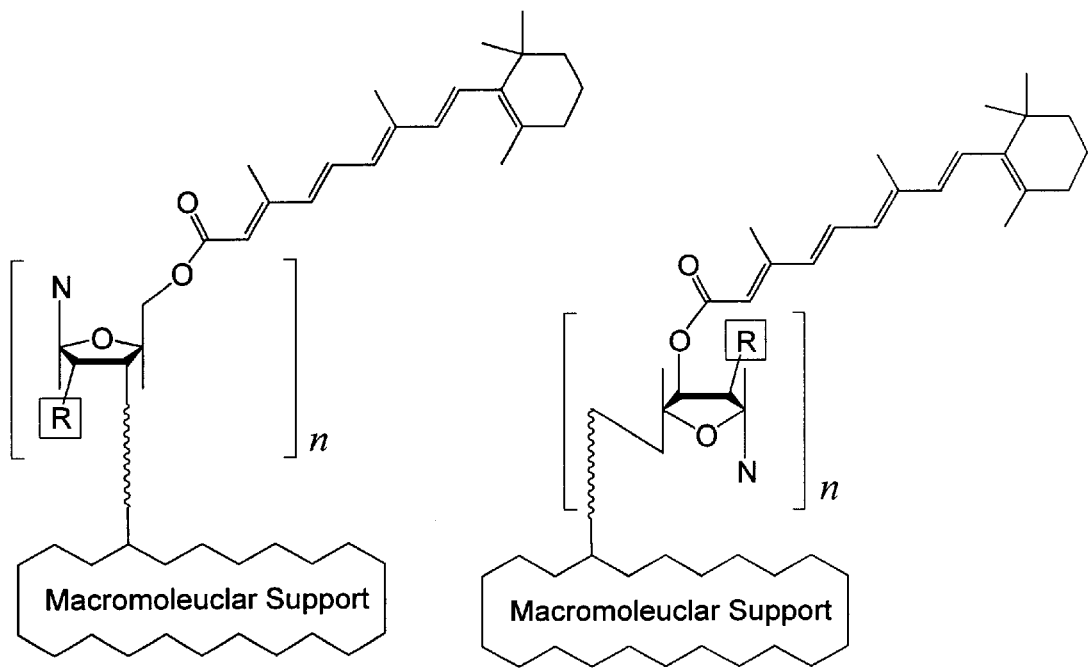
FIGS. 23A and B illustrate examples of nucleotide-based prodrugs comprised of retinoic acid coupled to nucleotide component bonds (23A) or 3' junctional phosphodiester bonds (23B).

In another embodiment, retinoic acid or another retinoid with a carboxyl group, is attached to a poorly diffusible macromolecular polymer via a carbonyl ester bond (FIG. 23). Release and activation of the retinol molecule requires hydrolysis of the ester bond. The rate of hydrolysis is determined by multiple factors, including the polarity of the linkage, that is whether the nucleotide is attached via its 3' or 5' hydroxyl group to the carboxyl group of the retinol. Modification of the 2' position the ribose ring is expected to affect the rate of hydrolysis and hence the rate of sustained drug release.

The drug formulation will also affect the rate of ester bond hydrolysis. For example, nucleotide-based prodrugs comprising retinoid drugs may be administered as emulsions, in which case it is oriented with polarity within the lipid bilayer. In each case, the ester bond may be either shielded from, or exposed to, esterases in the aqueous phase. Thus, the formulation may markedly affect the sustained release properties of these prodrugs. The prodrugs in FIGS. 22 and 23 contain retinol and retinoic acid, respectively, but any retinoid with a hydroxyl or carboxyl group may be used.

Nucleotide-based prodrugs comprising retinoids bonded via a junctional phosphodiester bond to nucleotide components are assembled as described in Example 1. The addition of an oligonucleotide to a macromolecular support (e.g., any polymer with appropriate functional groups) can be achieved by direct conjugation of the macromolecular support to a phosphoramidite. Alternatively, the macromolecular support may be derivatized to a create a solid phase phosphoramidite, which may be combined to the appropriate nucleotide or nucleotide chain. The choice of a macromolecular support is dictated by the particular application. Suitable supports are described in Example 7. The addition of retinoids to a nucleotide component can be achieved by direct conjugation of the 5' end with a phosphoramidite derivatized cholecalcipherol (e.g., retinol phophoramidite).

In embodiments preferred for cutaneous lesions, the retinoid-nucleotide prodrugs are introduced into the skin lesion by passibe diffusion, direct injection, iontophoresis, or a modificatoin of established iontophoretic methods. The novelty of the present invention lies in the sustained release properties of the retinoid, which may achieve therapeutic benefits through its differentiative actions. The invention provides a novel method by which to administer retinoids, which otherwise have the potential for serious systemic side effects. The invention also provides a method of treating diverse skin diseases without the risk of scarring, which is associated with surgical therapies. Nucleotide-based prodrugs containing retinoic acid may be used for neoplastic disorders of sqamous epithelium, for example, actinic keratosis, basal cell carcinoma, kertoacanthoma, leukoplakia with atypia, squamous cell carcinoma or seborrheic keratosis. Prodrugs containing retinoic acid may be used for treatment of acne, gram negative folliculitis, ichthyoses and cutaneous lymphomas (Guzzo, C., supra). Nucleotide-based prodrugs containing retinoic acid may also be used for virally induced hyperplasia, including but not limited to warts located in the superficial tissues, including but not limited to the skin and mucous membranes, and they may be used for diseases of presumed autoimmune etiology, including but not limited to psoriasis, lichen planus and refracatory atopic dermatitis (Guzzo, C., supra).

EXAMPLE 12

Nucleotide-Based Amphiphilic Prodrugs for Improved Liposome Delivery

The ability of nucleotide-based prodrugs to be precisely oriented in a lipid bilayer, and their potential for rapid release and activation, may be exploited to make better liposomes. Amphipathic prodrugs such as those illustrated in FIG. 24 may be readily loaded into liposomes. The hydrophilicity of a short nucleotide component, or a single nucleotide, may be more beneficial in this regard than the charge contributed by a single phosphate group.

Liposomes containing nucleotide-based prodrugs may also have improved in vivo performance. For example, a liposomal prostaglandin $E_1$ formulation is highly unstable in vivo (REF); prostaglandin $E_1$ is released into the bloodstream almost immediately after the liposomes are injected. It would be useful for certain clinical applications to produce stable liposomes with more prolonged sustained release properties. But the junctional phosphodiester or carbonyl ester bond linking the nucleotide to the lipid soluble molecule must be designed or selected for its relative sensitivity to hydrolysis, so that the drug will be activated when the liposome is fragmented in the capillaries of diseased tissues.

EXAMPLE 13

Release of 5' Bromodeoxyuridine (BrdU) from Wax-Oil Depots and Uptake into Tumor Cell Nuclei: Creating Gradients of Nucleoside Analogues in Diseased Tissues The purpose of this experiment was to determine whether a drug depot can release a nucleoside analogue into the surrounding tissue, thereby creating a localized concentration gradient of the nucleotide analogue. Specifically, the goal was to determine if the bioavailable nucleoside analogue is more concentrated in the immediate vicinity of the depot compared to remotely located tissues. To test this idea, an in situ assay was used to determine the relative concentration of bioavailable nucleoside(s) in tissues sections.

5'Bromodeoxyuridine (BrdU) was chosen as a model nucleoside analogue because it can be detected in tissues using anti-BrdU monoclonal antibodies. BrdU is an analogue of deoxythymidine, which like all nucleosides, is transported by a facilitated diffusion mechanism into cells where it is phosphorylated by thymidine kinase (Patterson, A. R. P, et al. (1981) *Pharmacol. Ther.* 12:515). Further phosphorlations convert the BrdU 5' monophosphate to BrdU 5' triphosphate, which is a good substrate of mammalian DNA polymerases. Halopyrimidines such as BrdU are incorporated into DNA during S-phase and this property has been exploited to create radiosensitizers (for reviews see Robertson J. M., et al., (1996). *Cancer*, 78:674–679; McGinn, C. J. and Kinsella, T. J. (1993) *Current Problems in Cancer*, 17:275–321). Immunostaining with anti-BrdU antibodies reveals BrdU residues that have been incorporated into the chromosomes. The frequency of BrdU-positive nuclei in a particular tissue is determined by the local concentration of BrdU and the fraction of cells in S-phase during the BrdU treatment period (i.e., the S-phase labeling index). The amount of BrdU transported into cells is directly proportional to the local concentration of BrdU in the tissue. Therefore, the frequency of BrdU labeled nuclei is an indirect but reliable indicator of the average local concentration of BrdU ini the tissue during the labeling period.

If BrdU is released from an intratumoral drug depot, then it should be incorporated in the chromosomes of proliferating tumor cell surrounding the depot. Furthermore, if the total dose of BrdU is sufficiently small and the BrdU gradient is sufficiently steep, then little or no BrdU should be incorportaed into rapidly proliferating cells located in remote regions of the body, for example the crypt cells of the gut. These ideas were tested by implanting wax-oil-BrdU depots into xenografted U251 glioblastoma tumors. Depots containing BrdU concentrations spanning six orders of magnitude were tested for their ability to label tumor cell nuclei in the vicinity of the depot as well as cell nuclei in the proximal duodenum, liver and skin which are far removed from the tumor.

Experimental Procedures

U251 glioblastoma cells were inoculated into the right flanks of adult female nude mice. When the tumors reached approximately 150 mm$^3$, the BrdU nucleoside preparation was injected intratumorally (day 0). The nucleoside was prepared by thoroughly homogenizing lyophilized BrdU (poweder) in a wax-oil vehicle (90% beeswax/10% sesame oil). The suspensions ranged from 100 ug/ul to 0.001 ug/ul of BrdU (see Table 9), and the injection volume was 40 ul.

Seventy two hours after the injection, the mice were sacrificed. The tumor, liver, skin, and proximal duodenum were fixed in 10% formalin. The tissue samples were dehydrated, parafin-embedded, cut into 6 micron sections and then subjected to a immunostaining procedure. The primary immunostaining antibody was a mouse anti-BrdU monoclonal antibody (IgG2a); Amersham). The secondary immunostaining antibody recognized mouse IgG and was coupled to horseradish peroxidase (HRP). Tissue sections were developed with diaminobenzidine (DAB) substrate, which upon oxidation by HRP is deposited as a brown precipitate in the tissues.

Results

The results are summarized in Table 9. The results indicate that depots containing 4000 (100 mg/kg) or 400 $\mu$g (10 mg/kg) of BrdU label proliferating cells throughout the body, including gut, skin and tumor. Normal liver has a low S-phase fraction and as expected few liver cell nuclei are labeled even at these relatively high doses of BrdU. Depots containing 40 $\mu$g (1 mg/kg) or 4 $\mu$g (0.1 mg/kg) of BrdU fail to label highly proliferative cells in remote sites in the body, for example the gut and skin. The systemic level of BrdU nucleoside is apparently insufficient to label these rapidly proliferating normal cells. Nevertheless, depots containing 4–40 $\mu$g of BrdU label tumor cell nuclei in the immediate vicinity of the oil-wax vehicle which is in the center of the tumor.

These data indicate a local gradient of BrdU nucleoside in the diseased tissue. Additional evidence for a local tissue gradient is provided by the pattern of BrdU incorporation in the tumor: BrdU doses of 4 and 40 $\mu$g intensely label tumor cell nuclei only in the immediate vicinity of the wax-oil vehicle, which is identified histologically by its clear, vacuolated appearance. Interestingly, an intratumoral gradient of BrdU is indicated by the complete lack of BrdU labeled nuclei in the periphery of the tumor.

EXAMPLE 14

Release of Bromodeoxyuridine 5' Monophosphate (BrdU 5'P) from and Intratumoral Depot: Creating Gradients of Nucleotide Analogues in Diseased Tissues Nucleosides are more efficiently taken up by cells than negatively charged nucleotides (Patterson, A. R. P., et al., (1981) *Pharmacol. Ther.* 12:515). Example 13 showed that BrdU delivered in a wax-oil vehicle can label S-phase cells in xenografted tumors (Protcol #M970228). The purpose of the present example was to determine whether BrdU 5'monophosphate (BrdU-5'P) can label tumor cell nuclei in the immediate vicinity of the wax-oil vehicle. To test this idea, 4.8 μmoles of BrdU-5'P in a wax-oil vehicle were injected into a U251 tumor. Four days later, tumor and gut were harvested and immunostained with anti-BrdU antibodies. Intense BrdU labeling of nuclei was observed in tumor cells surrounding the depot.

Two explanations may account for this outcome: (1) BrdU-5'P nucleotide is taken up by cells in the immediate vicinity of the depot; and/or (2) BrdU-5'P is dephosphorylated to BrdU nucleoside which is taken up by the cells surrounding the depot.

This experiment suggests that enzymatic hyrolysis of BrdU-contaninig oligonucleotides generates BrdU nucleotides and/or nucleosides capable of being taken up by cells in the immediate vicinity of depots loaded with BrdU containing oligonucleotides. The latter ideas have been tested as described in Examples 15.

EXAMPLE 15

Release of BrdU from Immobilized BrdU-Containing Oligonucleotide Depots: Creating Gradients of Nucleoside Analogues in Diseased Tissues The purpose of this experiment was to determine whether BrdU nucleotides and/or nucleosides are released from BrdU containing oligonucleotides that have been immobilized on solid phase supports and implanted into xenografted tumor tissues. Immobilization prevents diffusion of the unhyrolyzed oligonucleotides in tissues. The immobilized oligonucleotides are nevertheless bathed in tissue fluids that may contain enzymes such as exonucleases, endonucleases and phosphodiesterases which are capable of hydrolyzing phosphodiester bonds in the immobilized oligonucleotides.

BrdU is incorporated into nuclei of rapidly proliferating skin, gut and tumor cells, as determined by immunostaining with anit-BrdU antibodies. Oligonucleotides must be hydrolyzed to nucleotides before the constituent bases can be incorporated into the chromosomal DNA during S-phase, so this immunostaining assay provides unequivocal evidence that BrdU nucleotides and/or nucleosides have been released from the nucleotide component and converted into BrdU nucleotide triphosphates inside the cells.

The internucleotide (phosphodiester) bonds of oligodeoxynucleotides are more resistant to endonuclease mediated hydrolysis if the 2' hydrogen of the ribose ring is substitued with functional groups such as a 2'-O-methyl group (Sproat et al., (1989) *Nuc. Acids Res.* 17:3373). In addition, the 3' end of oligodeoxynucleotides may be made more resistant to exonuclease mediated hydrolysis by adding an inverted thymidylic acid residue that is coupled to the penultimate nucleotide via an unnatural 3'-3' phosphodiester bond. This structure is referred to as a 3'-3'dT cap.

Using the above mentioned chemical modifications to alter nuclease sensitivity, there BrdU containing oligonucleotides were synthesized (Table 10). All three oligonucleotides have a hexylamine group and two biotin-triethylene glycol residues on the 5' end. Oligo #1 (SEQ ID NO:1) is comprised of 20 residues, including 8 BrdU residues which alternate with 9 deoxynucleotides. Oligo #1 has dA on it's 3+ end and lacks a 3'—3' dT cap. Oligo #2 (SEQ ID NO:2) is identical to Oligo #1 except that Oligo #2 contains a 3'—3' dT cap. Oligo #1 may be more sensitive to exonuclease-mediated hydrolysis than Oligo #2. Oligo #3 (SEQ ID NO:3) contains 8 BrdU residues, which are alternated with endonuclease resistant 2'-O-methyl modified residues. Oligo #3 contains a 3'—3' dT cap, so it is predicted to be more resistant to nuclease activity than Oligos #1 and #2. The major endonucleolytic cleavage products of Oligo #3 probably include the following dinucleotides: 2'-O-methyl Adenylate-BrdU, 2'-O-methyl Guanylate-BrdU, 2'-O-methyl Thymidylate-BrdU and 2'-O-methyl Cytidylate-BrdU. Dinucleotides are not taken up efficiently by cells, and they cannot be incorporated into chromosomes by DNA polymerases. Therefore, it is expected that the Oligos #1 and #2 will hydrolyze into BrdU nucleotides and/or nucleosides; Oligo #3 is expected to release less BrdU to the tumor cells.

Experimental Procedures

Preparation of Streptavidin Immobilized BrdU Containing Oligonucleotides 3000 picomoles of each of the three oligonucleotides listed above (Oligos #1, #2 and #3) was dissolved in 10 mM Tris-HCl/0.5 mM EDTA buffer and incubated overnight with 50 μl of packed streptavidin beads (Sigma Chemical Co. #S-1638). This provided 24,000 picomoles of BrdU per sample.

Preparation of Wax-Oil Immobilized BrdU Containing Oligonucleotides 60,180 picomoles of each of the three oligonucleotides listed above (Oligos #1, #2 and #3) was dissolved in water and lyophilized. The dried oligonucleotide preparations were suspended thoroughly in 50 μl of a wax-oil vehicle (90% beeswax/10% sesame oil). This provided 480,000 picomoles of BrdU per sample.

Preparation of Nitrocellulose Immobilized BrdU Containing Oligonucleotides 60,180 picomoles of each of the three oligonucleotides listed above (Oligos #1, #2 and #3) was dissolved in 10 mM Tris-HCl/0.5 mM EDTA buffer and applied onto disks of nitrocellulose (N/C) that were 1.5 cm in diameter. The oligonucleotides were dried with a hair dryer and stores in the refrigerator until implantation. The density of oligonucleotide on the N/C membrane was 340 picomoles/mm$^2$. The surface area of the N/C filters was 177 mm$^2$ so the total dose was 60,180 picomoles (16 mg/kg). The implant provided a potential total of 480,000 picomoles of BrdU.

Implantation of BrdU-Containing Oligonucleotides into Xenografted Tumors

U251 glioblastoma cells were inoculated into the right flanks of adult female nude mice. When the tumors reached approximately 100 mm$^3$, each of the 3 BrdU-containing oligonucleotide preparations listed above were injected or inserted into a xenografted tumor (day 0). The BrdU oligonucleotide-streptavidin beads were injected subcutaneously adjacent to the tumors, whereas the wax-oil depots of BrdU oligonucleotides were injected into the center of the tumor. The N/C vehicles were inserted into surgical incisions within the tumors, and the tumor and skin wounds were sutured with super-glue.

Preparation and Analysis of Xenografted Tumor Tissue

Ninety six hours after the injection, the mice were sacrificed. The tumor, skin, and proximal duodenum were fixed in 10% formalin. The tissue samples were dehydrated, paraffin-embedded, cut into 6 micron sections and then subjected to an immunostaining procedure. The primary immunostaining antibody was mouse anti-BrdU monoclonal antibody (IgG2a; Amersham). The secondary immunostaining antibody recognized mouse IgG and was coupled to horseradish peroxidase. Tissue sections were developed with diaminobenzidine (DAB) substrate, which upon oxidation by HRP is deposited as a brown precipitate in the tissues.
Results Streptavidin-Immobilized Oligonucleotides (Table 11)

BrdU labeled tumor cell nuclei were observed in the immediate vicinity of streptavidin-immobilized Oligos #1 and #2. BrdU positive nuclei were not observed in the gut, indicating that the level of free BrdU nucleoside in the systemic circulation was insufficient to label the highly proliferative proximal duodenal cells. These data strongly suggest that there was a localized gradient of BrdU nucleoside. The latter conclusion is further supported by the pattern of BrdU positive nuclei in the tumor tissue adjacent to Oligo #2: Skin cells were labeled in a single focus adjacent to the tumor—a focus immediately above the streptavidin beads. These data indicate that immobilized BrdU-containing oligonucleotides release free BrdU into the surrounding tissues and that a gradient is produced leading to selective labeling of cells adjacent to the depot.

No tumor or skin cells were labeled in the vicinity of the Oligo #3 depot, and there were no BrdU positive nuclei observed in the crypts or villi of the gut. The most likely explanation for this result is that the 2'-O-methyl residues in Oligo #3 stabilize the internucleotide phosphodiester bonds thereby reducing the rate of nuclease mediated hydrolysis of this oligonucleotide.

Wax-Oil-Immobilized Oligonucleotides (Table 12)

BrdU labeled tumor cell nuclei were observed the immediate vicinity of was-oil-immobilized Oligos #1 and #2. Less than $\frac{1}{1000}$ BrdU positive nuclei were observed in the gut, indicating that the level of free BrdU nucleoside in the systemic circulation was probably less than the levels obtained in the skin. These data strongly suggest that there was a localized gradient of BrdU nucleoside. The latter conclusion is further supported by the striking field effects observed in the tumor tissue: BrdU positive nuclei were identified in regions of the tumor surrounding the depot, but not in the periphery of the tumor. In addition, skin cells were labeled near the needle track where BrdU-containing oligonucleotides and/or BrdU nucleoside might have diffused most rapidly from the depot. These data indicate that wax-oil immobilized BrdU-containing oligonucleotides release free BrdU into the surrounding tissues and that a gradient is produced leading to selective labeling of cells adjacent to the depot.

No tumor or skin cells were labeled in the vicinity of the Oligo #3 depot, and there were no BrdU positive nuclei observed in the crypts or villi of the gut. The most likely explanation for this result is that the 2' O-methyl residues in Oligo #3 stabilize the internucleotide phosphodiester bonds thereby reducing the rate of nuclease mediated hydrolysis of this oligonucleotide.

Nitrocellulose-Immobilized Oligonucleotides (Table 13)

BrdU labeled tumor cell nuclei were observed in the immediate vicinity of the nitrocellulose-immobilized Oligos #1 and #2. Less than $\frac{1}{1000}$ BrdU positive nuclei were observed in the gut, indicating that the level of free BrdU nucleoside in the systemic circulation was probably less than the levels obtained in the skin. These data strongly suggest that there was a localized gradient of BrdU nucleoside. The latter conclusion is further supported by the striking field effects observed in the tumor tissue: BrdU positive nuclei were identified in regions of the tumor surrounding the nitrocellulose filter. The frequency and intensity of BrdU nuclear labeling was much less in the periphery of the tumor. In addition, skin cells were labeled near the incision site where BrdU-containing oligonucleotides and/or BrdU nucleoside might have diffused most rapidly from the nitrocellulose filter. These data indicate that nitrocellulose immobilized BrdU-containing oligonucleotides release free BrdU into tumor tissue surrounding the nitrocellulose filter and that a gradient is produced leading to selective labeling of cells adjacent to the depot.

No tumor or skin cells were labeled in the vicinity of the Oligo #3 depot, and there were no BrdU positive nuclei observed in the crypts or villi of the gut. The most likely explanation for this result is that the 2'-O-methyl residues in Oligo #3 stabilize the internucleotide phosphodiester bonds thereby reducing the rate of nuclease mediated hydrolysis of this oligonucleotide.

The results of these experiments indicate that BrdU is released via hydrolysis from immobilized oligonucleotides (i.e., depots) that have been inserted into tumors. The major implication of this study is that oligonucleotide depots can be used to create highly localized gradients of therapeutic nucleoside analogs within diseased tissues. Various approaches (wax-oil vehicle, streptavidin beads and nitrocellulose filter binding) were used in this example to immobilize oligonucleotides so that they do not diffuse in the tissues. The binding properties of nucleic acid ligands could also be exploited to retain the oligonucleotides in the diseased tissue.

EXAMPLE 16

Intradermal Gradients of BrdU Nucleoside Adjacent to Oligonucleotide Depots Implanted Beneath Mouse Skin The purpose of the following experiments was to determine the relative levels of BrdU nucleoside released into the skin tissue from nitrocellulose-immobilized depots of each of the oligonucleotides listed in Table 10. If the 2'-O-methyl ribose modifications bestow nuclease resistance upon Oligo #3, then this oligonucleotide should deliver less BrdU to the tissue as determined by a lower frequency of BrdU labeled nuclei. Mouse skin was chosen as an experimental system, because oligonucleotide-nitrocellulose filters may be easily implanted and the epithelial cells in the germinative layers of the skin are easily scored for nuclear incorporation of BrdU.

Experimental Procedures

Preparation of Nitrocellulose-Immobilized Oligonucleotides Containing BrdU Residues The nitrocellulose-immobilized oligonucleotides containing BrdU residues were prepared as described in Example 15. The nitrocellulose-oligonucleotide vehicles were inserted subcutaneously in a midline position of the dorsal lumbar surface (back) of female nude mice. The nitrocellulose filters were inserted with the oligonucleotide side facing the basal cells and hair follicles in the skin. The filters were secured on one edge with super-glue and the surgical wound was closed with super-glue. The mice were sacrificed 96 hrs after implantation. The following tissue samples were prepared by dissection: (1) skin overlying the nitrocellulose vehicles; (2) skin from remote region (flank); and (3) proximal duodenum. Tissues were fixed in 10% formalin for 5 hours.

The tissue samples were dehydrated, paraffin-embedded, cut into 6 micron sections and then subjected to an immunostaining procedure. The primary immunostaining antibody was a mouse anti-BrdU monoclonal antibody (IgG2a; Amersham). The secondary immunostaining antibody recognized mouse IgG and was coupled to horseradish peroxidase. Tissue sections were developed with diaminobenzidine (DAB) substrate, which upon oxidation by HRP is deposited as a brown precipitate in the tissues.

Results

The frequency of nuclear BrdU labeling was scored in the hair follicles and in the superficial (non-adnexal) malpighian layer of skin overlying the nitrocellulose-oligonucleotide depots. In addition, nuclear BrdU labeling was scored in sections of skin taken from remote sites and in epithelial cells of the crypts and villi of the proximal duodenum. These results are presented in FIG. 27.

Figure 27:
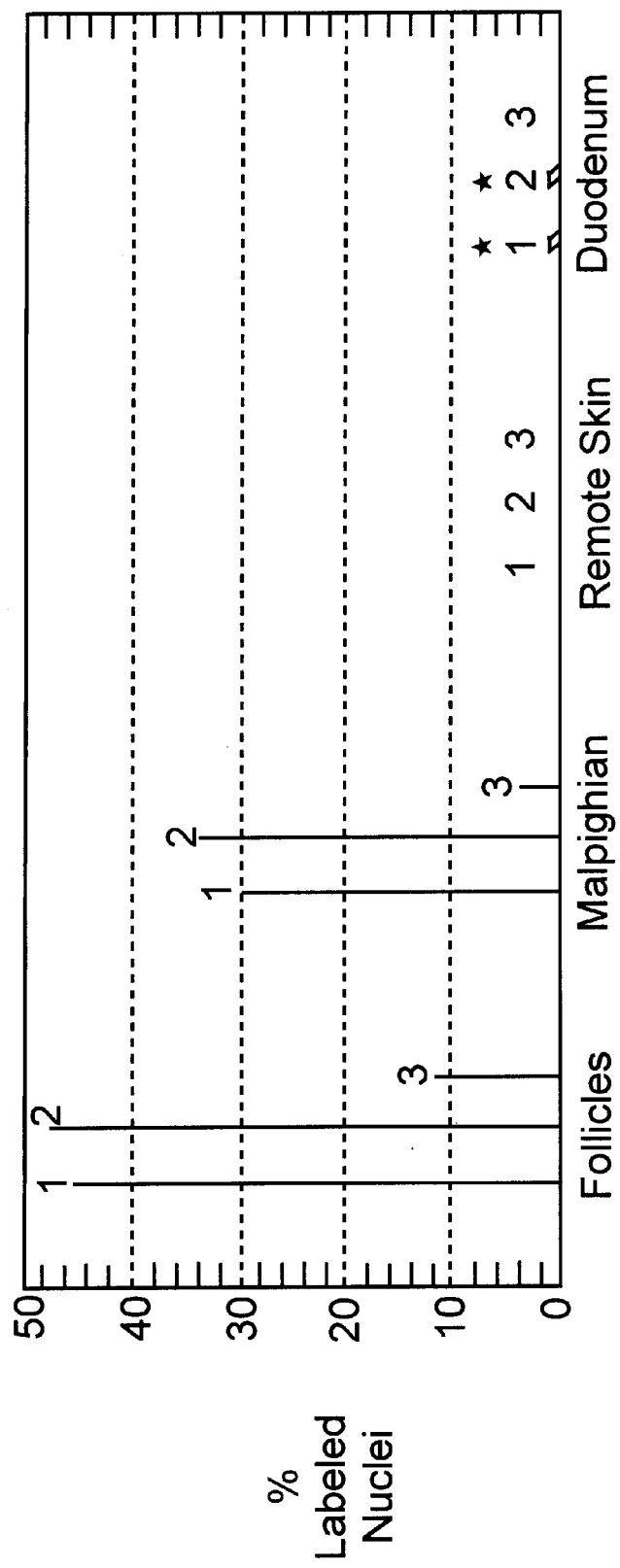
FIG. 27 illustrates the percentage of oligonucleotides #1, #2 and #3 released from drug depots into follicles, malpighian, remote skin and duodenum

Depots containing Oligos #1 and #2 released sufficient BrdU to label nearly half of the cells in hair follicles and nearly ⅓ of the cells in the superficial malpighian layer during the 4 day period (FIG. 27). Only trace labeling (1/1000 cells) was observed in cells of the proximal duodenum. Examination of the skin samples taken from remote areas indicated no BrdU stained nuclei. These data confirm that immobilized oligonucleotide depots generate localized gradients of BrdU necleoside in tissues. The total dose of BrdU was 16 mg/kg, but the systemic levels of BrdU were apparently sufficiently low to avoid labeling of the gut. The levels of BrdU are probably higher in the skin tissue overlying the oligonucleotide depots than in the gut or in skin taken from remote sites.

Figure 28A:
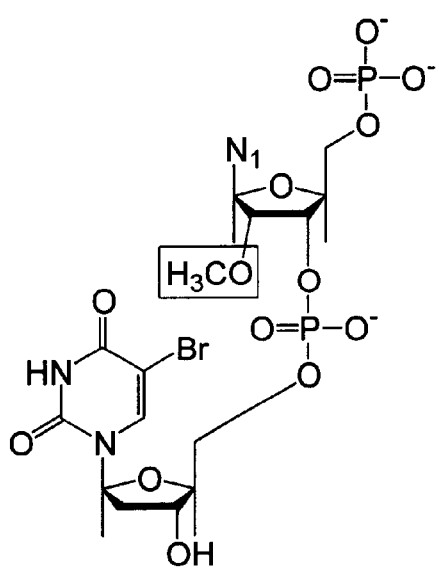
Figure 28B:
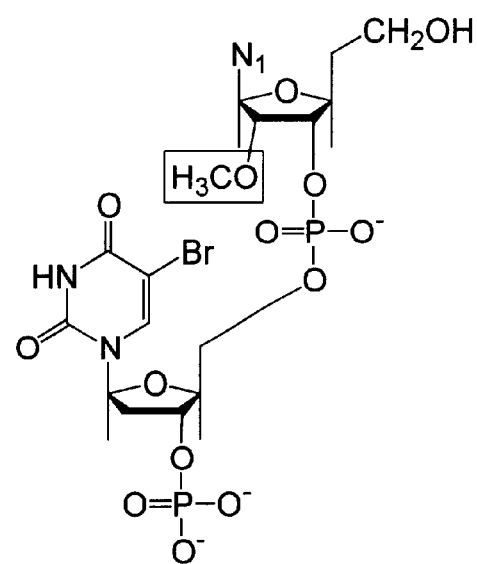

Hydrolysis of Oligos #1 and #2 produced sufficient BrdU to label the nuclei of nearly half of the follicle cells and approximately ⅓ of the cells in the malpighian layer of the skin during the 4 day labeling period. Hydrolysis of Oligo #3 produced much less BrdU as indicated by significantly lower frequencies of nuclear BrdU labeling (11% follicle cell nuclei and 2.5% of cell nuclei in the malpighian layer). The most likely explanation for the above result is that the nuclease resistant 2'-O-methyl modifications in Oligo #3 stabilizes the internucleotide phosphodiester bonds involving the 3' hydroxyl group of the modified nucleotides. Consequently, digestion of Oligo #3 probably yields dinucleotides containing 2'-O-methyl residues on the 5' end and 5'bromodeoxyuridylic acid on the 3' end. Examples of nuclease resistant dinucleotides are shown in FIGS. 28A and 28B. In contrast, nuclease digestion of Oligos #1 and #2 presumably gives rise to single BrdU nucleotides and/or nucleosides, which can be efficiently taken up by cells in the immediate vicinity of the oligonucleotide depots.

Interestingly, the dermal extracellular matrix in skin samples exposed to Oligo #3 is much more heavily stained with anti-BrdU antibodies, possibly indicating that partial hydrolysates have accumulated in the tissue surrounding the N/C vehicle. The accumulation of avidin-reactive (biotin) residues in the dermal extracellular matrix supports the latter interpretation. The nuclear BrdU labeling observed in skin cells exposed to Oligo #3 presumably results from hydrolysis of the latter dinucleotides, perhaps by phosphodiesterases.

These data confirm that oligonucleotides can be used to deliver nucleoside analogues to small volumes of tissue. Significantly, nuclease sensitive Oligos (e.g. #2) deliver much more bioavailable BrdU nucleoside than do nuclease resistant oligos (e.g. #3). These data indicate that localized delivery of nucleoside analogues can be manipulated by altering the sensitivity of the internucleotide (phosphodiester) bonds to enzymatic hydrolysis.

Similar frequencies of BrdU nuclear labeling were observed for Oligos #1 and #2 in hair follicles and the malpighian layer during the 4 day period. The implication is that these two oligonucleotide depots released comparable amounts of BrdU during the labeling period. It remains possible that 3'3' dT cap protection may alter the rate of oligonucleotide hydrolysis under different experimental conditions (e.g., with 2' Fluoro modified oligonucleotides, and/or with a different time course).

TABLE 1

Candidate Drugs for Preparation of Nucleotide-Based Prodrugs

Immunosuppressives and Oncolytic Nucleoside Analogs

Azathioprine
mercaptopurine
6-thioguanine
Erythrohydroxynonyladenine
deoxycoformycin (Pentostatin)
cytosine arabinoside
adenosine arabinoside
2-fluoro Ara-A
5-fluorouracil
2-chloro-deoxyadenosine nucleoside
2',2'-difluoro-2'-deoxycytidine

TABLE 2

Candidate Drugs for Preparation of Nucleotide-Based Prodrugs

Antiviral Agents

3'-deoxy, 3'-azidothymidine (AZT; anti-HIV)
acyclovir (herpes simplex, anti-HSV)
foscarnet

TABLE 2-continued

Candidate Drugs for Preparation of Nucleotide-Based Prodrugs

Antiviral Agents ganciclovir (anti-CMV)
idoxaridine (anti-HSV keratitis)
ribavarin
5-fluoro-3'-thia-2',3'-dideoxycytidine (anti-HBV, HIV)
trifluridine (herpes group, eye)
vidarabine (HSV encephalitis)
sorivudine (1-b-D-arabinofuranosyl-E-5[2-bromovinyl]uracil)

TABLE 3

Candidate Drugs for Preparation of Nucleotide-Based Prodrugs

Lipid Soluble Drugs

Retinoids
Vitamin D Analogs
Steroids
Ceramide Analogs
Prostaglandins
Prostacyclins
Eicosanoid Receptor Antagonists
Thromboxanes
Leukotrienes

TABLE 4

Candidate Drugs for Preparation of Nucleotide-Based Prodrugs

Miscellaneous Antineoplastic Agents bleomycin
cisplatin and Pt analogues: carboplatin, iproplatin
daunorubicin
doxofluoridine
doxorubicin
etoposide
mithramycin
mitomycin c
mitoxanthrone
streptozotocin
taxol and taxotere
vincristine,
vinblastine
vindesine
vinorelbine
topotecan
CPT-11

TABLE 5

Candidate Drugs for Preparation of Nucleotide-Based Prodrugs

Non-Nucleoside Immunosuppressive Drugs

Cyclosporin A
Tacrolimus
Rapamycin
Mycophenolic Acid (MPA)
Brequinar

TABLE 6

Candidate Drugs for Preparation of Nucleotide-Based Prodrugs

Anti-Infectives netilmycin,
amikacin,
gentamycin,
streptomycin,
kanamycin A,
tobramycin.
neomycin B
plicamycin
amphotericin B
vancomycin
5-fluorocytosine

TABLE 7

Candidate Drugs for Preparation of Nucleotide-Based Prodrugs

Short Peptides

Corticotropin (ACTH)
calcitonin
desmopressin (DDAVP)
gonadotropin RH (LH-RH)
goserelin (LHRF)
insulin
lypressin
beta-melanotropin (β-MSH)
alpha-melanotropin (α-MSH)
muramyl dipeptide

TABLE 8

Candidate Drugs for Preparation of Nucleotide-Based Prodrugs

Miscellaneous Drugs

Staurosporine
Morphine

TABLE 9

| BrdU Nucleoside | | Nuclear BrdU Labeling | | | |
|---|---|---|---|---|---|
| Depot | | Tumor | | | |
| ($\mu$g) | (pmol) | (pattern of labeling) | Gut | Skin | Liver |
| 4000 | $1.63 \times 10^6$ | ++++ (uniform staining of tumor cells) | +++++ | +++++ | <1%+ |
| 400 | $1.63 \times 10^5$ | ++++ (uniform staining of tumor cells) | ++++ | +++ | <0.1%+ |
| 40 | $1.63 \times 10^4$ | ++++ (local gradient surrounding depot) | – | – | – |
| 4 | $1.63 \times 10^3$ | ++ (local gradient surrounding depot) | – | – | – |
| 0.4 | 163 | – | – | – | – |
| 0.04 | 16.3 | – | – | – | – |
| 0 | 0 | – | – | – | – |

TABLE 10

| Oligo # | Sequence | SEQ ID NO: |
|---|---|---|
| 1 | 5'-NH$_2$ C6-(Biotin TEG)$_2$-(dA-5BrdU-dC-5BrdU-dG-5BrdU-dT-5BrdU)$_2$-dA-3' | 1 |
| 2 | 5'-NH$_2$-C6-(Bio TEG)$_2$-(dA-5BrdU-dC-5BrdU-dG-5BrdU-dT-5BrdU)$_2$-dA3'-3'dT | 2 |
| 3 | 5'-NH$_2$-C6-(Bio TEG)$_2$-(mA-5BrdU-mC-5BrdU-mG-5BrdU-mT-5BrdU)$_2$-mA-3'3'dT | 3 |

NH$_2$ C6 = Aminohexyl Linker
Bio TEG = Biotin-Triethylene Glycol
BrdU = 5-Bromodeoxyuridine nucleotide
dA = deoxyadenosine nucleotide; dC = deoxycytosine nucleotide; dG = deoxyguanosine nucleotide; dT = deoxythymidine nucleotide
mA = 2' O-methyl adenosine; mC = 2' O-methyl cytosine; mG = 2' O-methyl guanosine
mT = 2' O-methyl thymidine
3'-3'dT cap = dT linked via a 3'3' phosphodiester bond to 3' end of oligonucleotide

TABLE 11

| Oligo* | Streptavidin-Immobilized Oligonucleotides: Microscopic Observations |
|---|---|
| #1 | 1) BrdU labeled nuclei observed in tumor cells immediately adjacent to beads<br>2) Gut negative for BrdU labeling |
| #2 | 1) BrdU labeled nuclei observed in tumor cells immediately adjacent to beads<br>2) Striking field effect — labeling adjacent to beads<br>3) BrdU labeled hair follicle and basal cell nuclei observed only in skin adjacent to oligo containing beads<br>4) Gut negative for BrdU labeling |
| #3 | 1) No BrdU labeling of tumor cell nuclei or skin cell nuclei<br>2) Intense immunolabeling of tumor extracellular matrix (i.e. tumor stroma)<br>3) Gut negative for BrdU labeling |

*See Table 10

TABLE 12

| Oligo* | Wax/Oil-Immobilized Oligonucleotides: Microscopic Observations |
|---|---|
| #1 | 1) BrdU labeled nuclei observed in tumor cells immediately adjacent to intratumoral wax-oil depot<br>2) Striking field effect — most intense BrdU labeling adjacent to beads<br>3) Skin negative for BrdU labeling<br>4) <0.1% gut cell nuclei labeled with BrdU |
| #2 | 1) BrdU labeled nuclei observed in tumor cells immediately adjacent to intratumoral wax-oil depot<br>2) BrdU labeling observed >5 mm from wax-oil vehicle in some microscopic sections<br>3) Striking field effect — most intense BrdU labeling adjacent to wax-oil depot<br>4) Basal keratinocytes and hair follicle cells are BrdU stained in skin overlying the tumor<br>5) <0.1% gut cell nuclei labeled with BrdU |
| #3 | 1) No BrdU labeling observed in tumor cell nuclei<br>2) Intense BrdU immunoreactivity observed in extracellular matrix of tumor stroma<br>3) No BrdU labeling observed in skin cell nuclei<br>4) No BrdU labeling observed in duodenal cell nuclei |

*See Table 10

TABLE 13

| Oligo* | Nitrocellulose-Immobilized Oligonucleotides: Microscopic Observations |
|---|---|
| #1 | 1) BrdU labeled nuclei only observed in tumor cells adjacent to intratumoral nitrocellulose vehicle<br>2) Striking field effect — intense BrdU labeling adjacent to nitrocellulose vehicle<br>3) Basal keratinocytes and hair follicle cell nuclei are BrdU stained in skin overlying the tumor<br>4) <0.1% gut cell nuclei labeled with BrdU |
| #2 | 1) BrdU labeled nuclei observed in tumor cells immediately adjacent to nitrocellulose vehicle<br>2) BrdU labeling of nuclei observed throughout tumor (5 mm)<br>3) Striking field effect — most intense BrdU labeling adjacent to nitrocellulose vehicle<br>4) Basal keratinocytes and hair follicle cell nuclei are BrdU stained in skin overlying the tumor<br>5) <0.1% gut cell nuclei labeled with BrdU |
| #3 | 1) No BrdU labeling observed in tumor cell nuclei<br>2) Intense BrdU immunoreactivity observed in extracellular matrix of tumor stroma<br>3) No BrdU labeling observed in skin cell nuclei<br>4) No BrdU labeling observed in duodenal cell nuclei |

*See Table 10

What is claimed is:

1. A nucleotide-based prodrug comprising a nucleotide component covalently bonded via a physiologically hydrolyzable junctional ester bond to a drug component; wherein said nucleotide-based prodrug is selected from a compound having the following formula:

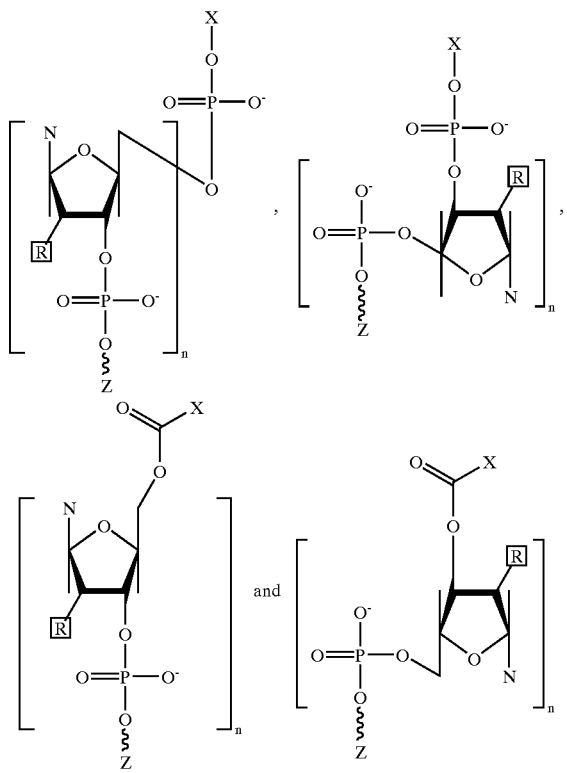

wherein X is independently selected from the group consisting of a drug with a hydroxyl group, a drug with a carboxyl group and H;

R is independently selected from the group consisting of H, OH, F, $OCH_3$ and $NH_2$;

N is independently selected from the group consisting of any base or modification or analog thereof, or non-nucleoside drug selected from the group consisting of ceramide or analogs thereof, vitamin D or analogs thereof and retinoids;

Z is selected from a lipid bilayer vesicle or a macromolecular support; and n=1–150.

2. The nucleotide-based prodrug of claim 1 wherein said nucleotide component is a nucleic acid ligand.

3. The nucleotide-based prodrug of claim 1 wherein said drug component is a nucleic acid ligand.

4. The nucleotide-based prodrug of claims 2 or 3 wherein said nucleic acid ligand is identified by the method comprising:

a) preparing a candidate mixture of nucleic acids;

b) contacting the candidate mixture with a target, wherein nucleic acids having an increased affinity to the target relative to the total candidate mixture may be partitioned from the remainder of the candidate mixture;

c) partitioning the increased affinity nucleic acids from the remainder of the nucleic acids in the candidate mixture; and d) amplifying the increased affinity nucleic acids to yield a mixture of nucleic acids enriched for sequences with increased affinity for the target, whereby a nucleic acid ligand may be identified.

5. The nucleotide-based prodrug of claim 4 wherein said target is a tissue target.

6. The nucleotide-based prodrug of claim 5 wherein said tissue target is diseased.

7. The nucleotide-based prodrug of claim 1 wherein said drug component comprises one or more nucleoside analogs.

8. The nucleotide-based prodrug of claim 7 wherein said nucleoside analog is covalently bonded to said nucleotide component via a junctional phosphodiester bond.

9. The nucleotide-based prodrug of claim 1 wherein said non-nucleoside drug is covalently bonded to said nucleotide component via a junctional carbonyl ester bond.

10. The nucleotide-based prodrug of claim 1 wherein said non-nucleoside drug is covalently bonded to said nucleotide component via a junctional phosphodiester bond.

11. The nucleotide-based prodrug of claim 1 wherein said drug component is a lipophilic compound.

12. The nucleotide-based prodrug of claim 1 wherein said lipid bilayer vesicle is a liposome.

13. The nucleotide-based prodrug of claim 1 wherein said drug component is covalently bonded to the 5'-end of the nucleotide component.

14. The nucleotide-based prodrug of claim 1 wherein said drug component is covalently bonded to the 3'-end of the nucleotide component.

15. A nucleotide-based prodrug comprising a nucleotide component covalently bonded via a physiologically hydrolyzable junctional ester bond to a drug component; wherein said nucleotide-based prodrug is selected from a compound having the following formula:

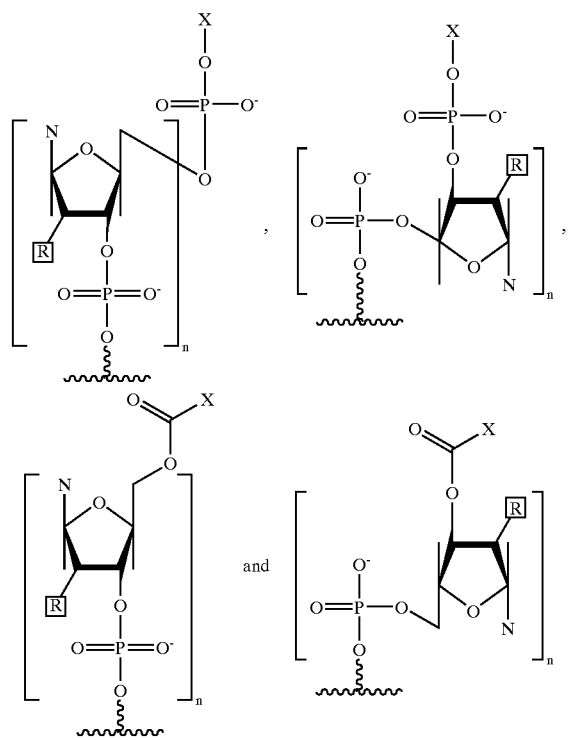

wherein X is independently selected from the group consisting of a drug with a hydroxyl group, a drug with a carboxyl group and H;

R is independently selected from the group consisting of H, OH, F, OCH$_3$ and NH$_2$;

N is a photocrosslinkable base; and n=1–150.

16. The nucleotide-based prodrug of claim 1 wherein said nucleotide component is comprised of 2'-ribose modifications.

17. The nucleotide-based prodrug of claim 1 wherein said macromolecular support is a biocomparible polymer.

18. The nucleotide-based prodrug of claim 1 wherein said macromolecular support is selected from the group consisting of polylactic acid, polyglycolic acid, poly(ε-caprolactone), poly(β-hydroxybutyrate), poly(β-hydroxyvalerate), polydioxanone, poly(ethylene terephthalate), poly(malic acid), poly(tartronic acid), poly(ortho esters), polyanhydrides, polycyanoacrylates, poly(phosphoesters), polyphosphazenes, hyaluronidate, polysulfones, polyacrylamides, polymethacrylate, CarboPol, hydroxyapaptite, chimeric recombinant elastin-silk protein and collagen.

19. A method of preparing a nucleotide-based prodrug; wherein said nucleotide-based prodrug is selected from a compound having the following formula:

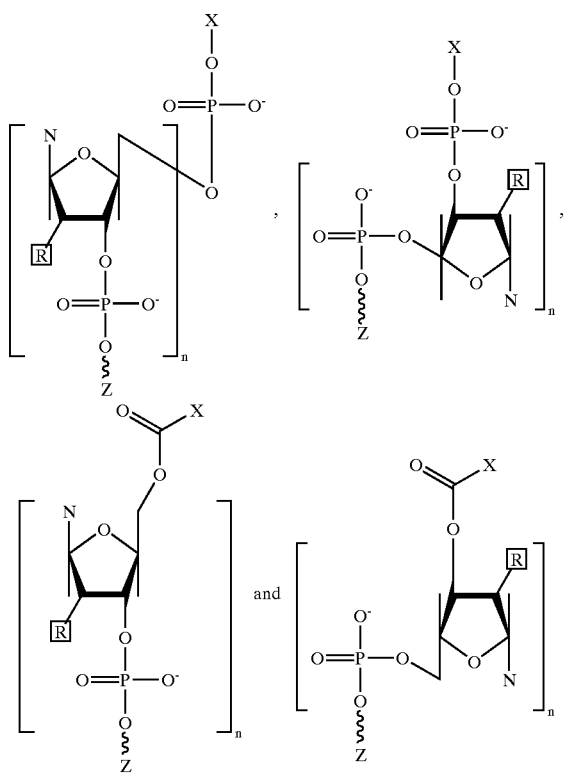

wherein

X is independently selected from the group consisting of a drug with a hydroxyl group, a drug with a carboxyl group and H;

R is independently selected from the group consisting of H, OH, F, OCH$_3$ and NH$_2$;

N is independently selected from the group consisting of any base of modification or analog thereof, or non-nucleoside drug selected from the group consisting of ceramide and analogs thereof, vitamin D and analogs thereof and retinoids;

Z is selected from a lipid bilayer vesicle or a macromolecular support; and n=1–150, said method comprising covalently bonding a nucleotide component to a drug component via a physiologically hydrolyzable junctional ester bond.

20. The method of claim 19 wherein said nucleotide component is a nucleic acid ligand.

21. The method of claim 19 wherein said drug component is a nucleic acid ligand.

22. The method of claim 20 or 21 wherein said nucleic acid ligand is identified by the method comprising:

a) preparing a candidate mixture of nucleic acids;

b) contacting the candidate mixture with a target, wherein nucleic acids having an increased affinity to the target relative to the total candidate mixture may be partitioned from the remainder of the candidate mixture;

c) partitioning the increased affinity nucleic acids from the remainder of the nucleic acids in the candidate mixture; and d) amplifying the increased affinity nucleic acids to yield a mixture of nucleic acids enriched for sequences with increased affinity for the target, whereby a nucleic acid ligand may be identified.

23. The method of claim 22 wherein said target is a tissue target.

24. The method of claim 23 wherein said tissue target is diseased.

25. The method of claim 19 wherein said drug component comprises one or more nucleoside analogs.

26. The method of claim 25 wherein said nucleoside analog is covalently bonded to said nucleotide component via a junctional phosphodiester bond.

27. The method of claim 19 wherein said drug component comprises a non-nucleoside drug.

28. The method of claim 19 wherein said non-nucleoside drug is covalently bonded to said nucleotide component via a junctional carbonyl ester bond.

29. The method of claim 19 wherein said non-nucleoside drug is covalently bonded to said nucleotide component via a junctional phosphodiester bond.

30. The method of claim 19 wherein said drug component is a lipophilic compound.

31. The method of claim 19 wherein said lipid bilayer vesicle is a liposome.

32. The method of claim 19 wherein said drug component is covalently bonded to the 5'-end of the nucleotide component.

33. The method of claim 19 wherein said drug component is covalently bonded to the 3'-end of the nucleotide component.

34. A method of preparing a nucleotide-based prodrug; wherein said nucleotide-based prodrug is selected from a compound having the following formula:

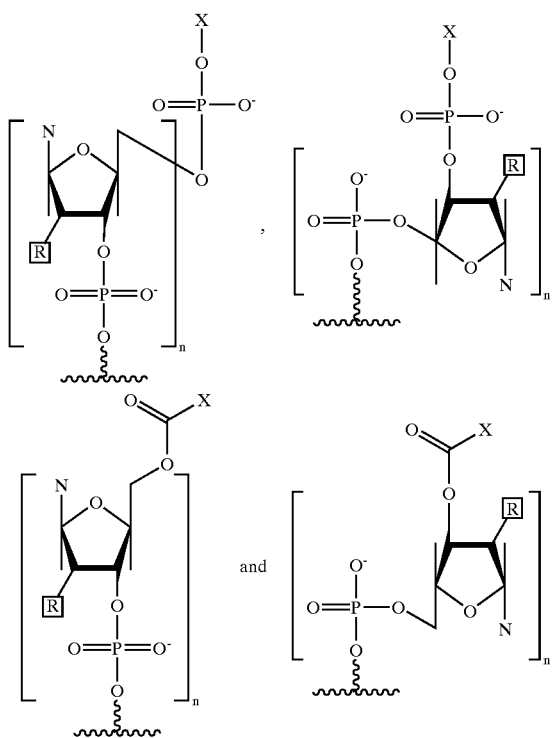

wherein X is independently selected from the group consisting of a drug with a hydroxyl group, a drug with a carboxyl group and H;

R is independently selected from the group consisting of H, OH, F, OCH$_3$ and NH$_2$;

N is a photocrosslinkable base; and n=1–150.

35. The method of claim 19 wherein said nucleotide component is comprised of 2'-ribose modifications.

36. The method of claim 19 wherein said macromolecular support is a biocompatible polymer.

37. The method of claim 19 wherein said macromolecular support is selected from the group consisting of polylactic acid, polyglycolic acid, poly($\epsilon$-caprolactone), poly($\beta$-hydroxybutyrate), poly($\beta$-hydroxyvalerate), polydioxanone, poly(ethylene terephthalate), poly(malic acid), poly(tartronic acid), poly(ortho esters), polyanhydrides, polycyanoacrylates, poly(phosphoesters), polyphosphazenes, hyaluronidate, polysulfones, polyacrylamides, polymethacrylate, CarboPol, hydroxyapaptite, chimeric recombinant elastin-silk protein and collagen.

38. The nucleotide-based prodrug of claim 1, wherein N is independly selected from the group of compounds having the following structural formulas:

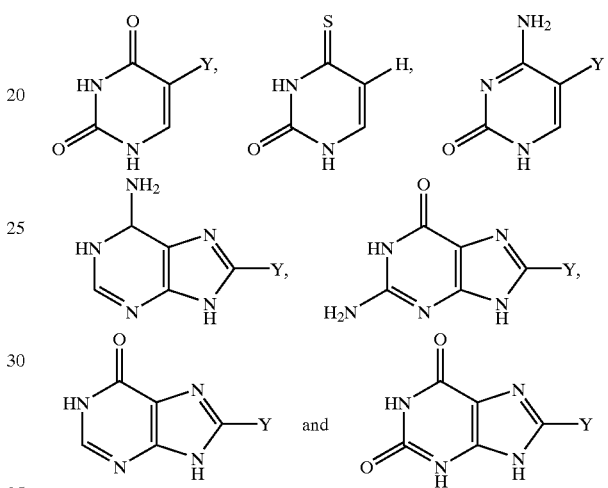

wherein Y is independently selected from the group consisting of Br, I, F, N$_3$, CH$_2$CHBr, CH$_2$CHI, 4-thiouridine and cytosine arabinoside.

* * * * *